US012599578B2

(12) United States Patent
Kirkpatrick

(10) Patent No.: US 12,599,578 B2

(45) Date of Patent: Apr. 14, 2026

(54) COMPOSITIONS COMPRISING ENZYME-CLEAVABLE PRODRUGS AND CONTROLLED RELEASE NAFAMOSTAT AND METHODS OF USE THEREOF

(71) Applicant: Ensysce Biosciences Inc., La Jolla, CA (US)

(72) Inventor: Lynn Kirkpatrick, La Jolla, CA (US)

(73) Assignee: Ensysce Biosciences Inc., La Jolla, CA (US)

( * ) Notice: Subject to any disclaimer, the term of this patent is extended or adjusted under 35 U.S.C. 154(b) by 352 days.

(21) Appl. No.: 17/689,271

(22) Filed: Mar. 8, 2022

(65) Prior Publication Data

US 2022/0287992 A1 Sep. 15, 2022

Related U.S. Application Data

(60) Provisional application No. 63/158,663, filed on Mar. 9, 2021.

(51) Int. Cl.

| | |
|---|---|
| ***A61K 31/155*** | (2006.01) |
| ***A61K 9/16*** | (2006.01) |
| ***A61K 38/07*** | (2006.01) |
| ***A61K 47/32*** | (2006.01) |
| ***A61K 47/38*** | (2006.01) |
| ***A61K 47/64*** | (2017.01) |
| ***A61K 47/65*** | (2017.01) |

(52) U.S. Cl.

CPC .......... *A61K 31/155* (2013.01); *A61K 9/1623* (2013.01); *A61K 9/1635* (2013.01); *A61K 9/1652* (2013.01); *A61K 38/07* (2013.01); *A61K 47/32* (2013.01); *A61K 47/38* (2013.01); *A61K 47/64* (2017.08); *A61K 47/65* (2017.08)

(58) Field of Classification Search

CPC ...... A61K 31/155; A61K 47/65; A61K 47/64; A61K 9/1623; A61K 9/1635; A61K 9/1652; A61K 38/07; A61K 47/32; A61K 47/38

See application file for complete search history.

(56) References Cited

U.S. PATENT DOCUMENTS

| | | | |
|---|---|---|---|
| 913,961 | A | 3/1909 | Levedahl |
| 3,842,064 | A | 10/1974 | Greven |
| 3,850,904 | A | 11/1974 | Greven |
| 3,853,836 | A | 12/1974 | Greven |
| 3,853,838 | A | 12/1974 | Greven |
| 3,875,137 | A | 4/1975 | Jones et al. |
| 4,104,371 | A | 8/1978 | Greven et al. |
| 4,297,346 | A | 10/1981 | Rips et al. |
| 4,454,338 | A | 6/1984 | Fujii et al. |
| 4,532,255 | A | 7/1985 | Fujii et al. |
| 5,109,118 | A | 4/1992 | Mizushima |
| 5,217,987 | A | 6/1993 | Berger |
| 5,352,704 | A | 10/1994 | Okuyama et al. |
| 5,958,459 | A * | 9/1999 | Chasin .................... A61K 9/14 424/490 |
| 6,245,802 | B1 | 6/2001 | Iyengar et al. |
| 6,388,122 | B1 | 5/2002 | Kido et al. |
| 6,586,196 | B1 | 7/2003 | Bronstein et al. |
| 7,060,290 | B1 | 6/2006 | Morimoto et al. |
| 7,105,486 | B2 | 9/2006 | Mickle et al. |
| 7,189,414 | B2 | 3/2007 | Rubinstein et al. |
| 7,223,735 | B2 | 5/2007 | Mickle et al. |
| 7,655,630 | B2 | 2/2010 | Mickle et al. |
| 7,893,105 | B2 | 2/2011 | Xiang et al. |
| 8,163,701 | B2 | 4/2012 | Jenkins et al. |
| 8,217,005 | B2 | 7/2012 | Jenkins et al. |
| 8,497,237 | B2 | 7/2013 | Jenkins et al. |
| 8,569,228 | B2 | 10/2013 | Jenkins et al. |
| 8,685,916 | B2 | 4/2014 | Jenkins et al. |
| 8,802,681 | B2 | 8/2014 | Jenkins et al. |
| 8,921,418 | B2 | 12/2014 | Jenkins et al. |
| 8,962,547 | B2 | 2/2015 | Jenkins et al. |
| 9,023,860 | B2 | 5/2015 | Jenkins et al. |
| 9,040,032 | B2 | 5/2015 | Jenkins et al. |
| 9,095,627 | B2 | 8/2015 | Jenkins et al. |
| 2003/0035831 | A1 | 2/2003 | Modi |
| 2003/0180352 | A1 | 9/2003 | Patel et al. |
| 2004/0063628 | A1 | 4/2004 | Piccariello et al. |
| 2005/0054561 | A1 | 3/2005 | Mickle et al. |
| 2005/0080012 | A1 | 4/2005 | Mickle et al. |

(Continued)

FOREIGN PATENT DOCUMENTS

| | | |
|---|---|---|
| DE | 1041052 | 10/1958 |
| DE | 1493824 | 5/1969 |

(Continued)

OTHER PUBLICATIONS

Bak et al. (1999) “Acyloxyalkoxy-Based Cyclic Prodrugs of Opioid Peptides: Evaluation of the Chemical and Enzymatic Stability as Well as Their Transport Properties Across Caco-2 Cell Monolayers” *Pharm Res* 16(1):24-29.
Bernkop-Schnurch (1998) “The use of inhibitory agents to overcome the enzymatic barrier to perorally administered therapeutic peptides and proteins” *J Control Release* 50(1-2):1-16.
Bioavailability and Bioequivalence Studies for Orally Administered Drug Products—General Considerations, Guidance for Industry, Food and Drug Administration, published on Oct. 2000.
Birk et al. (1976) “Trypsin and chymotrypsin inhibitors from soybeans” *Methods in Enzymology* 45:700-707.
Camostat Medilate (http://www.scbt.com/datasheet-203867-camostat-mesylate.html (downloaded on Nov. 14, 2013).
Danziger and Dean; (1989) “Automated site-directed drug design: a general algorithm for knowledge acquisition about hydrogen-bonding regions at protein surfaces”; Proc R Soc Lond B Biol Sci. 236(1283); pp. 101-113.

(Continued)

*Primary Examiner* — Jeffrey S Lundgren
*Assistant Examiner* — Ibrahim D Bori
(74) *Attorney, Agent, or Firm* — Khin K. Chin; Bozicevic, Field & Francis LLP

(57) ABSTRACT

Aspects of the present disclosure include pharmaceutical compositions, and their methods of use, where the pharmaceutical compositions include an active agent prodrug that provides enzymatically-controlled release of an active agent, and controlled release nafamostat or a pharmaceutically acceptable salt thereof.

12 Claims, 13 Drawing Sheets

(56) References Cited

U.S. PATENT DOCUMENTS

| | | | | |
|---|---|---|---|---|
| 2005/0176644 | A1 | 8/2005 | Mickle et al. | |
| 2005/0176645 | A1 | 8/2005 | Mickle et al. | |
| 2005/0228001 | A1 | 10/2005 | Hanson | |
| 2007/0042955 | A1 | 2/2007 | Mickle et al. | |
| 2007/0082929 | A1 | 4/2007 | Gant et al. | |
| 2007/0093420 | A1 | 4/2007 | Yeomans et al. | |
| 2007/0123468 | A1 | 5/2007 | Jenkins et al. | |
| 2007/0203055 | A1 | 8/2007 | Mickle et al. | |
| 2007/0292511 | A1 | 12/2007 | Kolatkar | |
| 2008/0139653 | A1 | 6/2008 | Mickle et al. | |
| 2009/0013768 | A1 | 1/2009 | Pouteau et al. | |
| 2009/0136980 | A1 | 5/2009 | Bebbington et al. | |
| 2009/0137618 | A1 | 5/2009 | Jenkins et al. | |
| 2009/0192093 | A1 | 7/2009 | Mickle et al. | |
| 2009/0209569 | A1 | 8/2009 | Arnelle et al. | |
| 2009/0324710 | A1 | 12/2009 | Glidden | |
| 2010/0015249 | A1 | 1/2010 | Uwagawa | |
| 2010/0022792 | A1 | 1/2010 | Shen | |
| 2010/0035826 | A1 | 2/2010 | Jenkins et al. | |
| 2010/0080797 | A1 | 4/2010 | Yeomans et al. | |
| 2010/0092562 | A1 | 4/2010 | Hollenbeck et al. | |
| 2010/0227921 | A1 | 9/2010 | Franklin et al. | |
| 2010/0267614 | A1 | 10/2010 | Jenkins | |
| 2010/0286186 | A1 | 11/2010 | Franklin et al. | |
| 2011/0159073 | A1 | 6/2011 | de Juan et al. | |
| 2011/0262355 | A1* | 10/2011 | Jenkins | A61K 31/485 424/9.1 |
| 2011/0262359 | A1 | 10/2011 | Jenkins et al. | |
| 2011/0262360 | A1 | 10/2011 | Jenkins et al. | |
| 2011/0281886 | A1 | 11/2011 | Jenkins et al. | |
| 2012/0178772 | A1 | 7/2012 | Jenkins et al. | |
| 2012/0178773 | A1 | 7/2012 | Jenkins et al. | |
| 2012/0230916 | A1 | 9/2012 | Jenkins et al. | |
| 2012/0232066 | A1 | 9/2012 | Jenkins et al. | |
| 2012/0270847 | A1 | 10/2012 | Franklin et al. | |
| 2013/0022671 | A1 | 1/2013 | Glidden et al. | |
| 2013/0059914 | A1 | 3/2013 | Jenkins et al. | |
| 2013/0210700 | A1 | 8/2013 | Jenkins et al. | |
| 2013/0210701 | A1 | 8/2013 | Jenkins et al. | |
| 2013/0210854 | A1 | 8/2013 | Jenkins et al. | |
| 2014/0121152 | A1 | 5/2014 | Jenkins et al. | |
| 2014/0154313 | A1 | 6/2014 | Counts et al. | |
| 2014/0206597 | A1 | 7/2014 | Jenkins et al. | |
| 2015/0031635 | A1 | 1/2015 | Jenkins et al. | |
| 2018/0085366 | A1* | 3/2018 | Jenkins | A61K 47/61 |
| 2020/0016080 | A1* | 1/2020 | Mulye | A61K 31/138 |

FOREIGN PATENT DOCUMENTS

| | | |
|---|---|---|
| EP | 1782834 | 5/2007 |
| EP | 2433655 | 2/2008 |
| GB | 1425099 | 2/1976 |
| JP | H 0940579 | 2/1997 |
| WO | WO 1997012903 | 4/1997 |
| WO | WO 2002043767 | 6/2002 |
| WO | WO 2004082620 | 9/2004 |
| WO | WO 2005032474 | 4/2005 |
| WO | WO 2005042772 | 5/2005 |
| WO | WO 2007022535 | 2/2007 |
| WO | WO 2007120648 | 10/2007 |
| WO | WO 2007120864 | 10/2007 |
| WO | WO 2007140272 | 12/2007 |
| WO | WO 2008012046 | 1/2008 |
| WO | WO 2008101187 | 8/2008 |
| WO | WO 2008101202 | 8/2008 |
| WO | WO 2009067703 | 5/2009 |
| WO | WO 2009080030 | 7/2009 |
| WO | WO 2009092073 | 7/2009 |
| WO | WO 2009136392 | 11/2009 |
| WO | WO 2010045599 | 4/2010 |
| WO | WO 2010100477 | 9/2010 |
| WO | WO 2010148305 | 12/2010 |
| WO | WO 2011007247 | 1/2011 |
| WO | WO 2011031350 | 3/2011 |
| WO | WO 2011133346 | 4/2011 |
| WO | WO 2011133149 | 10/2011 |
| WO | WO 2011133178 | 10/2011 |
| WO | WO 2011133347 | 10/2011 |
| WO | WO 2011133348 | 10/2011 |
| WO | WO 2012122422 | 9/2012 |
| WO | WO 2020181000 | 9/2020 |

OTHER PUBLICATIONS

Database Internet [Online] Apr. 5, 2005 (Apr. 5, 2005), XP002350634 retrieved from Internet accession No. http://onlineethics.org/reseth/helsinki.html.

Database Registry (2001) Abstract, Database accession No. 339089-42-8; 1 page.

De Nardo et al. (1977) "Studies on chemical structure and sweet taste. Note XIII. L-Acylamidosuccinilic acid derivatives" Database Caplus, Abstract, Database accession No. 1977:119365; 1 page.

Definition of "ex vivo" from thefreedictionary.com, accessed Oct. 7, 2014.

Geratz et al. (1976) "Novel bis(benzamidine) compounds with an aromatic central link. Inhibitors of thrombin, pancreatic kallikrein, trypsin, and complement" *J. Med. Chem.* 19:634-639.

Göke et al. (1984) "Effect of a Specific Serine Protease Inhibitor on the Rat Pancreas: Systemic Administration of Camostate and Exocrine" *Digestion* 30:171-178.

Gomes et al. (2007) "Cyclization-activated prodrugs" *Molecules* 12:2484-2506.

Gotoh et al. (2005) "The advantages of the Ussing chamber in drug absorption studies" *Journal of Biomolecular Screening* 10(5):517-523.

Gottschalk, et al., (2001), "New Concepts inAcute Pain Therapy: Preemptive Analgesia", American Family Physician, 63(10):1979-1984.

Hansch et al. (1990) "Comprehensive Medicinal Chemistry, vol. 5 Biopharmaceutics" *Rational Design, Mechanistic Study and Therapeutic Application of Chemical Compounds, Oxford, Pergamon Press* 5:251-278.

Hijikata-Okunomiya et al. (2000) "Selective Inhibition of Trypsin by (2R,4R)-4-Phenyl-1-[$N^{\alpha}$-(7-methoxy-2-naphthalenesulfonyl)-L-arginyl]-2-piperidinecarboxylic Acid" *J. Biochem.* 275:18995-18999.

Hyams "Medical Conditions: Abdominal Pain, Recurrent" (downloaded on Nov. 21, 2014 from URL: http://www.pediatricweb.com/webpost/iframe/MedicalConditions_465.asp?tArticleId=94 ) 4 pages.

Iwanowicz et al. (2002) "Retro-Binding Thrombin Active Site Inhibitors: Identification of an Orally Active Inhibitor of Thrombin Catalytic Activity" *Bioorganic and Medicinal Chemistry Letters* 12:3183-3186.

Katragadda et al. (2006) "Simultaneous Modulation of Transport and Metabolism of Acyclovir Prodrugs across Rabbit Cornea: An approach Involving Enzyme Inhibitors" *Int J Pharm* 320(1-2):104-113.

Kunze et al. (1983) "Effects of the serine protease inhibitors FOY and FOY 305 on phospholipase A I (EC 3.1.1.32) activity in rat—liver lysosomes" *Pharm. Research Com.* 15: 451-459.

Lapidus and Sweeney (1973) "L-4'-Cyano-3-(2.2.2-trifluoroacetamideo)s uccinanilic Acid and Related Synthetic Sweetening Agents" *J. Med. Chem.* 16(2):163-166.

Lin et al. (1993) "The 0.25-nm X-ray structure of the Bowman-Birk type inhibitor from mung bean in ternary complex with porcine trypsin" *Eur. J. Biochem.* 212:549-555.

Markwardt et al. (1968) "Comparative studies on the inhibition of trypsin, plasmin, and thrombin by derivatives of benzylamine and benzylamidine" *Eur. J. Biochem*, 6:502-506.

Nafamostat (PubChem, National Center for Biotechnology Information dated Dec. 20, 2005).

Nechab et al. (2008) "N-Acylglycinates as acyl donors in serine protease-catalyzed kinetic resolution of amines. Improvement of selectivity and reaction rates." *Org. Biol. Chem.* 6:3917-3920.

Opiois911 (downloaded on Nov. 21, 2014 from URL: http://opioids911.org/safety.php ).

(56) References Cited

OTHER PUBLICATIONS

Ozawa et al. (1966) "The reactive site of trypsin inhibitors" *J. Biol. Chem.* 241:3955-3961.
Pain Doctor, "Phantom Limb Pain", (downloaded on Nov. 21, 2014 from URL: http://paindoctor.com/conditions/common/phantom-limb-pain/ ).
Pauletti, Giovanni et al. (1997) "Esterase-Sensitive Cyclic Prodrugs of Peptides: Evaluation of a Phenylpropionic Acid Promoiety in a Model Hexapeptide" *Pharm Res* 14(1):11-17.
Perona et a l. (1995) "Structural basis of substrate specificity in the serine proteases"; Protein Science vol. 4; pp. 337-360.
Plummer et al. (1997) "Design of peptidomimetic ligands for the pp60srcSH2 domain" *Bioorganic and Medicinal Chemistry* 5(1):41-47.
Prater et al. (2002) "Successful Pain Management for the Recovering Addicted Patient" *Primary Care Companion J Clin Psychiatry* 4(4):125-131.
Ramjee et al. (2000) "The Kinetic and Structural Characterization of the Reaction of Nafamostat with Bovine Pancreatic Trypsin" *Thrmb Res.* 98(6):559-569.
Reddy et al. (2012) "An improved process for the preparation of lisdexamfetamine and its pharmaceutically acceptable salts" Database Caplus, Abstract, Database accession No. 2012:654913.
Renatus et al. (1998) "Structural and Functional Analyses of Benzamidine-Based Inhibitors in Complex with Trypsin: Implications for the Inhibition of Factor Xa, tPA, and Urokinase" *J. Med. Chem.* 41(27):5445-5456.
Schanker et al. (1958) "Absorption of drugs from the rat small intestine" *Journal of Pharmacology and Experimental Therapeutics* 123(1):81-88.
Senoo et al. (1966) "Glutamic acid amides" Database Caplus, Abstract, Database accession No. 1966:19804.
Simone Joseph; "Oncology (Introduction)" Textbook of Medicine, 20(1), pp. 1004-1010 (Year: 1997).
Song, Xiaoping et al. (2002) "Synthesis of a Novel Cyclic Prodrug of RGD Peptidomimetic to Improve Its Cell Membrane Permeation" *Bioorg Chem* 30(4):285-301.
Tanizawa et al. (1987) "Inverse Substrates for Tryspin and Tryspin-like Enzymes" *Acc. Chem. Res.* 20:337-343.
Testa et al. (2003) "Hydrolysis in Drug and Prodrug Metabolism" Verlag Helvetica Chimica Acta, Postfach, CH-8042, Switzerland, pp. 420-534.
Tirkkonen et al. (2004) "Drug interactions with the potential to prevent prodrug activation as a common source of irrational prescribing in hospital inpatients" *Clinical Pharmacology and Therapeutics* 76(6):639-647.
Umezawa (1976) "Structure and activities of protease inhibitors of microbial origin" *Methods in Enzymology* 45:678-695.
Van Gelder et al. (2002) "Intestinal absorption enhancement of the ester prodrug tenofovir disoproxil fumarate through modulation of the biochemical barrier by defined ester mixtures" *Drug Metabolism and Disposition* 30(8):924-930.
Yin, et al (2006) "Properties of poly(lactic-co-glycolic acid) nanospheres containing protease inhibitors: Camostat mesilate and nafamostat mesylate"; International Journal of Pharmaceutics, Elsevier, Amsterdam, NL; vol. 314, No. 1, 11; pp. 46-55; ; XP027972308.
Ishizaki, et al (2008) "Nafamostat Mesilate, a Potent Serine Protease Inhibitor, Inhibits Airway Eosinophilic Inflammation and Airway Epithelial Remodeling in a Murine Model of Allergic Asthma"; J Pharmacol Science, 108(3); pp. 355-363.
Naiserova et al. (2019) "(Meth)acrylate copolymers of Eudragit® type in oral tablet technology"; Ces.slov. Farm,;68; pp. 183-197.

* cited by examiner

COMPOSITIONS COMPRISING ENZYME-CLEAVABLE PRODRUGS AND CONTROLLED RELEASE NAFAMOSTAT AND METHODS OF USE THEREOF

CROSS-REFERENCE TO RELATED APPLICATION

This application is related to U.S. Provisional Patent Application Ser. No. 63/158,663 filed Mar. 9, 2021; the disclosure of which application is herein incorporated by reference.

INTRODUCTION

Drugs are susceptible to misuse, abuse, or overdose. Use of and access to these drugs therefore needs to be controlled. The control of access to the drugs is expensive to administer and can result in denial of treatment for patients that are not able to present themselves for dosing. For example, patients suffering from acute pain may be denied treatment with a pain drug unless they have been admitted to a hospital. Furthermore, control of use is often ineffective, leading to substantial morbidity and deleterious social consequences.

SUMMARY

Aspects of the present disclosure include pharmaceutical compositions, and their methods of use, where the pharmaceutical compositions include an active agent prodrug that provides enzymatically-controlled release of an active agent, and controlled release nafamostat or a pharmaceutically acceptable salt thereof.

Embodiments include compositions comprising a prodrug, wherein the prodrug comprises a drug covalently bound to a promoiety comprising a GI enzyme-cleavable moiety, wherein cleavage of the GI enzyme-cleavable moiety by a GI enzyme mediates release of the drug; and a controlled release composition of nafamostat or pharmaceutically acceptable salt thereof where nafamostat or pharmaceutically acceptable salt mediates enzymatically-controlled release of the drug from the prodrug following oral ingestion of the composition. Such cleavage can initiate, contribute to or effect drug release.

The embodiments include compositions and dose units wherein the prodrug is a compound of formula KC-(IIIa):

(KC-(IIIa))

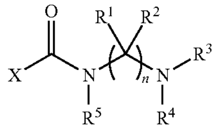

wherein:

X represents a residue of a ketone-containing opioid, wherein the hydrogen atom of the corresponding enolic group of the ketone is replaced by a covalent bond to $-C(O)-NR^5-(C(R^1)(R^2))_n-NR^3R^4$;

$R^5$ is selected from alkyl, substituted alkyl, arylalkyl, substituted arylalkyl, aryl and substituted aryl;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl, substituted cycloalkyl, aryl, or substituted aryl group, or two $R^2$ or $R^3$ groups on adjacent carbon atoms, together with the carbon atoms to which they are attached, form a cycloalkyl, substituted cycloalkyl, aryl, or substituted aryl group;

n is an integer from 2 to 6;

$R^3$ is hydrogen;

$R^4$ is

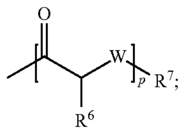

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;

each W is independently $-NR_8-$, $-O-$ or $-S-$;

each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

p is an integer from one to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The embodiments include compositions and dose units wherein the prodrug is a compound of formula KC-(IIIb):

(KC-(IIIb))

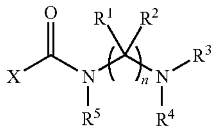

wherein:

X represents a residue of a ketone-containing opioid, wherein the hydrogen atom of the corresponding enolic group of the ketone is replaced by a covalent bond to $-C(O)-NR^5-(C(R^1)(R^2))_n-NR^3R^4$;

$R^5$ is selected from alkyl, substituted alkyl, arylalkyl, substituted arylalkyl, aryl and substituted aryl;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl or substituted cycloalkyl group, or two $R^1$ or $R^2$ groups on adjacent carbon atoms, together with the carbon atoms to which they are attached, form a cycloalkyl or substituted cycloalkyl group; n is an integer from 2 to 4;

$R^3$ is hydrogen;

$R^4$ is

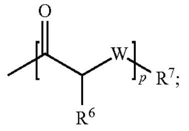

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;

each W is independently —$NR^8$—, —O— or —S—;

each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

p is an integer from one to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

In certain embodiments, compositions and dose units include the active agent prodrug of formula KC-8 (N-1-[3-(oxycodone-6-enol-carbonyl-methyl-amino)-2,2-dimethyl-propylamine]-arginine-glycine-malonic acid), shown below:

(KC-7)

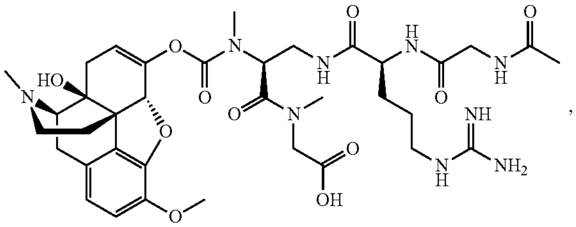

or acceptable salts, solvates, and hydrates thereof. Compound KC-7 is an active agent prodrug that provides controlled release of oxycodone.

In some embodiment, compositions and dose units include a prodrug compound of formula:

$$X—C(O)—NR^1—(C(R^2)(R^3))_n—NH—C(O)—CH(R^4)—NH(R^5) \quad (PC-(I))$$

or a pharmaceutically acceptable salt thereof, wherein:

X represents a residue of a phenolic opioid, wherein the hydrogen atom of the phenolic hydroxyl group is replaced by a covalent bond to —C(O)—$NR^1$—(C($R^2$)($R^3$))$_n$—NH—C(O)—CH($R^4$)—NH($R^5$);

$R^1$ represents a (1-4C)alkyl group;

$R^2$ and $R^3$ each independently represents a hydrogen atom or a (1-4C)alkyl group; n represents 2 or 3;

$R^4$ represents —$CH_2CH_2CH_2NH(C{=}NH)NH_2$ or —$CH_2CH_2CH_2CH_2NH_2$, the configuration of the carbon atom to which $R^4$ is attached corresponding with that in an L-amino acid; and $R^5$ represents a hydrogen atom, an N-acyl group, or a residue of an amino acid, a dipeptide, or an N-acyl derivative of an amino acid or dipeptide.

(KC-8)

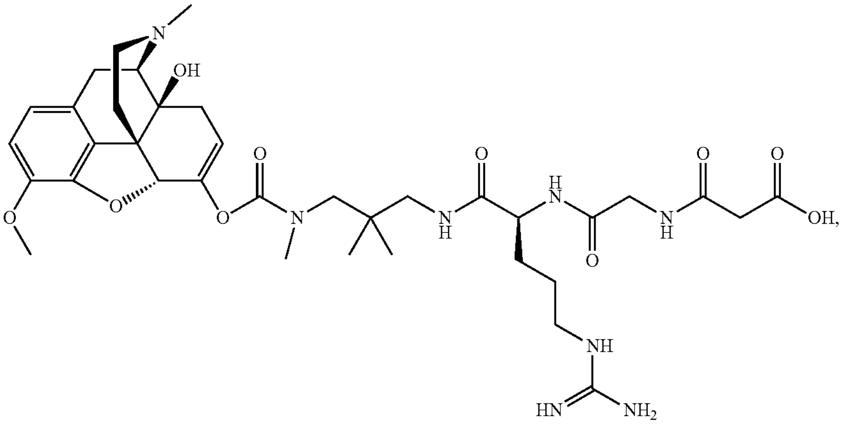

or acceptable salts, solvates, and hydrates thereof. Compound KC-8 is an active agent prodrug that provides controlled release of oxycodone.

In certain embodiments, compositions and dose units include the active agent prodrug of formula KC-7 (N-1-[(S)-2-(oxycodone-6-enol-carbonyl-methyl-amino)-2-carbonyl-sarcosine-ethyl amine]-arginine-glycine-acetate), shown below:

The embodiments include compositions and dose units wherein the prodrug is a compound of formula PC-(IIa):

$$X—C(O)—NR^1—(C(R^2)(R^3))_n—NH—C(O)—CH(R^4)—NH(R^5) \quad (PC-(IIa))$$

or a pharmaceutically acceptable salt thereof, wherein:

X represents a residue of a phenolic opioid, wherein the hydrogen atom of the phenolic hydroxyl group is replaced by a covalent bond to —C(O)—$NR^1$—(C($R^2$)($R^3$))$_n$—NH—C(O)—CH($R^4$)—NH($R^5$);

$R^1$ is selected from alkyl, substituted alkyl, arylalkyl, substituted arylalkyl, aryl and substituted aryl;

each $R^2$ is independently selected from hydrogen, alkyl, substituted alkyl, aryl, substituted aryl, acyl, and aminoacyl;

each $R^3$ is independently selected from hydrogen, alkyl, substituted alkyl, aryl, substituted aryl, acyl, and aminoacyl;

or $R^2$ and $R^3$ together with the carbon to which they are attached form a cycloalkyl, substituted cycloalkyl, aryl, or substituted aryl group, or two $R^2$ or $R^3$ groups on adjacent carbon atoms, together with the carbon atoms to which they are attached, form a cycloalkyl, substituted cycloalkyl, aryl, or substituted aryl group;

n represents an integer from 2 to 4;

$R^4$ represents —$CH_2CH_2CH_2NH(C{=}NH)NH_2$ or —$CH_2CH_2CH_2CH_2NH_2$, the configuration of the carbon atom to which $R^4$ is attached corresponding with that in an L-amino acid; and $R^5$ represents a hydrogen atom, an N-acyl group (including N-substituted acyl), a residue of an amino acid, a dipeptide, or an N-acyl derivative (including N-substituted acyl derivative) of an amino acid or dipeptide.

The embodiments include compositions and dose units wherein the prodrug is a compound of formula PC-(IIb):

$$X—C(O)—NR^1—(C(R^2)(R^3))_n—NH—C(O)—CH(R^4)—NH(R^5) \quad (PC-(IIb))$$

or a pharmaceutically acceptable salt thereof, wherein:

X represents a residue of a phenolic opioid, wherein the hydrogen atom of the phenolic hydroxyl group is replaced by a covalent bond to —C(O)—$NR^1$—(C($R^2$)($R^3$))$_n$—NH—C(O)—CH($R^4$)—NH($R^5$);

$R^1$ is selected from alkyl, substituted alkyl, arylalkyl, substituted arylalkyl, aryl and substituted aryl;

each $R^2$ is independently selected from hydrogen, alkyl, substituted alkyl, aryl, substituted aryl, acyl, and aminoacyl;

each $R^3$ is independently selected from hydrogen, alkyl, substituted alkyl, aryl, substituted aryl, acyl, and aminoacyl;

or $R^2$ and $R^3$ together with the carbon to which they are attached form a cycloalkyl or substituted cycloalkyl group, or two $R^2$ or $R^3$ groups on adjacent carbon atoms, together with the carbon atoms to which they are attached, form a cycloalkyl or substituted cycloalkyl group;

n represents an integer from 2 to 4;

$R^4$ represents —$CH_2CH_2CH_2NH(C{=}NH)NH_2$ or —$CH_2CH_2CH_2CH_2NH_2$, the configuration of the carbon atom to which $R^4$ is attached corresponding with that in an L-amino acid; and $R^5$ represents a hydrogen atom, an N-acyl group (including N-substituted acyl), a residue of an amino acid, a dipeptide, or an N-acyl derivative (including N-substituted acyl derivative) of an amino acid or dipeptide.

The embodiments include compositions and dose units wherein the prodrug is a compound of formula PC-(III):

$$X—C(O)—NR^1—(C(R^2)(R^3))_n—NH—C(O)—CH(R^4)—NH(R^5) \quad (PC-(III))$$

or pharmaceutically acceptable salt thereof, wherein:

X represents a residue of a phenolic opioid, wherein the hydrogen atom of the phenolic hydroxyl group is replaced by a covalent bond to —C(O)—$NR^1$—(C($R^2$)($R^3$))$_n$—NH—C(O)—CH($R^4$)—NH($R^5$);

$R^1$ represents a (1-4C)alkyl group;

$R^2$ and $R^3$ each independently represents a hydrogen atom or a (1-4C)alkyl group;

n represents 2 or 3;

$R^4$ represents —$CH_2CH_2CH_2NH(C{=}NH)NH_2$ or —$CH_2CH_2CH_2CH_2NH_2$, the configuration of the carbon atom to which $R^4$ is attached corresponding with that in an L-amino acid; and $R^5$ represents a hydrogen atom, an N-acyl group (including N-substituted acyl), a residue of an amino acid, a dipeptide, or an N-acyl derivative (including N-substituted acyl derivative) of an amino acid or dipeptide.

In certain embodiments, compositions and dose units include the active agent prodrug hydromorphone 3-(N-methyl-N-(2-N'-acetylarginylamino))ethylcarbamate, or a pharmaceutically acceptable salt thereof. In certain embodiments, compositions and dose units include the active agent prodrug oxymorphone 3-(N-methyl-N-(2-N'-acetylarginylamino))ethylcarbamate, or a pharmaceutically acceptable salt thereof. In certain embodiments, compositions and dose units include the active agent prodrug morphine 3-(N-methyl-N-(2-N'-acetylarginylamino))ethylcarbamate, or a pharmaceutically acceptable salt thereof.

The embodiments include compositions and dose units wherein the prodrug is a compound of formula AM-(I):

AM-(I)

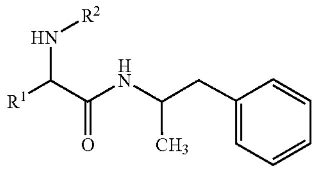

wherein $R^1$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl; and $R^2$ is an acyl, substituted acyl, or an N-acyl derivative of a peptide;

or a salt, hydrate or solvate thereof.

The embodiments include compositions and dose units wherein the prodrug is a compound of formula AM-(II):

AM-(II)

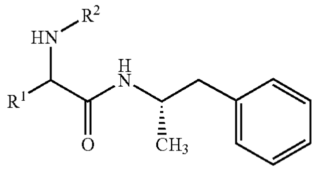

wherein $R^1$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl; and $R^2$ is an acyl, substituted acyl, or an N-acyl derivative of a peptide;

or a salt, hydrate or solvate thereof.

In certain embodiments, compositions and dose units include the active agent prodrug of formula AM-1 (Amphetamine-arginine-acetate), shown below:

Compound AM-1

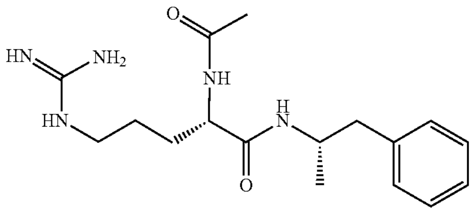

or a salt, hydrate or solvate thereof.

In certain embodiments, compositions and dose units include the active agent prodrug of formula AM-2 (Amphetamine-arginine-malonate), shown below:

Compound AM-2

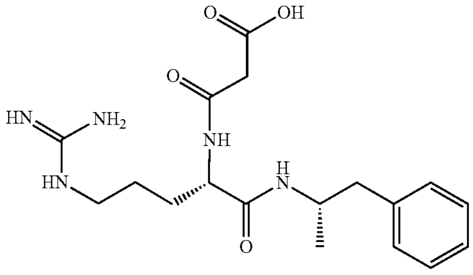

or a salt, hydrate or solvate thereof.

In certain embodiments, compositions and dose units include the active agent prodrug of formula AM-5 (Amphetamine-lysine-acetate), shown below:

Compound AM-5

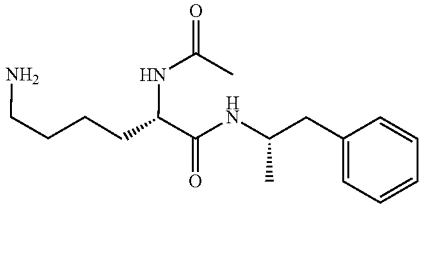

or a salt, hydrate or solvate thereof.

In certain embodiments, compositions and dose units include the active agent prodrug of formula AM-9 (Amphetamine-arginine-glycine-acetate), shown below:

(AM-9)

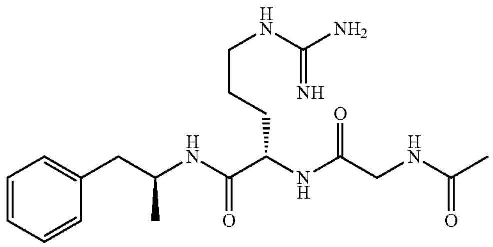

, or a salt, hydrate or solvate thereof.

In certain embodiments, compositions and dose units include the active agent prodrug of formula AM-10 (Amphetamine-arginine-alanine-acetate), shown below:

(AM-10)

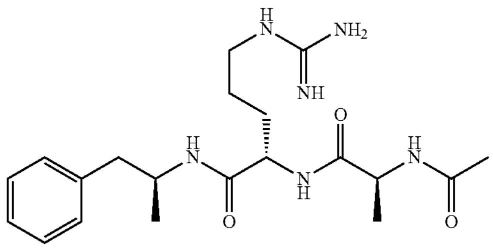

, or a salt, hydrate or solvate thereof.

The embodiments include compositions and dose units wherein the prodrug is a compound of formula HC-(I):

HC-(I)

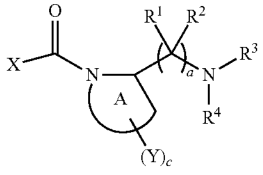

wherein

X is selected from a residue of a ketone-containing active agent, wherein the hydrogen atom of the corresponding hydroxyl group of the enolic tautomer of the ketone is replaced by a covalent bond to $-C(O)-N[(A\ ring)-Y_c]-(CR^1R^2)_a-NH-C(O)-CH(R^5)-N(R^3)-[C(O)-CH(R^6)-N(R^3)]_b-R^7$; a residue of a phenolic active agent, wherein the hydrogen atom of the phenolic hydroxyl group is replaced by a covalent bond to $-C(O)-N[(A\ ring)-Y_c]-(CR^1R^2)_a-NH-C(O)-CH(R^5)-N(R^3)-[C(O)-CH(R^6)-N(R^3)]_b-R^7$; and a residue of an amide-containing active agent, wherein $-C(O)-N[(A\ ring)-Y_c]-(CR^1R^2)_a-NH-C(O)-CH(R^5)-N(R^3)-[C(O)-CH(R^6)-N(R^3)]_b-R^7$ is connected to the amide-containing active agent through the oxygen of the amide group, wherein the amide group is converted to an amide enol or an imine tautomer;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each $R^3$ is independently hydrogen, alkyl, substituted alkyl, aryl or substituted aryl;

$R^4$ is

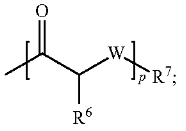

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;

each W is independently —$NR^8$—, —O— or —S—;

each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

p is an integer from one to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The embodiments include compositions and dose units wherein the prodrug is a compound of formula HC-(II):

HC-(II)

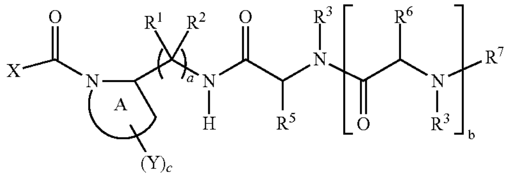

wherein

X is selected from a residue of a ketone-containing opioid, wherein the hydrogen atom of the corresponding hydroxyl group of the enolic tautomer of the ketone is replaced by a covalent bond to —C(O)—N[(A ring)-$Y_c$]—$(CR^1R^2)_a$—NH—C(O)—$CH(R^5)$—$N(R^3)$—[C(O)—$CH(R^6)$—$N(R^3)$]$_b$—$R^7$; a residue of a phenolic opioid, wherein the hydrogen atom of the phenolic hydroxyl group is replaced by a covalent bond to —C(O)—N[(A ring)-$Y_c$]—$(CR^1R^2)_a$—NH—C(O)—$CH(R^5)$—$N(R^3)$—[C(O)—$CH(R^6)$—$N(R^3)$]$_b$—$R^7$; and a residue of an amide-containing opioid, wherein —C(O)—N[(A ring)-$Y_c$]—$(CR^1R^2)_a$—NH—C(O)—$CH(R^5)$—$N(R^3)$—[C(O)—$CH(R^6)$—$N(R^3)$]$_b$—$R^7$ is connected to the amide-containing opioid through the oxygen of the amide group, wherein the amide group is converted to an amide enol or an imine tautomer;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8;

each $R^3$ is independently hydrogen, alkyl, substituted alkyl, aryl or substituted aryl;

$R^5$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

b is a number from zero to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

Aspects of the present disclosure include oral compositions of nafamostat or a pharmaceutically acceptable salt thereof where the composition provides for controlled release of the nafamostat or pharmaceutically acceptable salt thereof to a subject for an extended period of time. In some embodiments, the oral composition of nafamostat or a pharmaceutically acceptable salt thereof includes a plurality of controlled release beads where each bead includes a core, an active agent layer having nafamostat or a pharmaceutically acceptable salt thereof and a controlled release layer having one or more polymers formulated in an amount sufficient to provide for controlled release of the nafamostat or pharmaceutically acceptable salt thereof. In some embodiments, the plurality of controlled release nafamostat beads are encapsulated in a capsule. In certain embodiments, the capsule further includes one or more of the active agent prodrugs as described above.

In some embodiments, the core of each controlled release nafamostat bead is formed from one or more polysaccharides. In some instances, the core is formed from a cellulose polymer. In certain instances, the core is formed from microcrystalline cellulose.

In some embodiments, the active agent layer includes nafamostat or a pharmaceutically acceptable salt thereof. In some instances, the active agent layer includes nafamostat free base.

In some instances, the active agent layer includes a pharmaceutically acceptable salt of nafamostat. In certain instances, the active agent layer includes nafamostat mesylate.

In some embodiments, the active agent layer includes a binder. In some instances, the binder is a water-soluble film-forming polymer. In certain instances, the soluble film-forming polymer is a polysaccharide, such as a water-soluble cellulose polymer. In certain embodiments, the active agent layer includes hydroxypropylmethylcellulose.

The controlled release layer can include one or more acrylate polymers, methacrylate polymers, a copolymer of one or more acrylate polymers or methacrylate polymers or a combination thereof. In some embodiments, the controlled release layer includes an acrylate copolymer formed from monomers of ethylacrylate, methyl-methacrylate and chlorotrimethyl-ammonioethyl methacrylate. In certain instances, the controlled release layer includes poly(ethylacrylate, methyl-methacrylate and chlorotrimethyl-ammonioethyl methacrylate). The poly(ethylacrylate, methylmethacrylate and chlorotrimethyl-ammonioethyl methacrylate) can contain different amounts of quaternary ammonium groups, for example, about 50 mEq of quaternary ammonium groups per 100 g of polymer (acrylate copolymer A) or about 25 mEq of quaternary ammonium groups per 100 g of polymer (acrylate copolymer B). Beads containing controlled release layers having different ratios of acrylate copolymer B and acrylate copolymer A are provided. For example, the controlled release layer can contain between 5% and 100% of acrylate copolymer B and between 5% and 100% of acrylate copolymer A. In certain embodiments, the controlled release layer includes a ratio of acrylate copolymer B to acrylate copolymer A of 80:20, such as a ratio of acrylate copolymer B to acrylate copolymer A of 87:13, such as a ratio of acrylate copolymer B to acrylate copolymer A of 90:10, such as a ratio of acrylate copolymer B to acrylate copolymer A of 92:8 and including a ratio of acrylate copolymer B to acrylate copolymer A of 95:5.

In certain embodiments, compositions of interest can further comprise nafamostat or a pharmaceutically acceptable salt thereof in an immediate release form that provides for immediate release of the nafamostat or pharmaceutically acceptable salt thereof to a subject. In some instances, immediate release nafamostat or pharmaceutically acceptable salt thereof is present in the oral composition as a powder or granulate. In some instances, immediate release nafamostat or pharmaceutically acceptable salt thereof is present in the oral composition as an immediate release layer coated on top of the controlled release layer of the plurality of beads.

In some embodiments, orally administering the controlled release nafamostat composition is sufficient to provide for sustained release of one or more doses of nafamostat or a pharmaceutically acceptable salt thereof to the subject over an extended period of time, such as for 12 hours or longer, including for 24 hours or longer. In some instances, orally administering the composition is sufficient to provide for a delayed immediate release of one or more doses of nafamostat or a pharmaceutically acceptable salt thereof to the subject. In certain instances, orally administering the composition is sufficient to provide an immediate dose of the nafamostat or a pharmaceutically acceptable salt thereof to the subject followed by sustained release of nafamostat or a pharmaceutically acceptable salt thereof to the subject over an extended period of time. In certain instances, orally administering the composition is sufficient to provide a first immediate dose of the nafamostat or a pharmaceutically acceptable salt thereof to the subject followed by a second immediate release dose of the nafamostat or a pharmaceutically acceptable salt thereof to the subject at a predetermined time after the first immediate dose.

Aspects of the present disclosure also include methods for orally administering to a subject in need thereof an active agent prodrug and one or more of the controlled release nafamostat compositions described herein. In some instances, the active agent prodrug is administered simultaneously with the controlled release nafamostat composition. In other instances, the active agent prodrug and the controlled release nafamostat composition are administered sequentially. In some cases, the controlled release nafamostat composition is orally administered to the subject a predetermined period of time before administering the active agent prodrug. In some cases, the controlled release nafamostat composition is orally administered to the subject a predetermined period of time after administering the active agent prodrug.

The embodiments of the present disclosure provide for improved patient compliance with a therapy prescribed by a clinician comprising directing administration of any of the compositions or dose units described herein to a patient in need thereof. Such embodiments can provide for improved patient compliance with a prescribed therapy as compared to patient compliance with a prescribed therapy using drug and/or using prodrug without the controlled release nafamostat or pharmaceutically acceptable salt thereof as compared to prodrug with the controlled release nafamostat or pharmaceutically acceptable salt thereof. The embodiments also provide for reduced risk of unintended overdose of a drug comprising directing administration of any of the pharmaceutical compositions or dose units described herein to a patient in need of treatment.

The embodiments also include methods of making a dose unit comprising combining an active agent prodrug and a controlled release nafamostat composition in a dose unit, wherein the active agent prodrug and controlled release nafamostat composition are present in the dose unit in an amount effective to attenuate release of the drug from the prodrug.

DEFINITIONS

Figure 1:
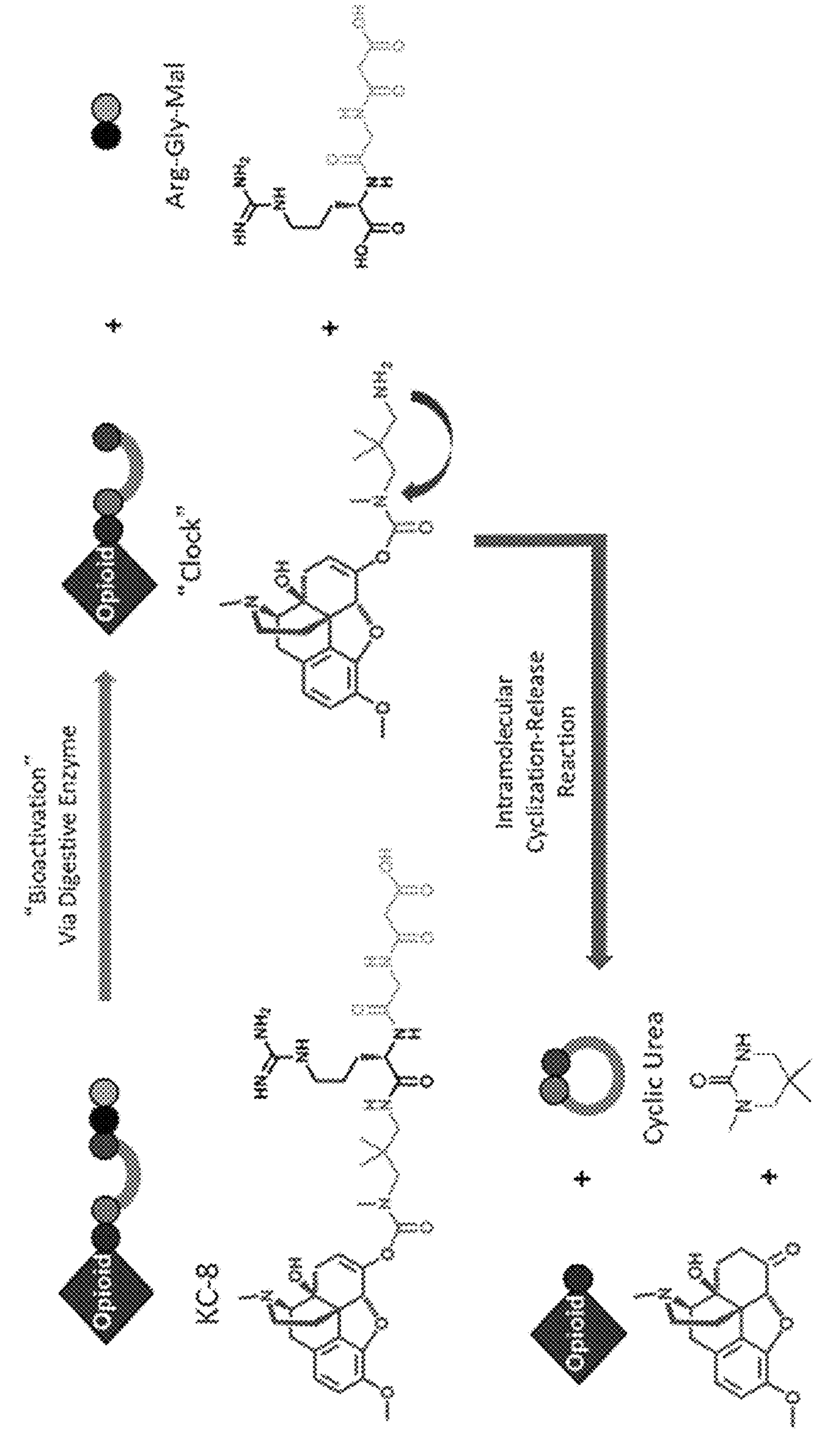
FIG. 1 shows a biochemical mechanism wherein an oxycodone derivative is converted into active oxycodone by action of a digestive enzyme such as trypsin.

The following terms have the following meaning unless otherwise indicated. Any undefined terms have their art recognized meanings.

As used herein, the term "alkyl" by itself or as part of another substituent refers to a saturated branched or straight-chain monovalent hydrocarbon radical derived by the removal of one hydrogen atom from a single carbon atom of a parent alkane. Typical alkyl groups include, but are not limited to, methyl; ethyl, propyls such as propan-1-yl or propan-2-yl; and butyls such as butan-1-yl, butan-2-yl, 2-methyl-propan-1-yl or 2-methyl-propan-2-yl. In some embodiments, an alkyl group comprises from 1 to 20 carbon atoms. In other embodiments, an alkyl group comprises from 1 to 10 carbon atoms. In still other embodiments, an alkyl group comprises from 1 to 6 carbon atoms, such as from 1 to 4 carbon atoms.

"Alkanyl" by itself or as part of another substituent refers to a saturated branched, straight-chain or cyclic alkyl radical derived by the removal of one hydrogen atom from a single carbon atom of an alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkylene" refers to a branched or unbranched saturated hydrocarbon chain, usually having from 1 to 40 carbon atoms, more usually 1 to 10 carbon atoms and even more usually 1 to 6 carbon atoms. This term is exemplified by groups such as methylene ($-CH_2-$), ethylene ($-CH_2CH_2-$), the propylene isomers (e.g., $-CH_2CH_2CH_2-$ and $-CH(CH_3)CH_2-$) and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of an alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of an alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical $-C(O)R^{30}$, where $R^{31}$ is hydrogen, alkyl, cycloalkyl, cycloheteroalkyl, aryl, arylalkyl, heteroalkyl, heteroaryl, heteroarylalkyl as defined herein and substituted versions thereof. Representative examples include, but are not limited to formyl, acetyl, cyclohexylcarbonyl, cyclohexylmethylcarbonyl, benzoyl, benzylcarbonyl, piperonyl, propionyl, succinyl, and malonyl, and the like.

The term "aminoacyl" refers to the group —C(O)$NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Alkoxy" by itself or as part of another substituent refers to a radical —$OR^{31}$ where $R^{31}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent refers to a radical —C(O)$OR^{31}$ where $R^{31}$ represents an alkyl or cycloalkyl group as defined herein. Representative examples include, but are not limited to, methoxycarbonyl, ethoxycarbonyl, propoxycarbonyl, butoxycarbonyl, cyclohexyloxycarbonyl and the like.

"Aryl" by itself or as part of another substituent refers to a monovalent aromatic hydrocarbon radical derived by the removal of one hydrogen atom from a single carbon atom of an aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group comprises from 6 to 20 carbon atoms. In certain embodiments, an aryl group comprises from 6 to 12 carbon atoms. Examples of an aryl group are phenyl and naphthyl.

"Arylalkyl" by itself or as part of another substituent refers to an acyclic alkyl radical in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In certain embodiments, an arylalkyl group is ($C_7$-$C_{30}$) arylalkyl, e.g., the alkanyl, alkenyl or alkynyl moiety of the arylalkyl group is ($C_1$-$C_{10}$) and the aryl moiety is ($C_6$-$C_{20}$). In certain embodiments, an arylalkyl group is ($C_7$-$C_{20}$) arylalkyl, e.g., the alkanyl, alkenyl or alkynyl moiety of the arylalkyl group is ($C_1$-$C_8$) and the aryl moiety is ($C_6$-$C_{12}$).

"Arylaryl" by itself or as part of another substituent, refers to a monovalent hydrocarbon group derived by the removal of one hydrogen atom from a single carbon atom of a ring system in which two or more identical or non-identical aromatic ring systems are joined directly together by a single bond, where the number of such direct ring junctions is one less than the number of aromatic ring systems involved. Typical arylaryl groups include, but are not limited to, biphenyl, triphenyl, phenyl-napthyl, binaphthyl, biphenyl-napthyl, and the like. When the number of carbon atoms in an arylaryl group are specified, the numbers refer to the carbon atoms comprising each aromatic ring. For example, ($C_5$-$C_{14}$) arylaryl is an arylaryl group in which each aromatic ring comprises from 5 to 14 carbons, e.g., biphenyl, triphenyl, binaphthyl, phenylnapthyl, etc. In certain embodiments, each aromatic ring system of an arylaryl group is independently a ($C_5$-$C_{14}$) aromatic. In certain embodiments, each aromatic ring system of an arylaryl group is independently a ($C_5$-$C_{10}$) aromatic. In certain embodiments, each aromatic ring system is identical, e.g., biphenyl, triphenyl, binaphthyl, trinaphthyl, etc.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. In certain embodiments, the cycloalkyl group is ($C_3$-$C_{10}$) cycloalkyl. In certain embodiments, the cycloalkyl group is ($C_3$-$C_7$) cycloalkyl.

"Cycloheteroalkyl" or "heterocyclyl" by itself or as part of another substituent, refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine and the like.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —S—S—, —O—S—, —$NR^{37}R^{38}$—, =N—N=, —N=N—, —N=N—$NR^{39}R^{40}$, —$PR^{41}$—, —$P(O)_2$—, —$POR^{42}$—, —O—$P(O)_2$—, —S—O—, —S—(O)—, —$SO_2$—, —$SnR^{43}R^{44}$— and the like, where $R^{37}$, $R^{38}$, $R^{39}$, $R^{40}$, $R^{41}$, $R^{42}$, $R^{43}$ and $R^{44}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent, refers to an acyclic alkyl radical in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl and/or heterorylalkynyl is used. In certain embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl. In certain embodiments, the heteroarylalkyl group is 6-20 membered heteroarylalkyl, e.g., the alkanyl, alkenyl or alkynyl moiety of the heteroarylalkyl is 1-8 membered and the heteroaryl moiety is a 5-12-membered heteroaryl.

"Aromatic Ring System" by itself or as part of another substituent, refers to an unsaturated cyclic or polycyclic ring system having a conjugated $\pi$ electron system. Specifically included within the definition of "aromatic ring system" are fused ring systems in which one or more of the rings are aromatic and one or more of the rings are saturated or unsaturated, such as, for example, fluorene, indane, indene, phenalene, etc. Typical aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Heteroaromatic Ring System" by itself or as part of another substituent, refers to an aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical heteroaromatic ring systems include, but are not limited to, arsindole, carbazole, 3-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Substituted" refers to a group in which one or more hydrogen atoms are independently replaced with the same or different substituent(s). Typical substituents include, but are not limited to, alkylenedioxy (such as methylenedioxy), -M, $—R^{60}$, $—O^-$, $=O$, $—OR^{60}$, $—SR^{60}$, $—S^-$, $=S$, $—NR^{60}R^{61}$, $=NR^{60}$, $—CF_3$, —CN, —OCN, —SCN, —NO, $—NO_2$, $=N_2$, $—N_3$, $—S(O)_2O^-$, $—S(O)_2OH$, $—S(O)_2R^{60}$, $—OS(O)_2O^-$, $—OS(O)_2R^{60}$, $—P(O)(O^-)_2$, $—P(O)(OR^{60})(O^-)$, $—OP(O)(OR^{60})(OR^{61})$, $—C(O)R^{60}$, $—C(S)R^{60}$, $—C(O)OR^{60}$, $—C(O)NR^{60}R^{61}$, —C(O)O—, $—C(S)OR^{60}$, $—NR^{62}C(O)NR^{6}OR^{61}$, $—NR^{62}C(S)NR^{60}R^{61}$, $—NR^{62}C(NR^{63})NR^{6}OR^{61}$ and $—C(NR^{62})NR^{60}R^{61}$ where M is halogen; $R^{60}$, $R^{61}$, $R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring; and $R^{64}$ and $R^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally $R^{64}$ and $R^{65}$ together with the nitrogen atom to which they are bonded form a cycloheteroalkyl or substituted cycloheteroalkyl ring. In certain embodiments, substituents include -M, $—R^{60}$, $=O$, $—OR^{60}$, $—SR^{60}$, $—S^-$, $=S$, $—NR^{60}R^{61}$, $NR^{60}$, $—CF_3$, —CN, —OCN, —SCN, —NO, $—NO_2$, $=N_2$, $—N_3$, $—S(O)_2R^{60}$, $—OS(O)_2O^-$, $—OS(O)_2R^{60}$, $—P(O)(O^-)_2$, $—P(O)(OR^{60})(O^-)$, $—OP(O)(OR^{60})(OR^{61})$, $—C(O)R^{60}$, $—C(S)R^{60}$, $—C(O)OR^{60}$, $—C(O)NR^{60}R^{61}$, —C(O)O—, $—NR^{62}C(O)NR^{60}R^{61}$. In certain embodiments, substituents include -M, $—R^{60}$, $=O$, $—OR^{60}$, $—SR^{60}$, $—NR^{60}R^{61}$, $—CF_3$, —CN, $—NO_2$, $—S(O)_2R^{60}$, $—P(O)(OR^{60})(O^-)$, $—OP(O)(OR^{60})(OR^{61})$, $—C(O)R^{60}$, $—C(O)OR^{60}$, $—C(O)NR^{60}R^{61}$, —C(O)O. In certain embodiments, substituents include -M, $—R^{60}$, $=O$, $—OR^{60}$, $—SR^{60}$, $—NR^{60}R^{61}$, $—CF_3$, —CN, $—NO_2$, $—S(O)_2R^{60}$, $—OP(O)(OR^{60})(OR^{61})$, $—C(O)R^{60}$, $—C(O)OR^{60}$, $—C(O)O^-$, where $R^{60}$, $R^{61}$ and $R^{62}$ are as defined above. For example, a substituted group may bear a methylenedioxy substituent or one, two, or three substituents selected from a halogen atom, a (1-4C)alkyl group and a (1-4C)alkoxy group.

"Dose unit" as used herein refers to a combination of a GI enzyme-cleavable prodrug (e.g., trypsin-cleavable prodrug) and a GI enzyme inhibitor (e.g., a trypsin inhibitor). A "single dose unit" is a single unit of a combination of a GI enzyme-cleavable prodrug (e.g., trypsin-cleavable prodrug) and a GI enzyme inhibitor (e.g., trypsin inhibitor), where the single dose unit provide a therapeutically effective amount of drug (i.e., a sufficient amount of drug to effect a therapeutic effect, e.g., a dose within the respective drug's therapeutic window, or therapeutic range). "Multiple dose units" or "multiples of a dose unit" or a "multiple of a dose unit" refers to at least two single dose units.

"PK profile" refers to a profile of drug concentration in blood or plasma. Such a profile can be a relationship of drug concentration over time (i.e., a "concentration-time PK profile") or a relationship of drug concentration versus number of doses ingested (i.e., a "concentration-dose PK profile"). A PK profile is characterized by PK parameters.

"PK parameter" refers to a measure of drug concentration in blood or plasma, such as: 1) "drug Cmax", the maximum concentration of drug achieved in blood or plasma; 2) "drug Tmax", the time elapsed following ingestion to achieve Cmax; and 3) "drug exposure", the total concentration of drug present in blood or plasma over a selected period of time, which can be measured using the area under the curve (AUC) of a time course of drug release over a selected period of time (t). Modification of one or more PK parameters provides for a modified PK profile.

"Pharmacodynamic (PD) profile" refers to a profile of the efficacy of a drug in a patient (or subject or user), which is characterized by PD parameters. "PD parameters" include "drug Emax" (the maximum drug efficacy), "drug EC50" (the concentration of drug at 50% of the Emax) and side effects.

"Gastrointestinal enzyme" or "GI enzyme" refers to an enzyme located in the gastrointestinal (GI) tract, which encompasses the anatomical sites from mouth to anus. Trypsin is an example of a GI enzyme.

"Gastrointestinal enzyme-cleavable moiety" or "GI enzyme-cleavable moiety" refers to a group comprising a site susceptible to cleavage by a GI enzyme. For example, a "trypsin-cleavable moiety" refers to a group comprising a site susceptible to cleavage by trypsin.

"Gastrointestinal enzyme inhibitor" or "GI enzyme inhibitor" refers to any agent capable of inhibiting the action of a gastrointestinal enzyme on a substrate. The term also encompasses salts of gastrointestinal enzyme inhibitors. For example, a "trypsin inhibitor" refers to any agent capable of inhibiting the action of trypsin on a substrate.

"Pharmaceutical composition" refers to at least one compound and can further comprise a pharmaceutically acceptable carrier, with which the compound is administered to a patient.

"Pharmaceutically acceptable salt" refers to a salt of a compound, which possesses the desired pharmacological activity of the compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

The term "solvate" as used herein refers to a complex or aggregate formed by one or more molecules of a solute, e.g. a prodrug or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

"Pharmaceutically acceptable carrier" refers to a diluent, adjuvant, excipient or vehicle with, or in which a compound is administered.

"Preventing" or "prevention" or "prophylaxis" refers to a reduction in risk of occurrence of a condition, such as pain.

"Prodrug" refers to a derivative of an active agent that requires a transformation within the body to release the active agent. In certain embodiments, the transformation is an enzymatic transformation. Prodrugs are frequently, although not necessarily, pharmacologically inactive until converted to the active agent.

"Promoiety" refers to a form of protecting group that when used to mask a functional group within an active agent converts the active agent into a prodrug. Typically, the promoiety will be attached to the drug via bond(s) that are cleaved by enzymatic or non-enzymatic means in vivo.

"Treating" or "treatment" of any condition, such as pain, refers, in certain embodiments, to ameliorating the condition (i.e., arresting or reducing the development of the condition). In certain embodiments "treating" or "treatment" refers to ameliorating at least one physical parameter, which may not be discernible by the patient. In certain embodiments, "treating" or "treatment" refers to inhibiting the condition, either physically, (e.g., stabilization of a discernible symptom), physiologically, (e.g., stabilization of a physical parameter), or both. In certain embodiments, "treating" or "treatment" refers to delaying the onset of the condition.

"Therapeutically effective amount" means the amount of a compound (e.g. prodrug) that, when administered to a patient for preventing or treating a condition such as pain, is sufficient to effect such treatment. The "therapeutically effective amount" will vary depending on the compound, the condition and its severity and the age, weight, etc., of the patient.

DETAILED DESCRIPTION

Aspects of the present disclosure include pharmaceutical compositions, and their methods of use, where the pharmaceutical compositions include an active agent prodrug that provides enzymatically-controlled release of an active agent, and controlled release nafamostat or a pharmaceutically acceptable salt thereof.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

As used herein, the singular forms "a", "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," "comprise," "consisting essentially of," "consists essentially of," "consisting," and "consists" can be used interchangeably.

The term "about" or "approximately" means within an acceptable error range for the particular value as determined by one of ordinary skill in the art, which will depend in part on how the value is measured or determined, i.e., the limitations of the measurement system. In the context of compositions containing amounts of ingredients where the terms "about" or "approximately" are used, these compositions contain the stated amount of the ingredient with a variation (error range) of 0-10% around the value (X±10%).

In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

Active Agent Prodrugs

As summarized above, aspects of the present disclosure include active agent prodrugs that provide enzymatically-controlled release of an active agent, and controlled release nafamostat or a pharmaceutically acceptable salt thereof. In some embodiments, the active agent prodrugs include opioid prodrugs. In some embodiments, the active agent prodrugs include amphetamine prodrugs. An "opioid" refers to a chemical substance that exerts its pharmacological action by interaction at an opioid receptor. An opioid can be a natural product, a synthetic compound or a semi-synthetic compound. In certain embodiments, an opioid is a compound with a pharmacophore that presents to the opioid receptor an aromatic group and an aliphatic amine group in an architecturally discrete way. See, for example, Foye's Principles of Medicinal Chemistry, Sixth Edition, ed. T. L. Lemke and D. A. Williams, Lippincott Williams & Wilkins, 2008, particularly Chapter 24, pages 653-678.

The disclosure provides an opioid prodrug which provides enzymatically-controlled release of an opioid. The disclosure provides a promoiety that is attached to an opioid through any structural moiety on the opioid, where the structural moiety has a reactive group. Any type of reactive group on an opioid can provide a handle for a point of attachment to a promoiety. Examples of reactive groups on an opioid include, but are not limited to, alcohol (such as phenol), ketone, amino, and amide. An alcohol (such as a phenol) on an opioid can provide a point of attachment to a promoiety by reaction to form a linkage, such as a carbamate, an ether, or an ester. A ketone on an opioid can provide a point of attachment to a promoiety by reaction to form a linkage, such as an enol carbamate. An amino group on an opioid can provide a point of attachment to a promoiety by reaction to form an amino linkage, including quaternary salts, or an amide. An amide on an opioid can provide a point of attachment to a promoiety by reaction to form a linkage, such as an amide enol or an N-acylated amide.

An alcohol-containing (such as a phenol-containing) opioid refers to a subset of the opioids that contain alcohol (such as a phenol) group. A phenolic opioid refers to a subset of the opioids that contain a phenol group. For instance, the following opioids contain an alcohol (such as a phenol group) that can be a point of attachment to a promoiety: buprenorphine, dihydroetorphine, diprenorphine, etorphine, hydromorphone, levorphanol, morphine, nalmefene, naloxone, N-methyldiprenorphine, N-methylnaloxone, naltrexone, N-methylnaltexone, oxymorphone, oripavine, ketobemidone, dezocine, pentazocine, phenazocine, butorphanol, nalbuphine, meptazinol, o-desmethyltramadol, tapentadol, and nalorphine. The following opioids also contain an alcohol (such as a phenol) that can be a point of attachment to a promoiety: benzylmorphine, codeine, dihydrocodeine, dihydromorphine, ethylmorphine, loperamide, methyldihydromorphine, normorphine, N-methylnalmefene, olmefentanyl, oxycodone, pentamorphone, pholcodine, and tramadol.

A ketone-containing opioid refers to a subset of the opioids that contain a ketone group. For instance, the following opioids contain a ketone group that can be a point of attachment to a promoiety: acetylmorphone, hydrocodone, hydromorphone, ketobemidone, methadone, naloxone, N-methylnaloxone, naltrexone, N-methylnaltrexone, oxycodone, oxymorphone, and pentamorphone.

Phenol-Modified Opioid Prodrugs

The disclosure provides a phenol-modified opioid prodrug which provides enzymatically-controlled release of a phenolic opioid. In a phenol-modified opioid prodrug, a promoiety is attached to the phenolic opioid via modification of the phenol moiety. A phenol-modified opioid prodrug can also be referred to as a phenolic opioid prodrug. In a phenol-modified opioid prodrug, the hydrogen atom of the phenolic hydroxyl group of the phenolic opioid is replaced by a covalent bond to a promoiety.

As disclosed herein, a gastrointestinal (GI) enzyme-cleavable phenol-modified opioid prodrug is a phenol-modified opioid prodrug that comprises a promoiety comprising a GI enzyme-cleavable moiety having a site susceptible to cleavage by a GI enzyme. Such a prodrug comprises a phenolic opioid covalently bound to a promoiety comprising a GI enzyme-cleavable moiety, wherein cleavage of the GI enzyme-cleavable moiety by the GI enzyme mediates release of the drug. Cleavage can initiate, contribute to or effect drug release.

Phenol-Modified Opioid Prodrugs with Promoiety Comprising Cyclizable Spacer Leaving Group and Cleavable Moiety According to certain embodiments, there is provided a phenol-modified opioid prodrug which provides enzymatically-controlled release of a phenolic opioid. The disclosure provides for a phenol-modified opioid prodrug in which the promoiety comprises a cyclizable spacer leaving group and a cleavable moiety. In certain embodiments, the phenol-modified opioid prodrug is a corresponding compound in which the phenolic hydrogen atom has been substituted with a spacer leaving group bearing a nitrogen nucleophile that is protected with an enzymatically-cleavable moiety, the configuration of the spacer leaving group and nitrogen nucleophile being such that, upon enzymatic cleavage of the cleavable moiety, the nitrogen nucleophile is capable of forming a cyclic urea, liberating the compound from the spacer leaving group so as to provide a phenolic opioid.

The enzyme capable of cleaving the enzymatically-cleavable moiety may be a peptidase, also referred to as a protease—the promoiety comprising the enzymatically-cleavable moiety being linked to the nucleophilic nitrogen through an amide (e.g. a peptide: —NHC(O)—) bond. In some embodiments, the enzyme is a digestive enzyme of a protein.

The corresponding prodrug provides post administration-activated, controlled release of the phenolic opioid. The prodrug requires enzymatic cleavage to initiate release of the phenolic opioid and thus the rate of release of the phenolic opioid depends upon both the rate of enzymatic cleavage and the rate of cyclization. Accordingly, the prodrug has reduced susceptibility to accidental overdosing or abuse, whether by deliberate overdosing, administration through an inappropriate route, such as by injection, or by chemical modification using readily available household chemicals. The prodrug is configured so that it will not provide excessively high plasma levels of the active drug if it is administered inappropriately, and cannot readily be decomposed to afford the active drug other than by enzymatic cleavage followed by controlled cyclization.

The enzyme-cleavable moiety linked to the nitrogen nucleophile through an amide bond can be, for example, a residue of an amino acid or a peptide, or an (alpha)N-acyl derivative of an amino acid or peptide (for example an N-acyl derivative of a pharmaceutically acceptable carboxylic acid). The peptide can contain, for example, up to about 100 amino acid residues. Each amino acid can advantageously be a naturally occurring amino acid, such as an L-amino acid. Examples of naturally occurring amino acids are alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine. Accordingly, examples of enzyme-cleavable moieties include residues of the L-amino acids listed hereinabove and N-acyl derivatives thereof, and peptides formed from at least two of the L-amino acids listed hereinabove, and the N-acyl derivatives thereof.

The cyclic group formed when the phenolic opioid is released is conveniently pharmaceutically acceptable, in particular a pharmaceutically acceptable cyclic urea. It will be appreciated that cyclic ureas are generally very stable and have low toxicity.

In embodiments, the phenolic opioid may include, but is not limited to buprenorphine, dihydroetorphine, diprenorphine, etorphine, hydromorphone, levorphanol, morphine, nalbuphine, nalmefene, nalorphine, naloxone, naltrexone, N-methyldiprenorphine, N-methylnaloxone, N-methylnaltrexone, oripavine, oxymorphone, butorphanol, dezocine, ketobemidone, meptazinol, o-desmethyltramadol, pentazocine, phenazocine, and tapentadol.

Formula PC-(I)

According to one aspect, the embodiments include pharmaceutical compositions, which comprise a compound of general formula PC-(I):

$$X—C(O)—NR^1—(C(R^2)(R^3))_n—NH—C(O)—CH(R^4)—NH(R^5) \quad (PC-(I))$$

or a pharmaceutically acceptable salt thereof, in which.

X represents a residue of a phenolic opioid, wherein the hydrogen atom of the phenolic hydroxyl group is replaced by a covalent bond to $—C(O)—NR^1—(C(R^2)(R^3))_n—NH—C(O)—CH(R^4)—NH(R^5)$;

$R^1$ represents a (1-4C)alkyl group;

$R^2$ and $R^3$ each independently represents a hydrogen atom or a (1-4C)alkyl group;

n represents 2 or 3;

$R^4$ represents $—CH_2CH_2CH_2NH(C{=}NH)NH_2$ or $—CH_2CH_2CH_2CH_2NH_2$, the configuration of the carbon atom to which $R^4$ is attached corresponding with that in an L-amino acid; and $R^5$ represents a hydrogen atom, an N-acyl group, or a residue of an amino acid, a dipeptide, or an N-acyl derivative of an amino acid or dipeptide.

Examples of values for the phenolic opioid as provided in X are oxymorphone, hydromorphone, and morphine.

Examples of values for $R^1$ are methyl and ethyl groups.

Examples of values for each of $R^2$ and $R^3$ are hydrogen atoms.

An example of a value for n is 2.

In one embodiment, $R^4$ represents $—CH_2CH_2CH_2NH(C{=}NH)NH_2$.

Referring to $R^5$, examples of particular values are:

for an N-acyl group: an N-(1-4C)alkanoyl group, such as acetyl, an N-aroyl group, such as N-benzoyl, or an N-piperonyl group;

for an amino acid: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine; and for a dipeptide: a combination of any two amino acids selected independently from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

An amino acid can be a naturally occurring amino acid. It will be appreciated that naturally occurring amino acids usually have the L-configuration.

Examples of particular values for $R^5$ are:

a hydrogen atom;

for an N-acyl group: an N-(1-4C)alkanoyl group, such as acetyl, an N-aroyl group, such as N-benzoyl, or an N-piperonyl group; and for a residue of an amino acid, a dipeptide, or an N-acyl derivative of an amino acid or dipeptide: glycinyl or N-acetylglycinyl.

In one embodiment, $R^5$ represents N-acetyl, N-glycinyl or N-acetylglycinyl, such as N-acetyl.

An example of the group represented by —C(O)—CH($R^4$)—NH($R^5$) is N-acetylarginyl.

Formula PC-(II)

The embodiments provide a pharmaceutical composition, which comprises a compound of general formula PC-(IIa):

$$X—C(O)—NR^1—(C(R^2)(R^3))_n—NH—C(O)—CH(R^4)—NH(R^5) \quad (PC\text{-}(IIa))$$

or a pharmaceutically acceptable salt thereof, in which:

- X represents a residue of a phenolic opioid, wherein the hydrogen atom of the phenolic hydroxyl group is replaced by a covalent bond to —C(O)—$NR^1$—(C($R^2$)($R^3$))$_n$—NH—C(O)—CH($R^4$)—NH($R^5$);
- $R^1$ is selected from alkyl, substituted alkyl, arylalkyl, substituted arylalkyl, aryl and substituted aryl;
- each $R^2$ is independently selected from hydrogen, alkyl, substituted alkyl, aryl, substituted aryl, acyl, and aminoacyl;
- each $R^3$ is independently selected from hydrogen, alkyl, substituted alkyl, aryl, substituted aryl, acyl, and aminoacyl;
- or $R^2$ and $R^3$ together with the carbon to which they are attached form a cycloalkyl, substituted cycloalkyl, aryl, or substituted aryl group, or two $R^2$ or $R^3$ groups on adjacent carbon atoms, together with the carbon atoms to which they are attached, form a cycloalkyl, substituted cycloalkyl, aryl, or substituted aryl group;
- n represents an integer from 2 to 4;
- $R^4$ represents —$CH_2CH_2CH_2NH$(C═NH)$NH_2$ or —$CH_2CH_2CH_2CH_2NH_2$, the configuration of the carbon atom to which $R^4$ is attached corresponding with that in an L-amino acid; and
- $R^5$ represents a hydrogen atom, an N-acyl group (including N-substituted acyl), a residue of an amino acid, a dipeptide, or an N-acyl derivative (including N-substituted acyl derivative) of an amino acid or dipeptide.

The embodiments provide a pharmaceutical composition, which comprises a compound of general formula PC-(IIb):

$$X—C(O)—NR^1—(C(R^2)(R^3))_n—NH—C(O)—CH(R^4)—NH(R^5) \quad (PC\text{-}(IIb))$$

or a pharmaceutically acceptable salt thereof, in which:

- X represents a residue of a phenolic opioid, wherein the hydrogen atom of the phenolic hydroxyl group is replaced by a covalent bond to —C(O)—$NR^1$—(C($R^2$)($R^3$))$_n$—NH—C(O)—CH($R^4$)—NH($R^5$);
- $R^1$ is selected from alkyl, substituted alkyl, arylalkyl, substituted arylalkyl, aryl and substituted aryl;
- each $R^2$ is independently selected from hydrogen, alkyl, substituted alkyl, aryl, substituted aryl, acyl, and aminoacyl;
- each $R^3$ is independently selected from hydrogen, alkyl, substituted alkyl, aryl, substituted aryl, acyl, and aminoacyl;
- or $R^2$ and $R^3$ together with the carbon to which they are attached form a cycloalkyl or substituted cycloalkyl group, or two $R^2$ or $R^3$ groups on adjacent carbon atoms, together with the carbon atoms to which they are attached, form a cycloalkyl or substituted cycloalkyl group;
- n represents an integer from 2 to 4;
- $R^4$ represents —$CH_2CH_2CH_2NH$(C═NH)$NH_2$ or —$CH_2CH_2CH_2CH_2NH_2$, the configuration of the carbon atom to which $R^4$ is attached corresponding with that in an L-amino acid; and
- $R^5$ represents a hydrogen atom, an N-acyl group (including N-substituted acyl), a residue of an amino acid, a dipeptide, or an N-acyl derivative (including N-substituted acyl derivative) of an amino acid or dipeptide.

Reference to formula PC-(II) is meant to include compounds of formula PC-(IIa) and PC-(IIb).

In formula PC-(II), examples of values for the phenolic opioid as provided in X are oxymorphone, hydromorphone, and morphine.

In formula PC-(II), $R^1$ can be selected from alkyl, substituted alkyl, arylalkyl, substituted arylalkyl, aryl and substituted aryl. In certain instances, $R^1$ is (1-6C)alkyl. In other instances, $R^1$ is (1-4C)alkyl. In other instances, $R^1$ is methyl or ethyl. In other instances, $R^1$ is methyl. In some instances, $R^1$ is ethyl.

In certain instances, in formula PC-(II), $R^1$ is substituted alkyl. In certain instances, $R^1$ is an alkyl group substituted with a carboxylic group such as a carboxylic acid, carboxylic ester or carboxylic amide. In certain instances, $R^1$ is —$(CH_2)_n$—COOH, —$(CH_2)_n$—$COOCH_3$, or —$(CH_2)_n$—$COOCH_2CH_3$, wherein n is a number from one to 10. In certain instances, $R^1$ is —$(CH_2)_5$—COOH, —$(CH_2)_5$—$COOCH_3$, or —$(CH_2)_5$—$COOCH_2CH_3$.

In certain instances, in formula PC-(II), $R^1$ is arylalkyl or substituted arylalkyl. In certain instances, $R^1$ is arylalkyl. In certain instances, $R^1$ is substituted arylalkyl. In certain instances, $R^1$ is an arylalkyl group substituted with a carboxylic group such as a carboxylic acid, carboxylic ester or carboxylic amide. In certain instances, $R^1$ is —$(CH_2)_q$($C_6H_4$)—COOH, —$(CH_2)_q$($C_6H_4$)—$COOCH_3$, or —$(CH_2)_q$($C_6H_4$)—$COOCH_2CH_3$, where q is an integer from one to 10. In certain instances, $R^1$ is —$CH_2$($C_6H_4$)—COOH, —$CH_2$($C_6H_4$)—$COOCH_3$, or —$CH_2$ ($C_6H_4$)—$COOCH_2CH_3$.

In certain instances, in formula PC-(II), $R^1$ is aryl. In certain instances, $R^1$ is substituted aryl. In certain instances, $R^1$ is an aryl group with ortho, meta or para-substituted with a carboxylic group such as a carboxylic acid, carboxylic ester or carboxylic amide. In certain instances, $R^1$ is —($C_6H_4$)—COOH, —($C_6H_4$)—$COOCH_3$, or —($C_6H_4$)—$COOCH_2CH_3$.

In formula PC-(II), each $R^2$ can be independently selected from hydrogen, alkyl, substituted alkyl, aryl, substituted aryl, acyl, and aminoacyl. In certain instances, $R^2$ is hydrogen or alkyl. In certain instances, $R^2$ is hydrogen. In certain instances, $R^2$ is alkyl. In certain instances, $R^2$ is acyl. In certain instances, $R^2$ is aminoacyl.

In formula PC-(II), each $R^3$ can be independently selected from hydrogen, alkyl, substituted alkyl, aryl, substituted aryl, acyl, and aminoacyl. In certain instances, $R^3$ is hydrogen or alkyl. In certain instances, $R^3$ is hydrogen. In certain instances, $R^3$ is alkyl. In certain instances, $R^3$ is acyl. In certain instances, $R^3$ is aminoacyl.

In certain instances, $R^2$ and $R^3$ are hydrogen. In certain instances, $R^2$ and $R^3$ on the same carbon are both alkyl. In certain instances, $R^2$ and $R^3$ on the same carbon are methyl. In certain instances, $R^2$ and $R^3$ on the same carbon are ethyl.

In certain instances, $R^2$ and $R^2$ which are vicinal are both alkyl and $R^3$ and $R^3$ which are vicinal are both hydrogen. In certain instances, $R^2$ and $R^2$ which are vicinal are both ethyl and $R^3$ and $R^3$ which are vicinal are both hydrogen. In certain instances, $R^2$ and $R^2$ which are vicinal are both methyl and $R^3$ and $R^3$ which are vicinal are both hydrogen.

In certain instances, in the chain of $—[C(R^2)(R^3)]_n—$ in Formula PC-(II), not every carbon is substituted. In certain instances, in the chain of $—[C(R^2)(R^3)]_n—$, there is a combination of different alkyl substituents, such as methyl or ethyl.

In certain instances, one of $R^2$ and $R^3$ is methyl, ethyl or other alkyl and $R^1$ is alkyl. In certain instances, $R^2$ and $R^2$ which are vicinal are both alkyl and $R^3$ and $R^3$ which are vicinal are both hydrogen and $R^1$ is alkyl. In certain instances, $R^2$ and $R^2$ which are vicinal are both ethyl and $R^3$ and $R^3$ which are vicinal are both hydrogen and $R^1$ is alkyl. In certain instances, $R^2$ and $R^2$ which are vicinal are both methyl and $R^3$ and $R^3$ which are vicinal are both hydrogen and $R^1$ is alkyl.

In certain instances, one of $R^2$ and $R^3$ is methyl, ethyl or other alkyl and $R^1$ is substituted alkyl. In certain instances, one of $R^2$ and $R^3$ is methyl, ethyl or other alkyl and $R^1$ is an alkyl group substituted with a carboxylic group such as a carboxylic acid, carboxylic ester or carboxylic amide. In certain instances, one of $R^2$ and $R^3$ is methyl, ethyl or other alkyl and $R^1$ is $—(CH_2)_q(C_6H_4)—COOH$, $—(CH_2)_q(C_6H_4)—COOCH_3$, or $—(CH_2)_q(C_6H_4)—COOCH_2CH_3$, where q is an integer from one to 10. In certain instances, one of $R^2$ and $R^3$ is methyl, ethyl or other alkyl and $R^1$ is carboxamide.

In formula PC-(II), $R^2$ and $R^3$ together with the carbon to which they are attached can form a cycloalkyl or substituted cycloalkyl group, or two $R^2$ or $R^3$ groups on adjacent carbon atoms, together with the carbon atoms to which they are attached, can form a cycloalkyl or substituted cycloalkyl group. In certain instances, $R^2$ and $R^3$ together with the carbon to which they are attached can form a cycloalkyl group. Thus, in certain instances, $R^2$ and $R^3$ on the same carbon form a spirocycle. In certain instances, $R^2$ and $R^3$ together with the carbon to which they are attached can form a substituted cycloalkyl group. In certain instances, two $R^2$ or $R^3$ groups on adjacent carbon atoms, together with the carbon atoms to which they are attached, can form a cycloalkyl group. In certain instances, two $R^2$ or $R^3$ groups on adjacent carbon atoms, together with the carbon atoms to which they are attached, can form a substituted cycloalkyl group.

In certain instances, $R^2$ and $R^3$ together with the carbon to which they are attached can form an aryl or substituted aryl group, or two $R^2$ or $R^3$ groups on adjacent carbon atoms, together with the carbon atoms to which they are attached, can form an aryl or substituted aryl group. In certain instances, two $R^2$ or $R^3$ groups on adjacent carbon atoms, together with the carbon atoms to which they are attached, form a phenyl ring. In certain instances, two $R^2$ or $R^3$ groups on adjacent carbon atoms, together with the carbon atoms to which they are attached, form a substituted phenyl ring. In certain instances, two $R^2$ or $R^3$ groups on adjacent carbon atoms, together with the carbon atoms to which they are attached, form a naphthyl ring.

In certain instances, one of $R^2$ and $R^3$ is aminoacyl.

In certain instances, one of $R^2$ and $R^3$ is aminoacyl comprising phenylenediamine. In certain instances, one or both of $R^2$ and $R^3$ is

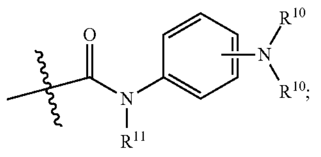

wherein each $R^{10}$ is independently selected from hydrogen, alkyl, substituted alkyl, and acyl and $R^{11}$ is alkyl or substituted alkyl. In certain instances, at least one of $R^{10}$ is acyl. In certain instances, at least one of $R^{10}$ is alkyl or substituted alkyl. In certain instances, at least one of $R^{10}$ is hydrogen. In certain instances, both of $R^{10}$ are hydrogen.

In certain instances, one of $R^2$ and $R^3$ is

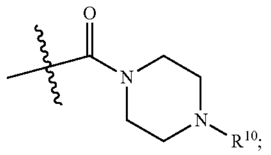

wherein $R^{10}$ is hydrogen, alkyl, substituted alkyl, or acyl. In certain instances, $R^{10}$ is acyl. In certain instances, $R^{10}$ is alkyl or substituted alkyl. In certain instances, $R^{10}$ is hydrogen.

In certain instances, one of $R^2$ and $R^3$ is

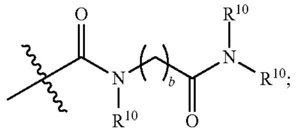

wherein each $R^{10}$ is independently hydrogen, alkyl, substituted alkyl, or acyl and b is a number from one to 5. In certain instances, one of $R^2$ and $R^3$ is

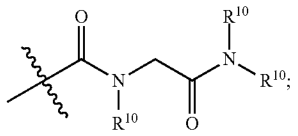

wherein each $R^{10}$ is independently hydrogen, alkyl, substituted alkyl, or acyl. In certain instances, one of $R^2$ and $R^3$ is

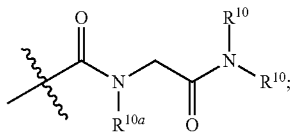

wherein $R^{10a}$ is alkyl and each $R^{10}$ is independently hydrogen, alkyl, substituted alkyl, or acyl.

In certain instances, one of $R^2$ and $R^3$ is

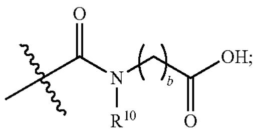

wherein $R^{10}$ is independently hydrogen, alkyl, substituted alkyl, or acyl and b is a number from one to 5. In certain instances, one of $R^2$ and $R^3$ is

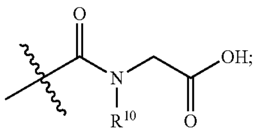

wherein $R^{10}$ is independently hydrogen, alkyl, substituted alkyl, or acyl.

In certain instances, one of $R^2$ and $R^3$ is an aminoacyl group, such as —C(O)NR$^{10a}$R$^{10b}$, wherein each $R^{10a}$ and $R^{10b}$ is independently selected from hydrogen, alkyl, substituted alkyl, and acyl. In certain instances, one of $R^2$ and $R^3$ is an aminoacyl group, such as —C(O)NR$^{10a}$R$^{10b}$, wherein $R^{10a}$ is an alkyl and $R^{10b}$ is substituted alkyl. In certain instances, one of $R^2$ and $R^3$ is an aminoacyl group, such as —C(O)NR$^{10a}$R$^{10b}$, wherein $R^{10a}$ is an alkyl and $R^{10b}$ is alkyl substituted with a carboxylic acid or carboxyl ester. In certain instances, one of $R^2$ and $R^3$ is an aminoacyl group, such as —C(O)NR$^{10a}$R$^{10b}$, wherein $R^{10a}$ is methyl and $R^{10b}$ is alkyl substituted with a carboxylic acid or carboxyl ester.

In certain instances, $R^2$ or $R^3$ can modulate a rate of intramolecular cyclization. $R^2$ or $R^3$ can speed up a rate of intramolecular cyclization, when compared to the corresponding molecule where $R^2$ and $R^3$ are both hydrogen. In certain instances, $R^2$ or $R^3$ comprise an electron-withdrawing group or an electron-donating group. In certain instances, $R^2$ or $R^3$ comprise an electron-withdrawing group. In certain instances, $R^2$ or $R^3$ comprise an electron-donating group.

Atoms and groups capable of functioning as electron withdrawing substituents are well known in the field of organic chemistry. They include electronegative atoms and groups containing electronegative atoms. Such groups function to lower the basicity or protonation state of a nucleophilic nitrogen in the beta position via inductive withdrawal of electron density. Such groups can also be positioned on other positions along the alkylene chain. Examples include halogen atoms (for example, a fluorine atom), acyl groups (for example an alkanoyl group, an aroyl group, a carboxyl group, an alkoxycarbonyl group, an aryloxycarbonyl group or an aminocarbonyl group (such as a carbamoyl, alkylaminocarbonyl, dialkylaminocarbonyl or arylaminocarbonyl group)), an oxo (═O) substituent, a nitrile group, a nitro group, ether groups (for example an alkoxy group) and phenyl groups bearing a substituent at the ortho position, the para position or both the ortho and the para positions, each substituent being selected independently from a halogen atom, a fluoroalkyl group (such as trifluoromethyl), a nitro group, a cyano group and a carboxyl group. Each of the electron withdrawing substituents can be selected independently from these.

In certain instances, —[C(R$^2$)(R$^3$)]$_n$— is selected from —CH(CH$_2$F)CH(CH$_2$F)—; —CH(CHF$_2$)CH(CHF$_2$)—; —CH(CF$_3$)CH(CF$_3$)—; —CH$_2$CH(CF$_3$)—; —CH$_2$CH(CHF$_2$)—; —CH$_2$CH(CH$_2$F)—; —CH$_2$CH(F)CH$_2$—; —CH$_2$C(F$_2$)CH$_2$—; —CH$_2$CH(C(O)NR$^{20}$R$^{21}$)—; —CH$_2$CH(C(O)OR$^{22}$)—; —CH$_2$CH(C(O)OH)—; —CH(CH$_2$F)CH$_2$CH(CH$_2$F)—; —CH(CHF$_2$)CH$_2$CH(CHF$_2$)—; —CH(CF$_3$)CH$_2$CH(CF$_3$)—; —CH$_2$CH$_2$CH(CF$_3$)—; —CH$_2$CH$_2$CH(CHF$_2$)—; —CH$_2$CH$_2$CH(CH$_2$F)—; —CH$_2$CH$_2$CH(C(O) NR$^{23}$R$^{24}$)—; —CH$_2$CH$_2$CH(C(O)OR$^{25}$)—; and —CH$_2$CH$_2$CH(C(O)OH)—, in which $R^{20}$, $R^{21}$, $R^{22}$ and $R^{23}$ each independently represents hydrogen or (1-6C)alkyl, and $R^{24}$ and $R^{25}$ each independently represents (1-6C)alkyl.

In formula PC-(II), n represents an integer from 2 to 4. An example of a value for n is 2. An example of a value for n is 3. An example of a value for n is 4.

In formula PC-(II), in one embodiment, $R^4$ represents —CH$_2$CH$_2$CH$_2$NH(C═NH)NH$_2$. In another embodiment, $R^4$ represents —CH$_2$CH$_2$CH$_2$CH$_2$NH$_2$.

In formula PC-(II), referring to $R^5$, examples of particular values are:

for an N-acyl group: an N-(1-4C)alkanoyl group, such as acetyl, an N-aroyl group, such as N-benzoyl, or an N-piperonyl group;

for an amino acid: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine; and for a dipeptide: a combination of any two amino acids selected independently from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

An amino acid can be a naturally occurring amino acid. It will be appreciated that naturally occurring amino acids usually have the L-configuration.

In formula PC-(II), examples of particular values for $R^5$ are:

a hydrogen atom;

for an N-acyl group: an N-(1-4C)alkanoyl group, such as acetyl, an N-aroyl group, such as N-benzoyl, or an N-piperonyl group; and for a residue of an amino acid, a dipeptide, or an N-acyl derivative of an amino acid or dipeptide: glycinyl or N-acetylglycinyl.

In formula PC-(II), in one embodiment, $R^5$ represents N-acetyl, glycinyl or N-acetylglycinyl, such as N-acetyl.

In formula PC-(II), an example of the group represented by —C(O)—CH(R$^4$)—NH(R$^5$) is N-acetylarginyl or N-acetyllysinyl.

In formula PC-(II), in certain instances, $R^5$ represents substituted acyl. In certain instances, $R^5$ can be malonyl or succinyl.

In formula PC-(II), in certain instances, the group represented by —C(O)—CH(R$^4$)—NH(R$^5$) is N-malonylarginyl, N-malonyllysinyl, N-succinylarginyl and N-succinyllysinyl.

Formula PC-(III)

The embodiments provide a pharmaceutical composition, which comprises a compound of general formula PC-(III):

X—C(O)—NR$^1$—(C(R$^2$)(R$^3$))$_n$—NH—C(O)—CH(R$^4$)—NH(R$^5$) (PC-(III))

or pharmaceutically acceptable salt thereof, in which:

X represents a residue of a phenolic opioid, wherein the hydrogen atom of the phenolic hydroxyl group is replaced by a covalent bond to —C(O)—$NR^1$—($C(R^2)(R^3))_n$—NH—C(O)—$CH(R^4)$—$NH(R^5)$;

$R^1$ represents a (1-4C)alkyl group;

$R^2$ and $R^3$ each independently represents a hydrogen atom or a (1-4C)alkyl group;

n represents 2 or 3;

$R^4$ represents —$CH_2CH_2CH_2NH(C{=}NH)NH_2$ or —$CH_2CH_2CH_2CH_2NH_2$, the configuration of the carbon atom to which $R^4$ is attached corresponding with that in an L-amino acid; and $R^5$ represents a hydrogen atom, an N-acyl group (including N-substituted acyl), a residue of an amino acid, a dipeptide, or an N-acyl derivative (including N-substituted acyl derivative) of an amino acid or dipeptide.

In formula PC-(III), examples of values for the phenolic opioid as provided in X are oxymorphone, hydromorphone, and morphine.

In formula PC-(III), examples of values for $R^1$ are methyl and ethyl groups.

In formula PC-(III), examples of values for each of $R^2$ and $R^3$ are hydrogen atoms.

In formula PC-(III), an example of a value for n is 2.

In formula PC-(III), in one embodiment, $R^4$ represents —$CH_2CH_2CH_2NH(C{=}NH)NH_2$. In another embodiment, $R^4$ represents —$CH_2CH_2CH_2CH_2NH_2$.

In formula PC-(III), referring to $R^5$, examples of particular values are:

for an N-acyl group: an N-(1-4C)alkanoyl group, such as acetyl, an N-aroyl group, such as N-benzoyl, or an N-piperonyl group;

for an amino acid: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine; and for a dipeptide: a combination of any two amino acids selected independently from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

An amino acid can be a naturally occurring amino acid. It will be appreciated that naturally occurring amino acids usually have the L-configuration.

In formula PC-(III), examples of particular values for $R^5$ are:

a hydrogen atom;

for an N-acyl group: an N-(1-4C)alkanoyl group, such as acetyl, an N-aroyl group, such as N-benzoyl, or an N-piperonyl group; and for a residue of an amino acid, a dipeptide, or an N-acyl derivative of an amino acid or dipeptide: glycinyl or N-acetylglycinyl.

In formula PC-(III), in one embodiment, $R^5$ represents N-acetyl, glycinyl or N-acetylglycinyl, such as N-acetyl.

In formula PC-(III), an example of the group represented by —C(O)—$CH(R^4)$—$NH(R^5)$ is N-acetylarginyl or N-acetyllysinyl.

In formula PC-(III), in certain instances, $R^5$ represents substituted acyl. In certain instances, $R^5$ can be malonyl or succinyl.

In formula PC-(III), in certain instances, the group represented by —C(O)—$CH(R^4)$—$NH(R^5)$ is N-malonylarginyl, N-malonyllysinyl, N-succinylarginyl and N-succinyllysinyl.

In certain embodiments, the phenol-modified opioid prodrug is hydromorphone 3-(N-methyl-N-(2-N'-acetylarginylamino))ethylcarbamate, or a pharmaceutically acceptable salt thereof. In certain embodiments, the phenol-modified opioid prodrug is oxymorphone 3-(N-methyl-N-(2-N'-acetylarginylamino))ethylcarbamate, or a pharmaceutically acceptable salt thereof. In certain embodiments, the phenol-modified opioid prodrug is morphine 3-(N-methyl-N-(2-N'-acetylarginylamino))ethylcarbamate, or a pharmaceutically acceptable salt thereof.

In some embodiments, the phenol-modified opioid prodrugs include those described in International Patent Publication Nos. WO 2007/140272; WO 2010/045599; WO 2011/133149 and WO 2011/133178, the disclosures of which are herein incorporated by reference.

Ketone-Modified Opioid Prodrugs

The disclosure provides a ketone-modified opioid prodrug which provides enzymatically-controlled release of a ketone-containing opioid. As used herein, a ketone-containing opioid is an opioid containing an enolizable ketone group. In a ketone-modified opioid prodrug, a promoiety is attached to the ketone-containing opioid through the enolic oxygen atom of the ketone moiety. In a ketone-modified opioid prodrug, the hydrogen atom of the corresponding enolic group of the ketone-containing opioid is replaced by a covalent bond to a promoiety.

As disclosed herein, a trypsin-cleavable ketone-modified opioid prodrug is a ketone-modified opioid prodrug that comprises a promoiety comprising a trypsin-cleavable moiety, i.e., a moiety having a site susceptible to cleavage by trypsin. Such a prodrug comprises a ketone-containing opioid covalently bound to a promoiety comprising a trypsin-cleavable moiety, wherein cleavage of the trypsin-cleavable moiety by trypsin mediates release of the drug. Cleavage can initiate, contribute to or effect drug release.

In embodiments, the ketone-containing opioid may include, but is not limited to acetylmorphone, hydrocodone, hydromorphone, ketobemidone, methadone, naloxone, naltrexone, N-methylnaloxone, N-methylnaltrexone, oxycodone, oxymorphone, and pentamorphone.

Ketone-Modified Opioid Prodrugs with Promoiety Comprising Cyclizable Spacer Leaving Group and Cleavable Moiety According to certain embodiments, there is provided a ketone-modified opioid prodrug which provides enzymatically-controlled release of a ketone-containing opioid. The disclosure provides for a ketone-modified opioid in which the promoiety comprises a cyclizable spacer leaving group and a cleavable moiety. In certain embodiments, the ketone-containing opioid is a corresponding compound in which the enolic oxygen atom has a substituent which is a spacer leaving group bearing a nitrogen nucleophile that is protected with an enzymatically-cleavable moiety, the configuration of the spacer leaving group and nitrogen nucleophile being such that, upon enzymatic cleavage of the cleavable moiety, the nitrogen nucleophile is capable of forming a cyclic urea, liberating the compound from the spacer leaving group so as to provide a ketone-containing opioid.

The corresponding prodrug provides post administration-activated, controlled release of the ketone-containing opioid. The prodrug requires enzymatic cleavage to initiate release of the ketone-containing opioid and thus the rate of release of the ketone-containing opioid depends upon both the rate of enzymatic cleavage and the rate of cyclization. Accordingly, the prodrug has reduced susceptibility to accidental overdosing or abuse, whether by deliberate overdosing, administration through an inappropriate route, such as by injection, or by chemical modification using readily available household chemicals. The prodrug is configured so that it will not provide excessively high plasma levels of the active drug if it is administered inappropriately, and cannot readily be decomposed to afford the active drug other than by enzymatic cleavage followed by controlled cyclization.

The enzyme-cleavable moiety linked to the nitrogen nucleophile through an amide bond can be, for example, a residue of an amino acid or a peptide, or an (alpha)N-acyl derivative of an amino acid or peptide (for example an N-acyl derivative of a pharmaceutically acceptable carboxylic acid). The peptide can contain, for example, up to about 100 amino acid residues. Each amino acid can advantageously be a naturally occurring amino acid, such as an L-amino acid. Examples of naturally occurring amino acids are alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine. Accordingly, examples of enzyme-cleavable moieties include residues of the L-amino acids listed hereinabove and N-acyl derivatives thereof, and peptides formed from at least two of the L-amino acids listed hereinabove, and the N-acyl derivatives thereof.

The cyclic group formed when the ketone-containing opioid is released is conveniently pharmaceutically acceptable, in particular a pharmaceutically acceptable cyclic urea. It will be appreciated that cyclic ureas are generally very stable and have low toxicity.

Formula KC-(I)

In one of its composition aspects, the present embodiments provide a compound of formula KC-(Ia):

(KC-(Ia))

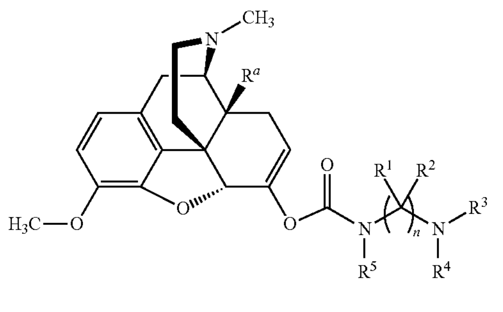

wherein:

$R^a$ is hydrogen or hydroxyl;

$R^5$ is selected from alkyl, substituted alkyl, arylalkyl, substituted arylalkyl, aryl and substituted aryl;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl, substituted cycloalkyl, aryl, or substituted aryl group, or two $R^1$ or $R^2$ groups on adjacent carbon atoms, together with the carbon atoms to which they are attached, form a cycloalkyl, substituted cycloalkyl, aryl, or substituted aryl group;

n is an integer from 2 to 4;

$R^3$ is hydrogen or (1-4C)alkyl;

$R^4$ is

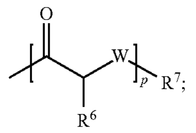

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;

each W is independently —$NR^8$—, —O— or —S—;

each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

p is an integer from one to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

In one of its composition aspects, the present embodiments provide a compound of formula KC-(Ib):

(KC-(Ib))

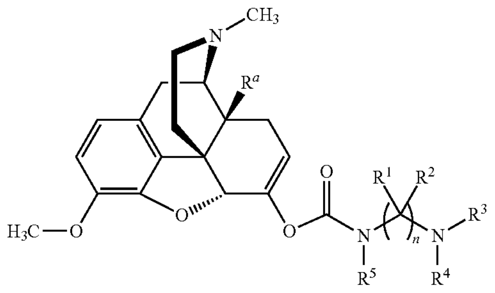

wherein:

$R^a$ is hydrogen or hydroxyl;

$R^5$ is selected from alkyl, substituted alkyl, arylalkyl, substituted arylalkyl, aryl and substituted aryl;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl or substituted cycloalkyl group, or two $R^1$ or $R^2$ groups on adjacent carbon atoms, together with the carbon atoms to which they are attached, form a cycloalkyl or substituted cycloalkyl group;

n is an integer from 2 to 4;

$R^3$ is hydrogen or (1-4C)alkyl;

$R^4$ is

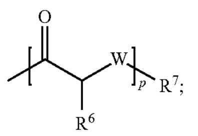

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;

each W is independently —$NR^8$—, —O— or —S—;

each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

p is an integer from one to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

Reference to formula KC-(I) is meant to include compounds of formula KC-(Ia) and KC-(Ib).

In formula KC-(I), $R^a$ can be hydrogen or hydroxyl. In certain instances, $R^a$ is hydrogen. In other instances, $R^a$ is hydroxyl.

In formula KC-(I), $R^5$ can be selected from alkyl, substituted alkyl, arylalkyl, substituted arylalkyl, aryl and substituted aryl. In certain instances, $R^5$ is (1-6C)alkyl. In other instances, $R^5$ is (1-4C)alkyl. In other instances, $R^5$ is methyl or ethyl. In other instances, $R^5$ is methyl. In certain instances, $R^5$ is ethyl.

In certain instances, $R^5$ is substituted alkyl. In certain instances, $R^5$ is an alkyl group substituted with a carboxylic group such as a carboxylic acid, carboxylic ester or carboxylic amide. In certain instances, $R^5$ is $-(CH_2)_n-COOH$, $-(CH_2)_n-COOCH_3$, or $-(CH_2)_n-COOCH_2CH_3$, wherein n is a number form one to 10. In certain instances, $R^1$ is $-(CH_2)_5-COOH$, $-(CH_2)_5-COOCH_3$, or $-(CH_2)_5-COOCH_2CH_3$.

In certain instances, in formula KC-(I), $R^5$ is arylalkyl or substituted arylalkyl. In certain instances, in formula KC-(I), $R^5$ is arylalkyl. In certain instances, $R^5$ is substituted arylalkyl. In certain instances, $R^5$ is an arylalkyl group substituted with a carboxylic group such as a carboxylic acid, carboxylic ester or carboxylic amide. In certain instances, $R^5$ is $-(CH_2)_q(C_6H_4)-COOH$, $-(CH_2)_q(C_6H_4)-COOCH_3$, or $-(CH_2)_q(C_6H_4)-COOCH_2CH_3$, where q is an integer from one to 10. In certain instances, $R^5$ is $-CH_2(C_6H_4)-COOH$, $-CH_2(C_6H_4)-COOCH_3$, or $-CH_2(C_6H_4)-COOCH_2CH_3$.

In certain instances, in formula KC-(I), $R^5$ is aryl. In certain instances, $R^5$ is substituted aryl. In certain instances, $R^5$ is an aryl group ortho, meta or para-substituted with a carboxylic group such as a carboxylic acid, carboxylic ester or carboxylic amide. In certain instances, $R^5$ is $-(C_6H_4)-COOH$, $-(C_6H_4)-COOCH_3$, or $-(C_6H_4)-COOCH_2CH_3$.

In formula KC-(I), each $R^1$ can be independently selected from hydrogen, alkyl, substituted alkyl, aryl, substituted aryl, acyl, and aminoacyl. In certain instances, $R^1$ is hydrogen or alkyl. In certain instances, $R^1$ is hydrogen. In certain instances, $R^1$ is alkyl. In certain instances, $R^1$ is acyl. In certain instances, $R^1$ is aminoacyl.

In formula KC-(I), each $R^2$ can be independently selected from hydrogen, alkyl, substituted alkyl, aryl, substituted aryl, acyl, and aminoacyl. In certain instances, $R^2$ is hydrogen or alkyl. In certain instances, $R^2$ is hydrogen. In certain instances, $R^2$ is alkyl. In certain instances, $R^2$ is acyl. In certain instances, $R^2$ is aminoacyl.

In certain instances, $R^1$ and $R^2$ are hydrogen. In certain instances, $R^1$ and $R^2$ on the same carbon are both alkyl. In certain instances, $R^1$ and $R^2$ on the same carbon are methyl. In certain instances, $R^1$ and $R^2$ on the same carbon are ethyl.

In certain instances, $R^1$ and $R^1$ which are vicinal are both alkyl and $R^2$ and $R^2$ which are vicinal are both hydrogen. In certain instances, $R^1$ and $R^1$ which are vicinal are both ethyl and $R^2$ and $R^2$ which are vicinal are both hydrogen. In certain instances, $R^1$ and $R^1$ which are vicinal are both methyl and $R^2$ and $R^2$ which are vicinal are both hydrogen.

In certain instances, in the chain of $-[C(R^1)(R^2)]_n-$ in Formula KC-(I), not every carbon is substituted. In certain instances, in the chain of $-[C(R^1)(R^2)]_n-$, there is a combination of different alkyl substituents, such as methyl or ethyl.

In certain instances, one of $R^1$ and $R^2$ is methyl, ethyl or other alkyl and $R^5$ is alkyl. In certain instances, $R^1$ and $R^1$ which are vicinal are both alkyl and $R^2$ and $R^2$ which are vicinal are both hydrogen and $R^5$ is alkyl. In certain instances, $R^1$ and $R^1$ which are vicinal are both ethyl and $R^2$ and $R^2$ which are vicinal are both hydrogen and $R^5$ is alkyl. In certain instances, $R^1$ and $R^1$ which are vicinal are both methyl and $R^2$ and $R^2$ which are vicinal are both hydrogen and $R^5$ is alkyl.

In certain instances, one of $R^1$ and $R^2$ is methyl, ethyl or other alkyl and $R^5$ is substituted alkyl. In certain instances, one of $R^1$ and $R^2$ is methyl, ethyl or other alkyl and $R^5$ is an alkyl group substituted with a carboxylic group such as a carboxylic acid, carboxylic ester or carboxylic amide. In certain instances, one of $R^1$ and $R^2$ is methyl, ethyl or other alkyl and $R^5$ is $-(CH_2)_q(C_6H_4)-COOH$, $-(CH_2)_q(C_6H_4)-COOCH_3$, or $-(CH_2)_q(C_6H_4)-COOCH_2CH_3$, where q is an integer from one to 10. In certain instances, one of $R^1$ and $R^2$ is methyl, ethyl or other alkyl and $R^5$ is an alkyl group substituted with carboxamide.

In formula KC-(I), $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group. In certain instances, $R^1$ and $R^2$ together with the carbon to which they are attached can form a cycloalkyl group. Thus, in certain instances, $R^1$ and $R^2$ on the same carbon form a spirocycle. In certain instances, $R^1$ and $R^2$ together with the carbon to which they are attached can form a substituted cycloalkyl group. In certain instances, two $R^1$ or $R^2$ groups on adjacent carbon atoms, together with the carbon atoms to which they are attached, can form a cycloalkyl group. In certain instances, two $R^1$ or $R^2$ groups on adjacent carbon atoms, together with the carbon atoms to which they are attached, can form a substituted cycloalkyl group.

In formula KC-(I), $R^1$ and $R^2$ together with the carbon to which they are attached can form an aryl or substituted aryl group, or two $R^1$ or $R^2$ groups on adjacent carbon atoms, together with the carbon atoms to which they are attached, can form an aryl or substituted aryl group. In certain instances, two $R^1$ or $R^2$ groups on adjacent carbon atoms, together with the carbon atoms to which they are attached, form a phenyl ring. In certain instances, two $R^1$ or $R^2$ groups on adjacent carbon atoms, together with the carbon atoms to which they are attached, form a substituted phenyl ring. In certain instances, two $R^1$ or $R^2$ groups on adjacent carbon atoms, together with the carbon atoms to which they are attached, form a naphthyl ring.

In certain instances, one of $R^1$ and $R^2$ is aminoacyl.

In certain instances, one or both of $R^1$ and $R^2$ is aminoacyl comprising phenylenediamine.

In certain instances, one of $R^1$ and $R^2$ is

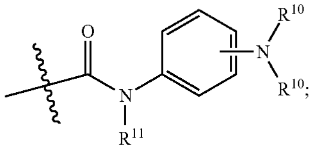

wherein each $R^{10}$ is independently selected from hydrogen, alkyl, substituted alkyl, and acyl and $R^{11}$ is alkyl or substituted alkyl. In certain instances, at least one of $R^{10}$ is acyl. In certain instances, at least one of $R^{10}$ is alkyl or substituted alkyl. In certain instances, at least one of $R^1$ is hydrogen. In certain instances, both of $R^1$ are hydrogen.

In certain instances, one of $R^1$ and $R^2$ is

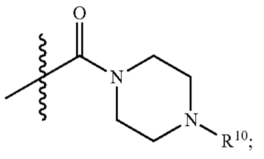

wherein $R^{10}$ is hydrogen, alkyl, substituted alkyl, or acyl. In certain instances, $R^{10}$ is acyl. In certain instances, $R^{10}$ is alkyl or substituted alkyl. In certain instances, $R^{10}$ is hydrogen.

In certain instances, one of $R^1$ and $R^2$ is

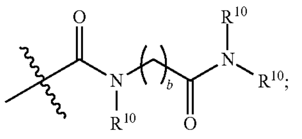

wherein each $R^{10}$ is independently hydrogen, alkyl, substituted alkyl, or acyl and b is a number from one to 5. In certain instances, one of $R^1$ and $R^2$ is

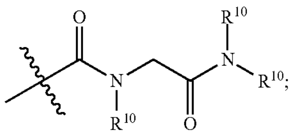

wherein each $R^{10}$ is independently hydrogen, alkyl, substituted alkyl, or acyl. In certain instances, one of $R^1$ and $R^2$ is

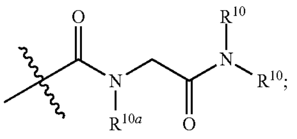

wherein $R^{10a}$ is alkyl and each $R^{10}$ is independently hydrogen, alkyl, substituted alkyl, or acyl.

In certain instances, one of $R^1$ and $R^2$ is

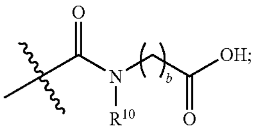

wherein $R^{10}$ is independently hydrogen, alkyl, substituted alkyl, or acyl and b is a number from one to 5. In certain instances, one of $R^1$ and $R^2$ is

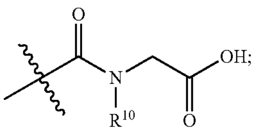

wherein $R^{10}$ is independently hydrogen, alkyl, substituted alkyl, or acyl.

In certain instances, one of $R^1$ and $R^2$ is an aminoacyl group, such as —C(O)$NR^{10a}R^{10b}$, wherein each $R^{10a}$ and $R^{10b}$ is independently selected from hydrogen, alkyl, substituted alkyl, and acyl. In certain instances, one of $R^1$ and $R^2$ is an aminoacyl group, such as —C(O)$NR^{10a}R^{10b}$, wherein $R^{10a}$ is an alkyl and $R^{10b}$ is substituted alkyl. In certain instances, one of $R^1$ and $R^2$ is an aminoacyl group, such as —C(O)$NR^{10a}R^{10b}$, wherein $R^{10a}$ is an alkyl and $R^{10b}$ is alkyl substituted with a carboxylic acid or carboxyl ester. In certain instances, one of $R^1$ and $R^2$ is an aminoacyl group, such as —C(O)$NR^{10a}R^{10b}$, wherein $R^{10a}$ is methyl and $R^{10b}$ is alkyl substituted with a carboxylic acid or carboxyl ester.

In certain instances, $R^1$ or $R^2$ can modulate a rate of intramolecular cyclization. $R^1$ or $R^2$ can speed up a rate of intramolecular cyclization, when compared to the corresponding molecule where $R^1$ and $R^2$ are both hydrogen. In certain instances, $R^1$ or $R^2$ comprise an electron-withdrawing group or an electron-donating group. In certain instances, $R^1$ or $R^2$ comprise an electron-withdrawing group. In certain instances, $R^1$ or $R^2$ comprise an electron-donating group.

Atoms and groups capable of functioning as electron withdrawing substituents are well known in the field of organic chemistry. They include electronegative atoms and groups containing electronegative atoms. Such groups function to lower the basicity or protonation state of a nucleophilic nitrogen in the beta position via inductive withdrawal of electron density. Such groups can also be positioned on other positions along the alkylene chain. Examples include halogen atoms (for example, a fluorine atom), acyl groups (for example an alkanoyl group, an aroyl group, a carboxyl group, an alkoxycarbonyl group, an aryloxycarbonyl group or an aminocarbonyl group (such as a carbamoyl, alkylaminocarbonyl, dialkylaminocarbonyl or arylaminocarbonyl group)), an oxo (=O) substituent, a nitrile group, a nitro group, ether groups (for example an alkoxy group) and phenyl groups bearing a substituent at the ortho position, the para position or both the ortho and the para positions, each substituent being selected independently from a halogen atom, a fluoroalkyl group (such as trifluoromethyl), a nitro group, a cyano group and a carboxyl group. Each of the electron withdrawing substituents can be selected independently from these.

In certain instances, $-[C(R^1)(R^2)]_n-$ is selected from $-CH(CH_2F)CH(CH_2F)-$; $-CH(CHF_2)CH(CHF_2)-$; $-CH(CF_3)CH(CF_3)-$; $-CH_2CH(CF_3)-$; $-CH_2CH(CHF_2)-$; $-CH_2CH(CH_2F)-$; $-CH_2CH(F)CH_2-$; $-CH_2C(F_2)CH_2-$; $-CH_2CH(C(O)NR^{20}R^{21})-$; $-CH_2CH(C(O)OR^{22})-$; $-CH_2CH(C(O)OH)-$; $-CH(CH_2F)CH_2CH(CH_2F)-$; $-CH(CHF_2)CH_2CH(CHF_2)-$; $-CH(CF_3)CH_2CH(CF_3)-$; $-CH_2CH_2CH(CF_3)-$; $-CH_2CH_2CH(CHF_2)-$; $-CH_2CH_2CH(CH_2F)-$; $-CH_2CH_2CH(C(O)NR^{23}R^{24})-$; $-CH_2CH_2CH(C(O)OR^{25})-$; and $-CH_2CH_2CH(C(O)OH)-$, in which $R^{20}$, $R^{21}$, $R^{22}$ and $R^{23}$ each independently represents hydrogen or (1-6C)alkyl, and $R^{24}$ and $R^{25}$ each independently represents (1-6C)alkyl.

In formula KC-(I), n can be an integer from 2 to 4. In certain instances, n is two. In other instances, n is three. In other instances, n is four.

In formula KC-(I), $R^3$ can be hydrogen or (1-4C)alkyl. In certain instances, $R^3$ is hydrogen or methyl. In certain instances, $R^3$ is hydrogen. In certain instances, $R^3$ is methyl. In certain instances, $R^3$ is ethyl. In certain instances, $R^3$ is propyl or butyl.

In formula KC-(I), $R^4$ can be a residue of an L-amino acid selected from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine, or a residue of an N-acyl derivative of any of said amino acids; or a residue of a peptide composed of at least two L-amino acid residues selected independently from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine or a residue of an N-acyl derivative thereof. Such a peptide can be from 2 to about 100 amino acids in length. Examples of N-acyl derivatives include acetyl, benzoyl, malonyl, piperonyl or succinyl derivatives.

In certain instances, $R^4$ is a residue of L-arginine or L-lysine, or a residue of an N-acyl derivative of L-arginine or L-lysine.

In certain instances, in formula KC-(I), when p is greater than one, then the $R^4$ adjacent to the nitrogen of $-N(R^3)(R^4)$ is a residue of L-arginine or L-lysine. In certain instances, when p is greater than one, the $R^4$ adjacent to the nitrogen of $-N(R^3)(R^4)$ is a residue of L-arginine or L-lysine and the first residue is joined to at least one additional L-amino acid residue selected independently from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine. The terminal residue of the peptide can be an N-acyl derivative of any of such L-amino acids. In certain instances $R^4$ is a dipeptide or an N-acyl derivative thereof. In certain instances R is a tripeptide or an N-acyl derivative thereof.

In formula KC-(I), $R^4$ is

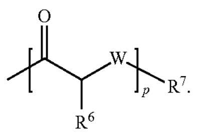

In formula KC-(I), each $R^6$ can be independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring.

In certain instances, in formula KC-(I), $R^6$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl. In certain instances, $R^6$ is selected from hydrogen, alkyl, substituted alkyl, arylalkyl, substituted arylalkyl, heteroarylalkyl, and substituted heteroarylalkyl. In certain instances, $R^6$ is hydrogen. In certain instances, $R^6$ is alkyl. In certain instances, $R^6$ is substituted alkyl. In certain instances, $R^6$ is arylalkyl or substituted arylalkyl. In certain instances, $R^6$ is heteroarylalkyl or substituted heteroarylalkyl.

In certain instances, $R^6$ is a side chain of an amino acid, such as alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine or valine. In certain instances, $R^6$ is a side chain of an L-amino acid, such as L-alanine, L-arginine, L-asparagine, L-aspartic acid, L-cysteine, L-glycine, L-glutamine, L-glutamic acid, L-histidine, L-isoleucine, L-leucine, L-lysine, L-methionine, L-phenylalanine, L-proline, L-serine, L-threonine, L-tryptophan, L-tyrosine or L-valine.

In certain instances, $R^6$ is $-CH_2CH_2CH_2NH(C{=}NH)NH_2$ or $-CH_2CH_2CH_2CH_2NH_2$.

In formula KC-(I), each W can be independently $-NR^8-$, $-O-$ or $-S-$. In certain instances, W is $-NR^8-$. In certain instances, W is $-O-$. In certain instances, W is $-S-$.

In formula KC-(I), each $R^8$ can be independently hydrogen, alkyl, substituted alkyl, aryl or substituted aryl, or optionally, each $R^6$ and $R^8$ independently together with the atoms to which they are bonded form a cycloheteroalkyl or substituted cycloheteroalkyl ring.

In certain instances, in formula KC-(I), $R^8$ is hydrogen or alkyl. In certain instances, $R^8$ is hydrogen. In certain instances, $R^8$ is alkyl. In certain instances, $R^8$ is aryl. In certain instances, $R^6$ and $R^8$ independently together with the atoms to which they are bonded form a cycloheteroalkyl or substituted cycloheteroalkyl ring.

In formula KC-(I), p can be an integer from one to 100 and each $R^6$ can be selected independently from a side chain of any amino acid. In certain instances, p is an integer from one to 50. In certain instances, p is an integer from one to 90, 80, 70, 60, 50, 40, 30, 20, or 10. In certain instances, p is about 100. In certain instances, p is about 75. In certain instances, p is about 50. In certain instances, p is about 25. In certain instances, p is about 20. In certain instances, p is about 15. In certain instances, p is about 10. In certain instances, p is about 9. In certain instances, p is about 8. In certain instances, p is about 7. In certain instances, p is about 6. In certain instances, p is about 5. In certain instances, p is about 4. In certain instances, p is about 3. In certain instances, p is about 2. In certain instances, p is about one.

In certain instances, the $R^6$ of $R^4$ adjacent to the nitrogen of $—N(R^3)(R^4)$ is $—CH_2CH_2CH_2NH(C{=}NH)NH_2$ or $—CH_2CH_2CH_2CH_2NH_2$, and any additional $R^6$ can be a side chain of any amino acid independently selected from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine or valine.

In formula KC-(I), $R^7$ can be selected from hydrogen, alkyl, substituted alkyl, acyl, substituted acyl, alkoxycarbonyl, substituted alkoxycarbonyl, aryl, substituted aryl, arylalkyl, and substituted arylalkyl.

In certain instances, $R^7$ is hydrogen, alkyl, acyl, or substituted acyl. In certain instances, $R^7$ is hydrogen. In certain instances, $R^7$ is alkyl. In certain instances, $R^7$ is acyl or substituted acyl. In certain instances, $R^7$ is acyl. In certain instances, $R^7$ is substituted acyl. In certain instances, $R^7$ can be acetyl, benzoyl, malonyl, piperonyl or succinyl.

Formula KC-(II)

Compounds of formula KC-(II) are compounds of formula KC-(I) in which $R^5$ is selected from (1-6C) alkyl, (1-6C) substituted alkyl, $—(CH_2)_q(C_6H_4)—COOH$, $—(CH_2)_q(C_6H_4)—COOCH_3$, and $—(CH_2)_q(C_6H_4)—COOCH_2CH_3$, where q is an integer from one to 10; n is 2 or 3; $R^3$ is hydrogen; $R^4$ is an L-amino acid or peptide, where the peptide can be comprised of L-amino acids. In one of its composition aspects, the present embodiments provide a compound of formula KC-(II):

(KC-(II))

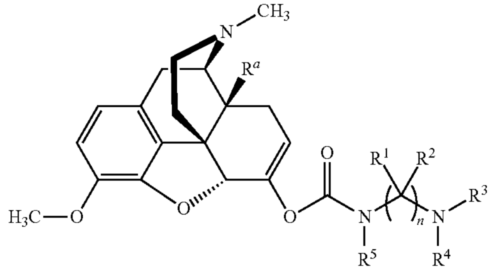

wherein:

$R^a$ is hydrogen or hydroxyl;

$R^5$ is selected from (1-6C)alkyl, (1-6C) substituted alkyl, $—(CH_2)_q(C_6H_4)—COOH$, $—(CH_2)_q(C_6H_4)—COOCH_3$, and $—(CH_2)_q(C_6H_4)—COOCH_2CH_3$, where q is an integer from one to 10;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl or substituted cycloalkyl group, or two $R^1$ or $R^2$ groups on adjacent carbon atoms, together with the carbon atoms to which they are attached, form a cycloalkyl or substituted cycloalkyl group;

n is 2 or 3;

$R^3$ is hydrogen;

$R^4$ is a residue of an L-amino acid selected from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine, or a residue of an N-acyl derivative of any of said amino acids; or a residue of a peptide composed of at least two L-amino acid residues selected independently from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine or a residue of an N-acyl derivative thereof.

In certain embodiments in Formula KC-(II), $R^4$ is a residue of an L-amino acid selected from arginine and lysine.

In certain instances, in formula KC-(II), when $R^4$ is a peptide comprising more than one amino acid, then the $R^4$ adjacent to the nitrogen of $—N(R^3)(R^4)$ is a residue of L-arginine or L-lysine. In certain instances $R^4$ is a dipeptide or an N-acyl derivative thereof. In certain instances $R^4$ is a tripeptide or an N-acyl derivative thereof.

In certain embodiments in Formula KC-(II), $R^4$ is a residue of an N-acyl derivative thereof. In certain instances, $R^4$ is a residue of an N-acyl derivative thereof, where the N-acyl derivative is substituted, such as, but not limited to, malonyl and succinyl.

Formula KC-(III)

In one of its composition aspects, the present embodiments provide a compound of formula KC-(IIIa):

(KC-(IIIa))

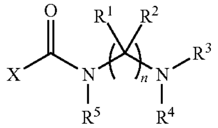

wherein:

X represents a residue of a ketone-containing opioid, wherein the hydrogen atom of the corresponding enolic group of the ketone is replaced by a covalent bond to $—C(O)—NR^5—(C(R^1)(R^2))_n—NR^3R^4$;

$R^5$ is selected from alkyl, substituted alkyl, arylalkyl, substituted arylalkyl, aryl and substituted aryl;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl, substituted cycloalkyl, aryl, or substituted aryl group, or two $R^2$ or $R^3$ groups on adjacent carbon atoms, together with the carbon atoms to which they are attached, form a cycloalkyl, substituted cycloalkyl, aryl, or substituted aryl group;

n is an integer from 2 to 4;

$R^3$ is hydrogen;

$R^4$ is

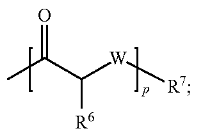

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;

each W is independently —$NR^8$—, —O— or —S—;

each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

p is an integer from one to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

In one of its composition aspects, the present embodiments provide a compound of formula KC-(IIIb):

(KC-(IIIb))

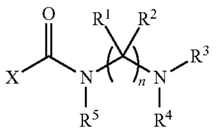

wherein:

X represents a residue of a ketone-containing opioid, wherein the hydrogen atom of the corresponding enolic group of the ketone is replaced by a covalent bond to —C(O)—$NR^5$—$(C(R^1)(R^2))_n$—$NR^3R^4$;

$R^5$ is selected from alkyl, substituted alkyl, arylalkyl, substituted arylalkyl, aryl and substituted aryl;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl or substituted cycloalkyl group, or two $R^1$ or $R^2$ groups on adjacent carbon atoms, together with the carbon atoms to which they are attached, form a cycloalkyl or substituted cycloalkyl group;

n is an integer from 2 to 4;

$R^3$ is hydrogen;

$R^4$ is

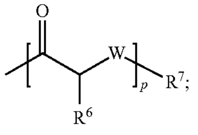

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;

each W is independently —$NR^8$—, —O— or —S—;

each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

p is an integer from one to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

Reference to formula KC-(III) is meant to include compounds of formula KC-(IIIa) and KC-(IIIb).

In formula KC-(III), $R^5$ can be selected from alkyl, substituted alkyl, arylalkyl, substituted arylalkyl, aryl and substituted aryl. In certain instances, $R^5$ is (1-6C)alkyl. In other instances, $R^5$ is (1-4C)alkyl. In other instances, $R^5$ is methyl or ethyl. In other instances, $R^5$ is methyl. In certain instances, $R^5$ is ethyl.

In certain instances, $R^5$ is substituted alkyl. In certain instances, $R^5$ is an alkyl group substituted with a carboxylic group such as a carboxylic acid, carboxylic ester or carboxylic amide. In certain instances, $R^5$ is —$(CH_2)_n$—COOH, —$(CH_2)_n$—$COOCH_3$, or —$(CH_2)_n$—$COOCH_2CH_3$, wherein n is a number form one to 10. In certain instances, $R^1$ is —$(CH_2)_5$—COOH, —$(CH_2)_5$—$COOCH_3$, or —$(CH_2)_5$—$COOCH_2CH_3$.

In certain instances, in formula KC-(III), $R^5$ is arylalkyl or substituted arylalkyl. In certain instances, in formula KC-(III), $R^5$ is arylalkyl. In certain instances, $R^5$ is substituted arylalkyl. In certain instances, $R^5$ is an arylalkyl group substituted with a carboxylic group such as a carboxylic acid, carboxylic ester or carboxylic amide. In certain instances, $R^5$ is —$(CH_2)_q(C_6H_4)$—COOH, —$(CH_2)_q(C_6H_4)$—$COOCH_3$, or —$(CH_2)_q(C_6H_4)$—$COOCH_2CH_3$, where q is an integer from one to 10. In certain instances, $R^5$ is —$CH_2(C_6H_4)$—COOH, —$CH_2(C_6H_4)$—$COOCH_3$, or —$CH_2$ $(C_6H_4)$—$COOCH_2CH_3$.

In certain instances, in formula KC-(III), $R^5$ is aryl. In certain instances, $R^5$ is substituted aryl. In certain instances, $R^5$ is an aryl group ortho, meta or para-substituted with a carboxylic group such as a carboxylic acid, carboxylic ester or carboxylic amide. In certain instances, $R^5$ is —$(C_6H_4)$—COOH, —$(C_6H_4)$—$COOCH_3$, or —$(C_6H_4)$—$COOCH_2CH_3$.

In formula KC-(III), each $R^1$ can be independently selected from hydrogen, alkyl, substituted alkyl, aryl, substituted aryl, acyl, and aminoacyl. In certain instances, $R^1$ is hydrogen or alkyl. In certain instances, $R^1$ is hydrogen. In certain instances, $R^1$ is alkyl. In certain instances, $R^1$ is acyl. In certain instances, $R^1$ is aminoacyl.

In formula KC-(III), each $R^2$ can be independently selected from hydrogen, alkyl, substituted alkyl, aryl, substituted aryl, acyl, and aminoacyl. In certain instances, $R^2$ is hydrogen or alkyl. In certain instances, $R^2$ is hydrogen. In certain instances, $R^2$ is alkyl. In certain instances, $R^2$ is acyl. In certain instances, $R^2$ is aminoacyl.

In certain instances, $R^1$ and $R^2$ are hydrogen. In certain instances, $R^1$ and $R^2$ on the same carbon are both alkyl. In certain instances, $R^1$ and $R^2$ on the same carbon are methyl. In certain instances, $R^1$ and $R^2$ on the same carbon are ethyl.

In certain instances, $R^1$ and $R^1$ which are vicinal are both alkyl and $R^2$ and $R^2$ which are vicinal are both hydrogen. In certain instances, $R^1$ and $R^1$ which are vicinal are both ethyl and $R^2$ and $R^2$ which are vicinal are both hydrogen. In certain instances, $R^1$ and $R^1$ which are vicinal are both methyl and $R^2$ and $R^2$ which are vicinal are both hydrogen.

In certain instances, in the chain of —$[C(R^1)(R^2)]_n$— in Formula KC-(III), not every carbon is substituted. In certain instances, in the chain of —$[C(R^1)(R^2)]_n$—, there is a combination of different alkyl substituents, such as methyl or ethyl.

In certain instances, one of $R^1$ and $R^2$ is methyl, ethyl or other alkyl and $R^5$ is alkyl. In certain instances, $R^1$ and $R^1$ which are vicinal are both alkyl and $R^2$ and $R^2$ which are vicinal are both hydrogen and $R^5$ is alkyl. In certain instances, $R^1$ and $R^1$ which are vicinal are both ethyl and $R^2$ and $R^2$ which are vicinal are both hydrogen and $R^5$ is alkyl. In certain instances, $R^1$ and $R^1$ which are vicinal are both methyl and $R^2$ and $R^2$ which are vicinal are both hydrogen and $R^5$ is alkyl.

In certain instances, one of $R^1$ and $R^2$ is methyl, ethyl or other alkyl and $R^5$ is substituted alkyl. In certain instances, one of $R^1$ and $R^2$ is methyl, ethyl or other alkyl and $R^5$ is an alkyl group substituted with a carboxylic group such as a carboxylic acid, carboxylic ester or carboxylic amide. In certain instances, one of $R^1$ and $R^2$ is methyl, ethyl or other alkyl and $R^5$ is —$(CH_2)_q(C_6H_4)$—COOH, —$(CH_2)_q(C_6H_4)$—$COOCH_3$, or —$(CH_2)_q(C_6H_4)$—$COOCH_2CH_3$, where q is an integer from one to 10. In certain instances, one of $R^1$ and $R^2$ is methyl, ethyl or other alkyl and $R^5$ is an alkyl group substituted with carboxamide.

In formula KC-(III), $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group. In certain instances, $R^1$ and $R^2$ together with the carbon to which they are attached can form a cycloalkyl group. Thus, in certain instances, $R^1$ and $R^2$ on the same carbon form a spirocycle. In certain instances, $R^1$ and $R^2$ together with the carbon to which they are attached can form a substituted cycloalkyl group. In certain instances, two $R^1$ or $R^2$ groups on adjacent carbon atoms, together with the carbon atoms to which they are attached, can form a cycloalkyl group. In certain instances, two $R^1$ or $R^2$ groups on adjacent carbon atoms, together with the carbon atoms to which they are attached, can form a substituted cycloalkyl group.

In certain instances, $R^1$ and $R^2$ together with the carbon to which they are attached can form an aryl or substituted aryl group, or two $R^1$ or $R^2$ groups on adjacent carbon atoms, together with the carbon atoms to which they are attached, can form an aryl or substituted aryl group. In certain instances, two $R^1$ or $R^2$ groups on adjacent carbon atoms, together with the carbon atoms to which they are attached, form a phenyl ring. In certain instances, two $R^1$ or $R^2$ groups on adjacent carbon atoms, together with the carbon atoms to which they are attached, form a substituted phenyl ring. In certain instances, two $R^1$ or $R^2$ groups on adjacent carbon atoms, together with the carbon atoms to which they are attached, form a naphthyl ring.

In certain instances, one of $R^1$ and $R^2$ is aminoacyl.

In certain instances, one or both of $R^1$ and $R^2$ is aminoacyl comprising phenylenediamine. In certain instances, one of $R^1$ and $R^2$ is

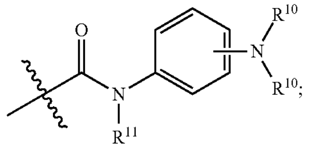

wherein each $R^{10}$ is independently selected from hydrogen, alkyl, substituted alkyl, and acyl and $R^{10}$ is alkyl or substituted alkyl. In certain instances, at least one of $R^{10}$ is acyl. In certain instances, at least one of $R^{10}$ is alkyl or substituted alkyl. In certain instances, at least one of $R^{10}$ is hydrogen. In certain instances, both of $R^{10}$ are hydrogen.

In certain instances, one of $R^1$ and $R^2$ is

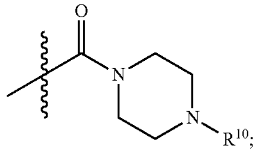

wherein $R^{10}$ is hydrogen, alkyl, substituted alkyl, or acyl. In certain instances, $R^{10}$ is acyl. In certain instances, $R^{10}$ is alkyl or substituted alkyl. In certain instances, $R^{10}$ is hydrogen.

In certain instances, one of $R^1$ and $R^2$ is

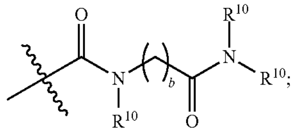

wherein each $R^{10}$ is independently hydrogen, alkyl, substituted alkyl, or acyl and b is a number from one to 5. In certain instances, one of $R^1$ and $R^2$ is

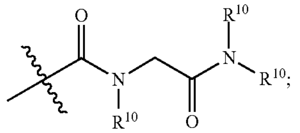

wherein each $R^{10}$ is independently hydrogen, alkyl, substituted alkyl, or acyl. In certain instances, one of $R^1$ and $R^2$ is

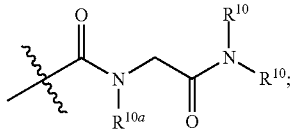

wherein $R^{10a}$ is alkyl and each $R^{10}$ is independently hydrogen, alkyl, substituted alkyl, or acyl.

In certain instances, one of $R^1$ and $R^2$ is

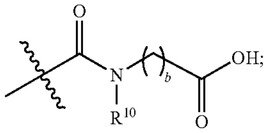

wherein $R^{10}$ is independently hydrogen, alkyl, substituted alkyl, or acyl and b is a number from one to 5. In certain instances, one of $R^1$ and $R^2$ is

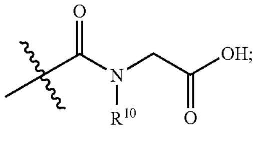

wherein $R^{10}$ is independently hydrogen, alkyl, substituted alkyl, or acyl.

In certain instances, one of $R^1$ and $R^2$ is an aminoacyl group, such as —C(O)$NR^{10a}R^{10b}$, wherein each $R^{10a}$ and $R^{10b}$ is independently selected from hydrogen, alkyl, substituted alkyl, and acyl. In certain instances, one of $R^1$ and $R^2$ is an aminoacyl group, such as —C(O)$NR^{10a}R^{10b}$, wherein $R^{10a}$ is an alkyl and $R^{10b}$ is substituted alkyl. In certain instances, one of $R^1$ and $R^2$ is an aminoacyl group, such as —C(O)$NR^{10a}R^{10b}$, wherein $R^{10a}$ is an alkyl and $R^{10b}$ is alkyl substituted with a carboxylic acid or carboxyl ester. In certain instances, one of $R^1$ and $R^2$ is an aminoacyl group, such as —C(O)$NR^{10a}R^{10b}$, wherein $R^{10a}$ is methyl and $R^{10b}$ is alkyl substituted with a carboxylic acid or carboxyl ester.

In certain instances, $R^1$ or $R^2$ can modulate a rate of intramolecular cyclization. $R^1$ or $R^2$ can speed up a rate of intramolecular cyclization, when compared to the corresponding molecule where $R^1$ and $R^2$ are both hydrogen. In certain instances, $R^1$ or $R^2$ comprise an electron-withdrawing group or an electron-donating group. In certain instances, $R^1$ or $R^2$ comprise an electron-withdrawing group. In certain instances, $R^1$ or $R^2$ comprise an electron-donating group.

Atoms and groups capable of functioning as electron withdrawing substituents are well known in the field of organic chemistry. They include electronegative atoms and groups containing electronegative atoms. Such groups function to lower the basicity or protonation state of a nucleophilic nitrogen in the beta position via inductive withdrawal of electron density. Such groups can also be positioned on other positions along the alkylene chain. Examples include halogen atoms (for example, a fluorine atom), acyl groups (for example an alkanoyl group, an aroyl group, a carboxyl group, an alkoxycarbonyl group, an aryloxycarbonyl group or an aminocarbonyl group (such as a carbamoyl, alkylaminocarbonyl, dialkylaminocarbonyl or arylaminocarbonyl group)), an oxo (=O) substituent, a nitrile group, a nitro group, ether groups (for example an alkoxy group) and phenyl groups bearing a substituent at the ortho position, the para position or both the ortho and the para positions, each substituent being selected independently from a halogen atom, a fluoroalkyl group (such as trifluoromethyl), a nitro group, a cyano group and a carboxyl group. Each of the electron withdrawing substituents can be selected independently from these.

In certain instances, —$[C(R^1)(R^2)]_n$— is selected from —$CH(CH_2F)CH(CH_2F)$—; —$CH(CHF_2)CH(CHF_2)$—; —$CH(CF_3)CH(CF_3)$—; —$CH_2CH(CF_3)$—; —$CH_2CH(CHF_2)$—; —$CH_2CH(CH_2F)$—; —$CH_2CH(F)CH_2$—; —$CH_2C(F_2)CH_2$—; —$CH_2CH(C(O)NR^{20}R^{21})$—; —$CH_2CH(C(O)OR^{22})$—; —$CH_2CH(C(O)OH)$—; —$CH(CH_2F)CH_2CH(CH_2F)$—; —$CH(CHF_2)CH_2CH(CHF_2)$—; —$CH(CF_3)CH_2CH(CF_3)$—; —$CH_2CH_2CH(CF_3)$—; —$CH_2CH_2CH(CHF_2)$—; —$CH_2CH_2CH(CH_2F)$—; —$CH_2CH_2CH(C(O)\ NR^{23}R^{24})$—; —$CH_2CH_2CH(C(O)OR^{25})$—; and —$CH_2CH_2CH(C(O)OH)$—, in which $R^{20}$, $R^{21}$, $R^{22}$ and $R^{23}$ each independently represents hydrogen or (1-6C)alkyl, and $R^{24}$ and $R^{25}$ each independently represents (1-6C)alkyl.

In formula KC-(III), n can be an integer from 2 to 6. In certain instances, n is two. In other instances, n is three. In other instances, n is four.

In formula KC-(III), $R^3$ can be hydrogen or (1-4C)alkyl. In certain instances, $R^3$ is hydrogen or methyl. In certain instances, $R^3$ is hydrogen. In certain instances, $R^3$ is methyl. In certain instances, $R^3$ is ethyl. In certain instances, $R^3$ is propyl or butyl.

In formula KC-(III), $R^4$ can be a residue of an L-amino acid selected from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine, or a residue of an N-acyl derivative of any of said amino acids; or a residue of a peptide composed of at least two L-amino acid residues selected independently from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine or a residue of an N-acyl derivative thereof. Such a peptide can be from 2 to about 100 amino acids in length. Examples of N-acyl derivatives include formyl, acetyl, benzoyl, malonyl, piperonyl, propionyl or succinyl derivatives.

In certain instances, $R^4$ is a residue of L-arginine or L-lysine, or a residue of an N-acyl derivative of L-arginine or L-lysine.

In certain instances, in formula KC-(III), when p is greater than one, then the $R^4$ adjacent to the nitrogen of —$N(R^3)(R^4)$ is a residue of L-arginine or L-lysine. In certain instances, when p is greater than one, the $R^4$ adjacent to the nitrogen of —$N(R^3)(R^4)$ is a residue of L-arginine or L-lysine and the first residue is joined to at least one additional L-amino acid residue selected independently from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine. The terminal residue of the peptide can be an N-acyl derivative of any of such amino acids. In certain instances $R^4$ is a dipeptide or an N-acyl derivative thereof. In certain instances R is a tripeptide or an N-acyl derivative thereof. In formula KC-(III), $R^4$ is

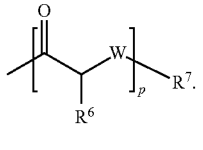

In formula KC-(III), each $R^6$ can be independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring.

In certain instances, in formula KC-(III), $R^6$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl. In certain instances, $R^6$ is selected from hydrogen, alkyl, substituted alkyl, arylalkyl, substituted arylalkyl, heteroarylalkyl, and substituted heteroarylalkyl. In certain instances, $R^6$ is hydrogen. In certain instances, $R^6$ is alkyl. In certain instances, $R^6$ is substituted alkyl. In certain instances, $R^6$ is arylalkyl or substituted arylalkyl. In certain instances, $R^6$ is heteroarylalkyl or substituted heteroarylalkyl.

In certain instances, $R^6$ is a side chain of an amino acid, such as alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine or valine. In certain instances, $R^6$ is a side chain of an L-amino acid, such as L-alanine, L-arginine, L-asparagine, L-aspartic acid, L-cysteine, L-glycine, L-glutamine, L-glutamic acid, L-histidine, L-isoleucine, L-leucine, L-lysine, L-methionine, L-phenylalanine, L-proline, L-serine, L-threonine, L-tryptophan, L-tyrosine or L-valine.

In certain instances, $R^6$ is $—CH_2CH_2CH_2NH(C{=}NH)NH_2$ or $—CH_2CH_2CH_2CH_2NH_2$.

In formula KC-(III), each W can be independently $—NR^8—$, —O— or —S—. In certain instances, W is $—NR^8—$. In certain instances, W is —O—. In certain instances, W is —S—.

In formula KC-(III), each $R^8$ can be independently hydrogen, alkyl, substituted alkyl, aryl or substituted aryl, or optionally, each $R^6$ and $R^8$ independently together with the atoms to which they are bonded form a cycloheteroalkyl or substituted cycloheteroalkyl ring.

In certain instances, in formula KC-(III), $R^8$ is hydrogen or alkyl. In certain instances, $R^8$ is hydrogen. In certain instances, $R^8$ is alkyl. In certain instances, $R^8$ is aryl. In certain instances, $R^6$ and $R^8$ independently together with the atoms to which they are bonded form a cycloheteroalkyl or substituted cycloheteroalkyl ring.

In formula KC-(III), p can be an integer from one to 100 and each $R^6$ can be selected independently from a side chain of any amino acid. In certain instances, p is an integer from one to 50. In certain instances, p is an integer from one to 90, 80, 70, 60, 50, 40, 30, 20, or 10. In certain instances, p is about 100. In certain instances, p is about 75. In certain instances, p is about 50. In certain instances, p is about 25. In certain instances, p is about 20. In certain instances, p is about 15. In certain instances, p is about 10. In certain instances, p is about 9. In certain instances, p is about 8. In certain instances, p is about 7. In certain instances, p is about 6. In certain instances, p is about 5. In certain instances, p is about 4. In certain instances, p is about 3. In certain instances, p is about 2. In certain instances, p is about one.

In certain instances, the $R^6$ of $R^4$ adjacent to the nitrogen of $—N(R^3)(R^4)$ is $—CH_2CH_2CH_2NH(C{=}NH)NH_2$ or $—CH_2CH_2CH_2CH_2NH_2$, and any additional $R^6$ can be a side chain of any amino acid independently selected from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine or valine.

In formula KC-(III), $R^7$ can be selected from hydrogen, alkyl, substituted alkyl, acyl, substituted acyl, alkoxycarbonyl, substituted alkoxycarbonyl, aryl, substituted aryl, arylalkyl, and substituted arylalkyl.

In certain instances, $R^7$ is hydrogen, alkyl, acyl, or substituted acyl. In certain instances, $R^7$ is hydrogen. In certain instances, $R^7$ is alkyl. In certain instances, $R^7$ is acyl or substituted acyl. In certain instances, $R^7$ is acyl. In certain instances, $R^7$ is substituted acyl. In certain instances, $R^7$ can be formyl, acetyl, benzoyl, malonyl, piperonyl, propionyl or succinyl.

In certain embodiments, the ketone-modified opioid prodrug is Compound KC-8 (N-1-[3-(oxycodone-6-enol-carbonyl-methyl-amino)-2,2-dimethyl-propylamine]-arginine-glycine-malonic acid), shown below:

(KC-8)

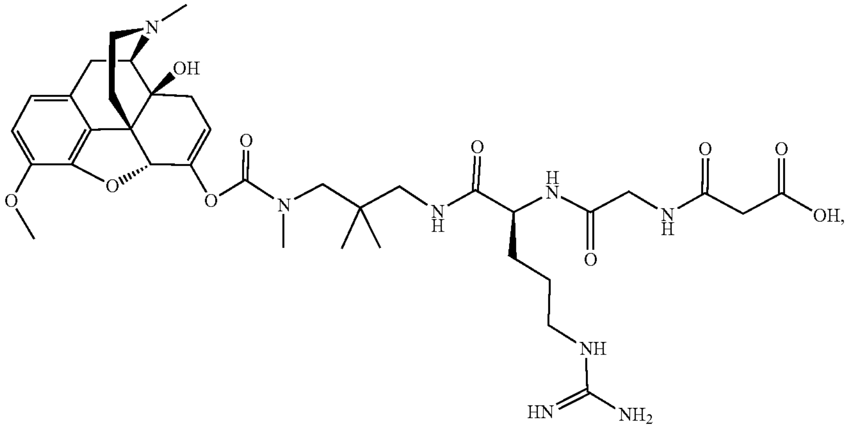

or acceptable salts, solvates, and hydrates thereof. Compound KC-8 is an active agent prodrug that provides controlled release of oxycodone.

In certain embodiments, the ketone-modified opioid prodrug is Compound KC-7 (N-1-[(S)-2-(oxycodone-6-enol-carbonyl-methyl-amino)-2-carbonyl-sarcosine-ethyl amine]-arginine-glycine-acetate), shown below:

(KC-7)

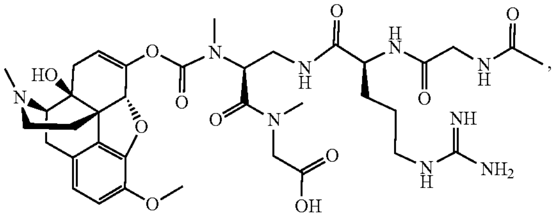

or acceptable salts, solvates, and hydrates thereof. Compound KC-7 is an active agent prodrug that provides controlled release of oxycodone.

In some embodiments, the ketone-modified opioid prodrugs include those described in International Patent Publication Nos. WO 2011/031350; WO 2012/096887; WO 2012/096886 and WO 2011/133149, the disclosures of which are herein incorporated by reference.

Amphetamine Prodrugs

The disclosure provides amphetamine prodrugs which provide enzymatically-controlled release of amphetamine. In an amphetamine prodrug, a promoiety is attached to the amphetamine via modification of the amino group. Amphetamine refers to a chemical substance that exerts its pharmacological action by modulating neurotransmitters, such as dopamine, serotonin and norepinephrine. In certain embodiments, amphetamine is a compound with a pharmacophore that crosses the blood-brain barrier and has CNS stimulation and central appetite suppressant effects. See, for example, Foye's Principles of Medicinal Chemistry, Sixth Edition, ed. T. L. Lemke and D. A. Williams, Lippincott Williams & Wilkins, 2008, particularly Chapter 13, pages 392-416.

"Amino-containing amphetamine analogs" or amphetamine analogs" refer to analogs or derivatives of amphetamine that contain an amino group. For instance, the following amphetamine analogs contain an amino group that can be a point of attachment to a promoiety through the amino group: Benzedrine (i.e., dl-amphetamine), dextroamphetamine (i.e., d-amphetamine), levoamphetamine (i.e., i-amphetamine), 4-fluoroamphetamine (4-FA), 3-fluoroamphetamine (3-FA), 2-fluoroamphetamine (2-FA), 4-methylthioamphetamine (4-MTA), 3,4-methylenedioxyamphetamine (MDA), para-methoxyamphetamine (PMA), 3-methoxyamphetamine (3-MeOA), 4-ethoxyamphetamine (4-ETA), 2,5-dimethoxy-4-ethoxyamphetamine (MEM), 2,5-dimethoxy-4-propoxyamphetamine (MPM), 4-methylamphetamine (4-MA), 2-methylamphetamine (2-MA), 3-methylamphetamine (3-MA), 3,4-dimethylamphetamine, 3-methoxy-4-methylamphetamine (MMA), 3-trifluoromethylamphetamine, 3-hydroxyamphetamine, 4-hydroxyamphetamine, (1R,2S)-3-[2-amino-1-hydroxy-propyl]phenol, 2,5-dimethoxy-4-methylamphetamine (DOM), 2,6-dimethoxy-4-methylamphetamine (Ψ-DOM), indanylamphetamine, 5-(2-aminopropyl)-2,3-dihydrobenzofuran (5-APDB), 6-(2-aminopropyl)-2,3-dihydrobenzofuran (6-APDB), 5-(2-aminopropyl)indole (5-IT), naphthylaminopropane (NAP), phenylpropanolamine (PPA), d-norpseudoephedrine, benzoylethanamine, para-bromoamphetamine (PBA), para-chloroamphetamine (PCA), para-iodoamphetamine (PIA), a, 0-dimethylamphetamine, o-chloro-α,α-dimethylphenethylamine, 3,4-dihydroxyamphetamine (3,4-DHA), 2,4-dimethoxyamphetamine (2,4-DMA), 2,5-dimethoxyamphetamine (2,5-DMA), 3,4-dimethoxyamphetamine (3,4-DMA), a-methylnorepinephrine (a-Me-NE), 2,5-dimethoxy-4-methylthioamphetamine (Aleph), 2,5-dimethoxy-4-ethylthioamphetamine (Aleph-2), 2,5-dimethoxy-4-isopropylthioamphetamine (Aleph-4), 2,5-dimethoxy-4-phenylthioamphetamine (Aleph-6), 2,5-dimethoxy-4-propylthioamphetamine (Aleph-7), 2,5-dimethoxy-bromoamphetamine (DOB), 2,5-dimethoxychloroamphetamine (DOC), 2,5-dimethoxyfluoroethylamphetamine (DOEF) 2,5-dimethoxyethylamphetamine (DOET), 2,5-dimethoxyfluoroamphetamine (DOF), 2,5-dimethoxyiodoamphetamine (DOI), 2,5-dimethoxynitroamphetamine (DON), 2,5-dimethoxypropylamphetamine (DOPR), 2,5-dimethoxytrifluoromethylamphetamine (DOTFM), 2-methyl-3,4-methylenedioxyamphetamine (2-methyl-MDA), 3-methyl-4,5-methylenedioxyamphetamine (5-methyl-MDA), 3-methoxy-4,5-methylenedioxyamphetamine (MMDA), 2-methoxy-4,5-methylenedioxyamphetamine (MMDA-2), 2-methoxy-3,4-methylenedioxyamphetamine (MMDA-3a), 4-methoxy-2,3-methylenedioxyamphetamine (MMDA-3b), 2-methylthio-3,4-methylenethioxyamphetamine (2T-MMDA-3a), 2-methoxy-4,5-methylenethioxyamphetamine (4T-MMDA-2), 3,4,5-trimethoxyamphetamine (TMA), 2,4,5-trimethoxyamphetamine (TMA-2), 2,3,4-trimethoxyamphetamine (TMA-3), 2,3,5-trimethoxyamphetamine (TMA-4), 2,3,6-trimethoxyamphetamine (TMA-5), 2,4,6-trimethoxyamphetamine (TMA-6), 2,5-dimethoxy-3,4-dimethylamphetamine, 2,5-dimethoxy-3,4-methylenedioxyamphetamine (DMMDA), tyramine, phentermine, alpha-allyl-phenethylamine, (1-(8-bromobenzo[1,2-b;4,5-b]difuran-4-yl)-2-aminopropane (bromo-DragonFLY), 3,4,5-trimethoxyphenethylamine (mescaline), 2,5-dimethoxy-4-bromophenethylamine (2C-B), 2,5-dimethoxy-4-chlorophenethylamine (2C-C), 2,5-dimethoxy-4-iodophenethylamine (2C-I), 2,5-dimethoxy-4-methyl-phenethylamine (2C-D), 2,5-dimethoxy-4-ethylphenethylamine (2C-E), 2,5-dimethoxy-4-n-propylphenethylamine (2C-P), 2,5-dimethoxy-4-fluorophenethylamine (2C-F), 2,5-dimethoxy-4-nitrophenethylamine (2C-N), 2,5-dimethoxy-4-ethylthio-phenethylamine (2C-T-2), 2,5-dimethoxy-4-isopropylthio-phenethylamine (2C-T-4), 2,5-dimethoxy-4-propylthio-phenethylamine (2C-T-7), 2,5-dimethoxy-4-cyclopropylmethylthio-phenethylamine (2C-T-8), 2,5-dimethoxy-4-tert-butylthio-phenethylamine (2C-T-9), 2,5-dimethoxy-4-(2-fluoroethylthio)-phenethylamine (2C-T-21), ephedrine, pseudoephedrine, and the like.

Formula AM-(I)

The present disclosure provides amphetamine prodrugs in which the promoiety is attached through the amino group of amphetamine. The disclosure provides compounds of the general formula AM-(I):

AM-(I)

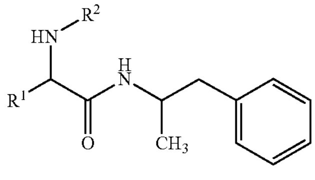

wherein $R^1$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl; and $R^2$ is an acyl, substituted acyl, or an N-acyl derivative of a peptide;

or a salt, hydrate or solvate thereof.

Formula AM-(H)

The embodiments include a compound of formula AM-(II):

AM-(II)

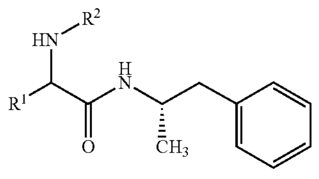

wherein $R^1$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl; and $R^2$ is an acyl, substituted acyl, or an N-acyl derivative of a peptide;

or a salt, hydrate or solvate thereof.

In formulae AM-(I) and AM-(II), $R^1$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl.

In certain instances, in formulae AM-(I) and AM-(II), $R^1$ is a side chain of an amino acid, such as alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine or valine. In certain instances, $R^1$ is a side chain of an L-amino acid, such as L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine or L-valine.

In certain instances, in formulae AM-(I) and AM-(II), $R^1$ is $—CH_2CH_2CH_2NH(C(=NH)(NH_2))$ or $—CH_2CH_2CH_2CH_2NH_2$. In certain instances, in formulae AM-(I) and AM-(II), $R^1$ is $—CH_2CH_2CH_2NH(C(=NH)(NH_2))$ or $—CH_2CH_2CH_2CH_2NH_2$, the configuration of the carbon atom to which $R^1$ is attached corresponding with that in an L-amino acid. In certain instances, in formulae AM-(I) and AM-(II), $R^1$ is $—CH_2CH_2CH_2NH(C(=NH)(NH_2))$, the configuration of the carbon atom to which $R^1$ is attached corresponding with that in an L-amino acid. In certain instances, in formulae AM-(I) and AM-(II), $R^1$ is $—CH_2CH_2CH_2CH_2NH_2$, the configuration of the carbon atom to which $R^1$ is attached corresponding with that in an L-amino acid.

In formulae AM-(I) and AM-(II), $R^2$ is an acyl, substituted acyl, or an N-acyl derivative of a peptide. In certain instances, $R^2$ is acyl. In certain instances, $R^2$ is substituted acyl. In certain instances, $R^2$ is acetyl, benzoyl, malonyl, piperonyl or succinyl. In certain instances, $R^2$ is acetyl, malonyl, or succinyl. In certain instances, $R^2$ is acetyl. In certain instances, $R^2$ is malonyl. In certain instances, $R^2$ is succinyl. In certain instances, $R^2$ is an N-acyl derivative of a peptide.

In certain instances, $R^2$ is a peptide of the formula $(R^4)_p$, wherein p is an integer from 1 to 100, and each $R^4$ is an independently selected amino acid, wherein the $R^4$ at the terminal end of the peptide is N-acylated. In certain instances, each $R^4$ is an independently selected L-amino acid. In certain instances, p is an integer from 1 to 90, 80, 70, 60, 50, 40, 30, 20, or 10. In certain instances, p is 1, 2, 3, 4, 5, 6, 7, 8, 9, or 10. In certain instances, the terminal end of the peptide is N-acylated, wherein the acyl group is acetyl, benzoyl, malonyl, piperonyl or succinyl. In certain instances, the terminal end of the peptide is N-acylated, wherein the acyl group is acetyl, malonyl, or succinyl. In certain instances, the terminal end of the peptide is N-acylated, wherein the acyl group is acetyl. In certain instances, the terminal end of the peptide is N-acylated, wherein the acyl group is malonyl. In certain instances, the terminal end of the peptide is N-acylated, wherein the acyl group is succinyl.

In certain embodiments, in formulae AM-(I) and AM-(II), $—C(O)—CH(R^1)—NHR^2$ is a GI enzyme-cleavable moiety. A GI enzyme-cleavable moiety is a structural moiety that is capable of being cleaved by a GI enzyme. In certain instances, a GI enzyme-cleavable moiety comprises a charged moiety that can fit into the active site of a GI enzyme and is able to orient the prodrug for cleavage at a scissile bond. For instance, the charged moiety can be a basic moiety that exists as a charged moiety at physiological pH.

For example, to form a GI enzyme-cleavable moiety, $R^1$ can include, but is not limited to, a side chain of lysine (such as L-lysine), a side chain of arginine (such as L-arginine), a side chain of homolysine, a side chain of homoarginine, and a side chain of ornithine. Other GI enzyme-cleavable moieties include, but are not limited to, arginine mimics, arginine homologues, arginine truncates, arginine with varying oxidation states (for instance, metabolites), lysine mimics, lysine homologues, lysine truncates, and lysine with varying oxidation states (for instance, metabolites). Examples of arginine and lysine mimics include arylguanidines, arylamidines (substituted benzamidines), benzylamines and (bicyclo[2.2.2]octan-1-yl)methanamine and derivatives thereof.

In formulae AM-(I) and AM-(II), $R^2$ is selected from acyl, substituted acyl, and N-acyl derivative of a peptide. In certain instances, in formulae AM-(I) and AM-(II), $R^2$ is an N-acyl derivative of a peptide. The peptide may include one to 100 amino acids, where each amino acid can be selected independently. In certain instances, there are one to 50 amino acids in the peptide. In certain instances, there are one to 90, 80, 70, 60, 50, 40, 30, 20, or 10 amino acids in the peptide. In certain instances, there are about 100 amino acids in the peptide. In certain instances, there are about 75 amino acids in the peptide. In certain instances, there are about 50 amino acids in the peptide. In certain instances, there are about 25 amino acids in the peptide. In certain instances, there are about 20 amino acids in the peptide. In certain instances, there are about 15 amino acids in the peptide. In certain instances, there are about 10 amino acids in the peptide. In certain instances, there are about 9 amino acids in the peptide. In certain instances, there are about 8 amino acids in the peptide. In certain instances, there are about 7 amino acids in the peptide. In certain instances, there are about 6 amino acids in the peptide. In certain instances, there are about 5 amino acids in the peptide. In certain instances, there are about 4 amino acids in the peptide. In certain instances, there are about 3 amino acids in the peptide. In certain instances, there are about 2 amino acids in the peptide. In certain instances, there is about 1 amino acid in the peptide.

In certain embodiments, in formulae AM-(I) and AM-(II), —C(O)—CH(R')—$NHR^2$ is a trypsin-cleavable moiety. A trypsin-cleavable moiety is a structural moiety that is capable of being cleaved by trypsin. In certain instances, a trypsin-cleavable moiety comprises a charged moiety that can fit into an active site of trypsin and is able to orient the prodrug for cleavage at a scissile bond. For instance, the charged moiety can be a basic moiety that exists as a charged moiety at physiological pH.

In certain embodiments, in formulae AM-(I) and AM-(II), $R^1$ represents a side chain of an amino acid or a derivative of a side chain of an amino acid that effects —C(O)—CH (R')—$NR^2$ to be a trypsin-cleavable moiety. A derivative refers to a substance that has been altered from another substance by modification, partial substitution, homologation, truncation, or a change in oxidation state.

For example, to form a trypsin-cleavable moiety, $R^1$ can include, but is not limited to, a side chain of lysine (such as L-lysine), arginine (such as L-arginine), homolysine, homoarginine, and ornithine. Other values for $R^1$ include, but are not limited to, arginine mimics, arginine homologues, arginine truncates, arginine with varying oxidation states (for instance, metabolites), lysine mimics, lysine homologues, lysine truncates, and lysine with varying oxidation states (for instance, metabolites). Examples of arginine and lysine mimics include arylguanidines, arylamidines (substituted benzamidines), benzylamines and (bicyclo [2.2.2]octan-1-yl)methanamine and derivatives thereof.

In certain instances, in formulae AM-(I) and AM-(II), $R^1$ represents —$CH_2CH_2CH_2NH(C(=NH)(NH_2))$ or —$CH_2CH_2CH_2CH_2NH_2$, the configuration of the carbon atom to which $R^1$ is attached corresponding with that in an L-amino acid.

In formulae AM-(I) and AM-(II), $R^2$ is selected from acyl, substituted acyl, and N-acyl derivative of a peptide. In certain instances, $R^2$ is an N-acyl derivative of an amino acid. In certain instances, $R^2$ is an N-acyl derivative of a peptide. The peptide may include one to 100 amino acids and where each amino acid can be selected independently, and where the terminal amino acid is an N-acyl amino acid. In certain instances, there are one to 50 amino acids in the peptide. In certain instances, there are one to 90, 80, 70, 60, 50, 40, 30, 20, or 10 amino acids in the peptide. In certain instances, there are about 100 amino acids in the peptide. In certain instances, there are about 75 amino acids in the peptide. In certain instances, there are about 50 amino acids in the peptide. In certain instances, there are about 25 amino acids in the peptide. In certain instances, there are about 20 amino acids in the peptide. In certain instances, there are about 15 amino acids in the peptide. In certain instances, there are about 10 amino acids in the peptide. In certain instances, there are about 9 amino acids in the peptide. In certain instances, there are about 8 amino acids in the peptide. In certain instances, there are about 7 amino acids in the peptide. In certain instances, there are about 6 amino acids in the peptide. In certain instances, there are about 5 amino acids in the peptide. In certain instances, there are about 4 amino acids in the peptide. In certain instances, there are about 3 amino acids in the peptide. In certain instances, there are about 2 amino acids in the peptide. In certain instances, there is about 1 amino acid in the peptide.

In certain embodiments, the amphetamine prodrug is a Compound AM-1 (Amphetamine-arginine-acetate), shown below:

Compound AM-1

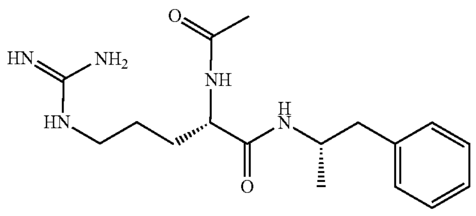

or a salt, hydrate or solvate thereof.

In certain embodiments, the amphetamine prodrug is a Compound AM-2 (Amphetamine-arginine-malonate), shown below:

Compound AM-2

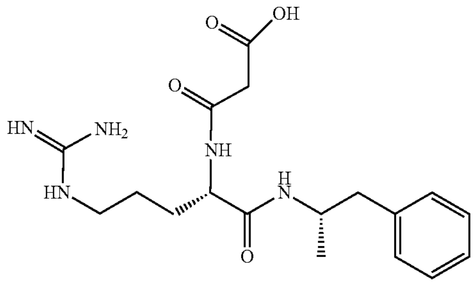

or a salt, hydrate or solvate thereof.

In certain embodiments, the amphetamine prodrug is a Compound AM-5 (Amphetamine-lysine-acetate), shown below:

Compound AM-5

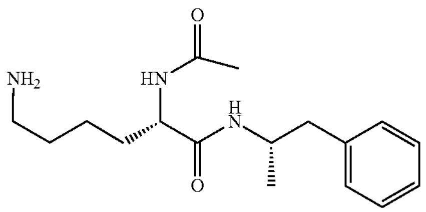

or a salt, hydrate or solvate thereof.

In certain embodiments, the amphetamine prodrug is a Compound AM-9 (Amphetamine-arginine-glycine-acetate), shown below:

(AM-9)

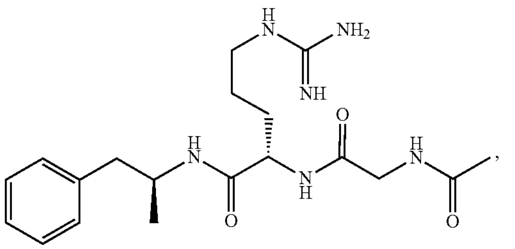

or a salt, hydrate or solvate thereof.

In certain embodiments, the amphetamine prodrug is a Compound AM-10 (Amphetamine-arginine-alanine-acetate), shown below:

(AM-10)

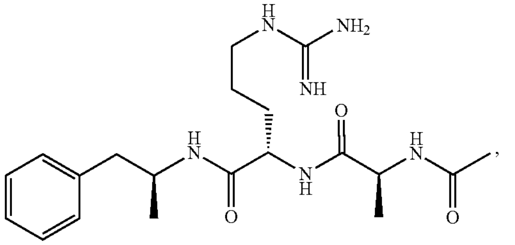

or a salt, hydrate or solvate thereof.

In some embodiments, the amphetamine prodrugs include those described in International Patent Publication Nos. WO 2011/133348 and WO 2020/181000, the disclosures of which are herein incorporated by reference.

Heterocyclic Linked Active Agent Prodrugs

Formula HC-(I)

Compounds of the present disclosure include compounds of formula HC-(I) shown below. Compositions of the present disclosure also include compounds of formula I shown below. Pharmaceutical compositions and methods of the present disclosure also contemplate compounds of formula I.

The present embodiments provide a compound of formula I:

HC-(I)

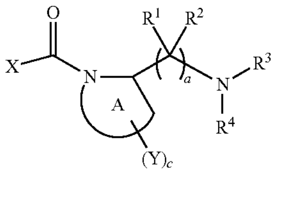

wherein

X is selected from a residue of a ketone-containing active agent, wherein the hydrogen atom of the corresponding hydroxyl group of the enolic tautomer of the ketone is replaced by a covalent bond to —C(O)—N[(A ring)-$Y_c$]—($CR^1R^2$)$_a$—NH—C(O)—CH($R^5$)—N($R^3$)—[C(O)—CH($R^6$)—N($R^3$)]$_b$—$R^7$; a residue of a phenolic active agent, wherein the hydrogen atom of the phenolic hydroxyl group is replaced by a covalent bond to —C(O)—N[(A ring)-$Y_c$]—($CR^1R^2$)$_a$—NH—C(O)—CH($R^5$)—N($R^3$)—[C(O)—CH($R^6$)—N($R^3$)]$_b$—$R^7$; and a residue of an amide-containing active agent, wherein —C(O)—N[(A ring)-$Y_c$]—($CR^1R^2$)$_a$—NH—C(O)—CH($R^5$)—N($R^3$)—[C(O)—CH($R^6$)—N($R^3$)]$_b$—$R^7$ is connected to the amide-containing active agent through the oxygen of the amide group, wherein the amide group is converted to an amide enol or an imine tautomer;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group;

a is an integer from one to 8;

provided that when a is one, the A ring is a heterocyclic 6 to 12-membered ring; and when the A ring is a heterocyclic 5-membered ring, then a is an integer from 2 to 8; each $R^3$ is independently hydrogen, alkyl, substituted alkyl, aryl or substituted aryl;

$R^4$ is

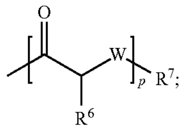

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;

each W is independently —$NR^8$—, —O— or —S—;

each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

p is an integer from one to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

In formula HC-(I), each $R^1$ can be independently selected from hydrogen, alkyl, substituted alkyl, aryl, substituted aryl, acyl, and aminoacyl. In certain instances, $R^1$ is hydrogen or alkyl. In certain instances, $R^1$ is hydrogen. In certain instances, $R^1$ is alkyl. In certain instances, $R^1$ is acyl. In certain instances, $R^1$ is aminoacyl.

In formula HC-(I), each $R^2$ can be independently selected from hydrogen, alkyl, substituted alkyl, aryl, substituted aryl, acyl, and aminoacyl. In certain instances, $R^2$ is hydrogen or alkyl. In certain instances, $R^2$ is hydrogen. In certain instances, $R^2$ is alkyl. In certain instances, $R^2$ is acyl. In certain instances, $R^2$ is aminoacyl.

In certain instances, $R^1$ and $R^2$ are hydrogen. In certain instances, $R^1$ and $R^2$ on the same carbon are both alkyl. In certain instances, $R^1$ and $R^2$ on the same carbon are methyl. In certain instances, $R^1$ and $R^2$ on the same carbon are ethyl.

In certain instances, $R^1$ and $R^1$ which are vicinal are both alkyl and $R^2$ and $R^2$ which are vicinal are both hydrogen. In certain instances, $R^1$ and $R^1$ which are vicinal are both ethyl and $R^2$ and $R^2$ which are vicinal are both hydrogen. In certain instances, $R^1$ and $R^1$ which are vicinal are both methyl and $R^2$ and $R^2$ which are vicinal are both hydrogen.

In certain instances, in the chain of $-[C(R^1)(R^2)]_n-$ in Formula KC-(III), not every carbon is substituted. In certain instances, in the chain of $-[C(R^1)(R^2)]_n-$, there is a combination of different alkyl substituents, such as methyl or ethyl.

In certain instances, one of $R^1$ and $R^2$ is methyl, ethyl or other alkyl and $R^5$ is alkyl. In certain instances, $R^1$ and $R^1$ which are vicinal are both alkyl and $R^2$ and $R^2$ which are vicinal are both hydrogen and $R^5$ is alkyl. In certain instances, $R^1$ and $R^1$ which are vicinal are both ethyl and $R^2$ and $R^2$ which are vicinal are both hydrogen and $R^5$ is alkyl. In certain instances, $R^1$ and $R^1$ which are vicinal are both methyl and $R^2$ and $R^2$ which are vicinal are both hydrogen and $R^5$ is alkyl.

In certain instances, one of $R^1$ and $R^2$ is methyl, ethyl or other alkyl and $R^5$ is substituted alkyl. In certain instances, one of $R^1$ and $R^2$ is methyl, ethyl or other alkyl and $R^5$ is an alkyl group substituted with a carboxylic group such as a carboxylic acid, carboxylic ester or carboxylic amide. In certain instances, one of $R^1$ and $R^2$ is methyl, ethyl or other alkyl and $R^5$ is $-(CH_2)_q(C_6H_4)-COOH$, $-(CH_2)_q(C_6H_4)-COOCH_3$, or $-(CH_2)_q(C_6H_4)-COOCH_2CH_3$, where q is an integer from one to 10. In certain instances, one of $R^1$ and $R^2$ is methyl, ethyl or other alkyl and $R^5$ is an alkyl group substituted with carboxamide.

In formula HC-(I), $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group. In certain instances, $R^1$ and $R^2$ together with the carbon to which they are attached can form a cycloalkyl group. Thus, in certain instances, $R^1$ and $R^2$ on the same carbon form a spirocycle. In certain instances, $R^1$ and $R^2$ together with the carbon to which they are attached can form a substituted cycloalkyl group. In certain instances, two $R^1$ or $R^2$ groups on adjacent carbon atoms, together with the carbon atoms to which they are attached, can form a cycloalkyl group. In certain instances, two $R^1$ or $R^2$ groups on adjacent carbon atoms, together with the carbon atoms to which they are attached, can form a substituted cycloalkyl group.

In certain instances, $R^1$ and $R^2$ together with the carbon to which they are attached can form an aryl or substituted aryl group, or two $R^1$ or $R^2$ groups on adjacent carbon atoms, together with the carbon atoms to which they are attached, can form an aryl or substituted aryl group. In certain instances, two $R^1$ or $R^2$ groups on adjacent carbon atoms, together with the carbon atoms to which they are attached, form a phenyl ring. In certain instances, two $R^1$ or $R^2$ groups on adjacent carbon atoms, together with the carbon atoms to which they are attached, form a substituted phenyl ring. In certain instances, two $R^1$ or $R^2$ groups on adjacent carbon atoms, together with the carbon atoms to which they are attached, form a naphthyl ring.

In formula HC-(I), $R^4$ can be a residue of an L-amino acid selected from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine, or a residue of an N-acyl derivative of any of said amino acids; or a residue of a peptide composed of at least two L-amino acid residues selected independently from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine or a residue of an N-acyl derivative thereof. Such a peptide can be from 2 to about 100 amino acids in length. Examples of N-acyl derivatives include formyl, acetyl, benzoyl, malonyl, piperonyl, propionyl or succinyl derivatives.

In certain instances, $R^4$ is a residue of L-arginine or L-lysine, or a residue of an N-acyl derivative of L-arginine or L-lysine.

In certain instances, in formula HC-(I), when p is greater than one, then the $R^4$ adjacent to the nitrogen of $-N(R^3)(R^4)$ is a residue of L-arginine or L-lysine. In certain instances, when p is greater than one, the $R^4$ adjacent to the nitrogen of $-N(R^3)(R^4)$ is a residue of L-arginine or L-lysine and the first residue is joined to at least one additional L-amino acid residue selected independently from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine. The terminal residue of the peptide can be an N-acyl derivative of any of such amino acids. In certain instances $R^4$ is a dipeptide or an N-acyl derivative thereof. In certain instances R is a tripeptide or an N-acyl derivative thereof. In formula HC-(I), $R^4$ is

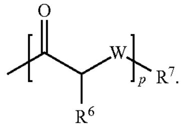

In formula HC-(I), each $R^6$ can be independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring.

In certain instances, in formula HC-(I), $R^6$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl. In certain instances, $R^6$ is selected from hydrogen, alkyl, substituted alkyl, arylalkyl, substituted arylalkyl, heteroarylalkyl, and substituted heteroarylalkyl. In certain instances, $R^6$ is hydrogen. In certain instances, $R^6$ is alkyl. In certain instances, $R^6$ is substituted alkyl. In certain instances, $R^6$ is arylalkyl or substituted arylalkyl. In certain instances, $R^6$ is heteroarylalkyl or substituted heteroarylalkyl.

In certain instances, $R^6$ is a side chain of an amino acid, such as alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine or valine. In certain instances, $R^6$ is a side chain of an L-amino acid, such as L-alanine, L-arginine, L-asparagine, L-aspartic acid, L-cysteine, L-glycine, L-glutamine, L-glutamic acid, L-histidine, L-isoleucine, L-leucine, L-lysine, L-methionine, L-phenylalanine, L-proline, L-serine, L-threonine, L-tryptophan, L-tyrosine or L-valine.

In certain instances, $R^6$ is $—CH_2CH_2CH_2NH(C{=}NH)NH_2$ or $—CH_2CH_2CH_2CH_2NH_2$.

In formula HC-(I), each W can be independently $—NR^8—$, —O— or —S—. In certain instances, W is $—NR^8—$. In certain instances, W is —O—. In certain instances, W is —S—.

In formula HC-(I), each $R^8$ can be independently hydrogen, alkyl, substituted alkyl, aryl or substituted aryl, or optionally, each $R^6$ and $R^8$ independently together with the atoms to which they are bonded form a cycloheteroalkyl or substituted cycloheteroalkyl ring.

In certain instances, in formula HC-(I), $R^8$ is hydrogen or alkyl. In certain instances, $R^8$ is hydrogen. In certain instances, $R^8$ is alkyl. In certain instances, $R^8$ is aryl. In certain instances, $R^6$ and $R^8$ independently together with the atoms to which they are bonded form a cycloheteroalkyl or substituted cycloheteroalkyl ring.

In formula HC-(I), p can be an integer from one to 100 and each $R^6$ can be selected independently from a side chain of any amino acid. In certain instances, p is an integer from one to 50. In certain instances, p is an integer from one to 90, 80, 70, 60, 50, 40, 30, 20, or 10. In certain instances, p is about 100. In certain instances, p is about 75. In certain instances, p is about 50. In certain instances, p is about 25. In certain instances, p is about 20. In certain instances, p is about 15. In certain instances, p is about 10. In certain instances, p is about 9. In certain instances, p is about 8. In certain instances, p is about 7. In certain instances, p is about 6. In certain instances, p is about 5. In certain instances, p is about 4. In certain instances, p is about 3. In certain instances, p is about 2. In certain instances, p is about one.

In certain instances, the $R^6$ of $R^4$ adjacent to the nitrogen of $—N(R^3)(R^4)$ is $—CH_2CH_2CH_2NH(C{=}NH)NH_2$ or $—CH_2CH_2CH_2CH_2NH_2$, and any additional $R^6$ can be a side chain of any amino acid independently selected from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine or valine.

In formula HC-(I), $R^7$ can be selected from hydrogen, alkyl, substituted alkyl, acyl, substituted acyl, alkoxycarbonyl, substituted alkoxycarbonyl, aryl, substituted aryl, arylalkyl, and substituted arylalkyl.

In certain instances, $R^7$ is hydrogen, alkyl, acyl, or substituted acyl. In certain instances, $R^7$ is hydrogen. In certain instances, $R^7$ is alkyl. In certain instances, $R^7$ is acyl or substituted acyl. In certain instances, $R^7$ is acyl. In certain instances, $R^7$ is substituted acyl. In certain instances, $R^7$ can be formyl, acetyl, benzoyl, malonyl, piperonyl, propionyl or succinyl.

Formula HC-(II)

Compounds of the present disclosure include compounds of formula HC-(II) shown below. Compositions of the present disclosure also include compounds of formula HC-(II) shown below. Pharmaceutical compositions and methods of the present disclosure also contemplate compounds of formula HC-(II).

The present embodiments provide a compound of formula HC-(II):

HC-(II)

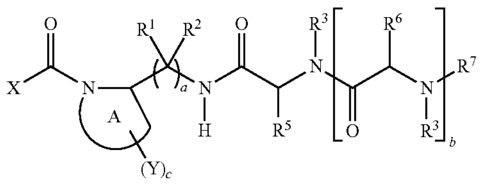

wherein

X is selected from a residue of a ketone-containing opioid, wherein the hydrogen atom of the corresponding hydroxyl group of the enolic tautomer of the ketone is replaced by a covalent bond to $—C(O)—N[(A\ ring)\text{-}Y_c]—(CR^1R^2)_a—NH—C(O)—CH(R^5)—N(R^3)—[C(O)—CH(R^6)—N(R^3)]_b—R^7$; a residue of a phenolic opioid, wherein the hydrogen atom of the phenolic hydroxyl group is replaced by a covalent bond to $—C(O)—N[(A\ ring)\text{-}Y_c]—(CR^1R^2)_a—NH—C(O)—CH(R^5)—N(R^3)—[C(O)—CH(R^6)—N(R^3)]_b—R^7$; and a residue of an amide-containing opioid, wherein $—C(O)—N[(A\ ring)\text{-}Y_c]—(CR^1R^2)_a—NH—C(O)—CH(R^5)—N(R^3)—[C(O)—CH(R^6)—N(R^3)]_b—R^7$ is connected to the amide-containing opioid through the oxygen of the amide group, wherein the amide group is converted to an amide enol or an imine tautomer;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

each $R^1$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

each $R^2$ is independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano; or $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group; a is an integer from one to 8;

provided that when a is one, the A ring is a heterocyclic 6 to 12-membered ring; and when the A ring is a heterocyclic 5-membered ring, then a is an integer from 2 to 8;

each $R^3$ is independently hydrogen, alkyl, substituted alkyl, aryl or substituted aryl;

$R^5$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl;

b is a number from zero to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

In formulae HC-(I) and HC-(II), X can be selected from a residue of a ketone-containing opioid, wherein the hydrogen atom of the corresponding hydroxyl group of the enolic tautomer of the ketone is replaced by a covalent bond to —C(O)—N[(A ring)-$Y_c$]—($CR^1R^2$)$_a$—NH—C(O)—CH($R^5$)—N($R^3$)—[C(O)—CH($R^6$)—N($R^3$)]$_b$—$R^7$; a residue of a phenolic opioid, wherein the hydrogen atom of the phenolic hydroxyl group is replaced by a covalent bond to —C(O)—N[(A ring)-Y]—($CR^1R^2$)$_a$—NH—C(O)—CH($R^5$)—N($R^3$)—[C(O)—CH($R^6$)—N($R^3$)]$_b$—$R^7$; and a residue of an amide-containing opioid, wherein —C(O)—N[(A ring)-$Y_c$]—($CR^1R^2$)$_a$—NH—C(O)—CH($R^5$)—N($R^3$)—[C(O)—CH($R^6$)—N($R^3$)]$_b$—$R^7$ is connected to the amide-containing opioid through the oxygen of the amide group, wherein the amide group is converted to an amide enol or an imine tautomer.

In certain instances, X is a ketone-containing opioid, wherein the hydrogen atom of the corresponding hydroxyl group of the enolic tautomer of the ketone is replaced by a covalent bond to —C(O)—N[(A ring)-$Y_c$]—($CR^1R^2$)$_a$—NH—C(O)—CH($R^5$)—N($R^3$)—[C(O)—CH($R^6$)—N($R^3$)]$_b$—$R^7$.

In certain instances, X is a ketone-containing opioid, wherein the opioid is selected from acetylmorphone, hydrocodone, hydromorphone, ketobemidone, methadone, naloxone, naltrexone, N-methylnaloxone, N-methylnaltrexone, oxycodone, oxymorphone, and pentamorphone.

In certain instances, X is a residue of a phenolic opioid, wherein the hydrogen atom of the phenolic hydroxyl group is replaced by a covalent bond to —C(O)—N[(A ring)-$Y_c$]—($CR^1R^2$)$_a$—NH—C(O)—CH($R^5$)—N($R^3$)—[C(O)—CH($R^6$)—N($R^3$)]$_b$—$R^7$.

In certain instances, X is a phenolic opioid, wherein the opioid is selected from buprenorphine, dihydroetorphine, diprenorphine, etorphine, hydromorphone, levorphanol, morphine, nalbuphine, nalmefene, nalorphine, naloxone, naltrexone, N-methyldiprenorphine, N-methylnaloxone, N-methylnaltrexone, oripavine, oxymorphone, butorphanol, dezocine, ketobemidone, meptazinol, o-desmethyltramadol, pentazocine, phenazocine, and tapentadol.

In certain instances, X is a residue of an amide-containing opioid, wherein —C(O)—N[(A ring)-$Y_c$]—($CR^1R^2$)$_a$—NH—C(O)—CH($R^5$)—N($R^3$)—[C(O)—CH($R^6$)—N($R^3$)]$_b$—$R^7$ is connected to the amide-containing opioid through the oxygen of the amide group, wherein the amide group is converted to an amide enol or an imine tautomer.

In certain instances, X is an amide-containing opioid, wherein the opioid is selected from alfentanil, carfentanil, fentanyl, lofentanil, loperamide, olmefentanyl, remifentanil, and sufentanil.

In some embodiments, the heterocyclic linked active agent prodrugs include those described in International Patent Publication No. WO 2012/122422 and U.S. Pat. No. 8,685,916, the disclosures of which are herein incorporated by reference.

Amino Acids Found in Prodrugs

"Amino acid" means a building block of a polypeptide. As used herein, "amino acid" includes the 20 common naturally occurring L-amino acids and all amino acids variants. In certain embodiments, an amino acid is a cleavable substrate for a gastrointestinal enzyme.

"Naturally occurring amino acids" means the 20 common naturally occurring L-amino acids, that is, alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine.

"Amino acid variants" means an amino acid other than any of the 20 common naturally occurring L-amino acids that is hydrolysable by a protease in a manner similar to the ability of a protease to hydrolyze a naturally occurring L-amino acid. Amino acid variants, thus, include amino acids or analogs of amino acids other than the 20 naturally-occurring amino acids. Amino acid variants include synthetic amino acids. Amino acid variants also include amino acid derivatives. A derivative refers to a substance that has been altered from another substance by modification, partial substitution, homologation, truncation, or a change in oxidation state while retaining the ability to be cleaved by a GI enzyme.

Certain examples of amino acid variants include, but are not limited to: 2-aminoindane-2-carboxylic acid, 2-aminoisobutyric acid, 4-amino-phenylalanine, 5-hydroxylysine, biphenylalanine, citrulline, cyclohexylalanine, cyclohexylglycine, diethylglycine, dipropylglycine, homoarginine, homocitrulline, homophenylalanine, homoproline, homoserine, homotyrosine, hydroxyproline, lanthionine, naphthylalanine, norleucine, ornithine, phenylalanine(4-fluoro), phenylalanine(4-nitro), phenylglycine, pipecolic acid, tert-butylalanine, tert-butylglycine, tert-leucine, tetrahydroisoquinoline-3-carboxylic acid, α-aminobutyric acid, γ-amino butyric acid, 2,3-diaminoproprionic acid, phenylalanine(2,3,4,5,6 pentafluoro), aminohexanoic acid and derivatives thereof.

Certain examples of amino acid variants include, but are not limited to, N-methyl amino acids. For example, N-methyl-alanine, N-methyl aspartic acid, N-methyl-glutamic acid, N-methyl-glycine (sarcosine) are N-methyl amino acids.

Certain examples of amino acid variants include, but are not limited to: dehydroalanine, ethionine, hypusine, lanthionine, pyrrolysine, a-aminoisobutyric acid, selenomethionine and derivatives thereof.

Certain examples of amino acid variants include, but are not limited to: (3,2-amino benzoic acid, 2-amino methyl benzoic acid, 2-amino-3-guanidinopropionic acid, 2-amino-3-methoxy benzoic acid, 2-amino-3-ureidopropionic acid, 3-amino benzoic acid, 4-amino benzoic acid, 4-amino methyl benzoic acid, 4-nitroanthranillic acid, 5-acetamido-2-aminobenzoic acid, butanoic acid (HMB), glutathione, homocysteine, statine, taurine, P-alanine, 2-hydroxy-4-(methylthio), (3,4)-diamino benzoic acid, (3,5)-diamino benzoic acid and derivatives thereof.

Certain examples of amino acid variants include, but are not limited to: (2 amino ethyl) cysteine, 2-amino-3-ethyoxybutanoic acid, buthionine, cystathion, cysteic acid, ethionine, ethoxytheorine, methylserine, N-ε-ε-dimethyl-lysine, N-o-nitro-arginine, saccharopine, isoserine derivatives thereof, and combinations thereof.

Certain examples of amino acid variants include, but are not limited to: l-carnitine, selenocysteine, l-sarcosine, l-lysinol, benzoic acid, citric acid, choline, EDTA or succinic acid and derivatives thereof.

Certain examples of amino acid variants are amino alcohols. Examples of amino alcohols include, but are not limited to: alaninol, indano, norephedrine, asparaginol, aspartimol, glutamol, leucinol, methioninol, phenylalaninol, prolinol, tryptophanol, valinol, isoleucinol, argininol, serinol, tyrosinol, threoninol, cysteinol, lysinol, histidinol and derivatives thereof.

In some embodiments, the active agent prodrugs are formulated in any convenient form suitable for oral (including buccal and sublingual) administration for example as a tablet, capsule, powder, suspension, dispersion or emulsion. Pharmaceutical compositions of the active agent prodrug may include one or more pharmaceutically acceptable carriers. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7th ed., Lippincott, Williams, & Wilkins; and Handbook of Pharmaceutical Excipients (2000) A. H. Kibbe et al., eds., 3rd ed. Amer. Pharmaceutical Assoc. For example, the one or more excipients may include sucrose, starch, mannitol, sorbitol, lactose, glucose, cellulose, talc, calcium phosphate or calcium carbonate, a binder (e.g., cellulose, methylcellulose, hydroxymethylcellulose, polypropylpyrrolidone, polyvinylpyrrolidone, gelatin, gum arabic, poly(ethylene glycol), sucrose or starch), a disintegrator (e.g., starch, carboxymethylcellulose, hydroxypropyl starch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinylpyrrolidone or aluminum stearate), a dispersing agent (e.g., hydroxypropylmethylcellulose), a diluent (e.g., water), and base wax (e.g., cocoa butter, white petrolatum or polyethylene glycol).

The amount of active agent prodrug in a unit composition, for example, a capsule or tablet of the active agent prodrug or pharmaceutically acceptable salt thereof, may include from 1 mg and 400 mg of active agent prodrug or pharmaceutically acceptable salt thereof, for example, between: 1 and 10 mg, 10 and 20 mg, 20 and 30 mg, 30 and 40 mg, 40 and 50 mg, 50 and 60 mg, 60 and 70 mg, 70 and 80 mg, 80 and 90 mg, 90 and 100 mg, 100 and 110 mg, 110 and 120 mg, 120 and 130 mg, 130 and 140 mg, 140 and 150 mg, 150 and 160 mg, 160 and 170 mg, 170 and 180 mg, 180 and 190 mg, 190 and 200 mg, 200 and 210 mg, 210 and 220 mg, 220 and 230 mg, 230 and 240 mg, 240 and 250 mg, 250 and 260 mg, 260 and 270 mg, 270 and 280 mg, 280 and 290 mg, 290 and 300 mg, 300 and 310 mg, 310 and 320 mg, 320 and 330 mg, 330 and 340 mg, 340 and 350 mg, 350 and 360 mg, 360 and 370 mg, 370 and 380 mg, 380 and 390 mg and between 390 and 400 mg.

In some embodiments, compositions of interest include an aqueous buffer. Suitable aqueous buffers include, but are not limited to, acetate, succinate, citrate, and phosphate buffers varying in strengths from about 5 mM to about 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. In some instances, compositions of interest further include a preservative. Suitable preservatives include, but are not limited to, a benzyl alcohol, phenol, chlorobutanol, benzalkonium chloride, and the like. In many cases, the composition is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures.

In some embodiments, pharmaceutical compositions of the active agent prodrug include other additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Orally Administered Controlled-Release Compositions of Nafamostat or Pharmaceutically Acceptable Salt Thereof As summarized above, aspects of the present disclosure include oral compositions of nafamostat or a pharmaceutically acceptable salt thereof that provides for controlled release of nafamostat or pharmaceutically acceptable salt thereof to a subject for an extended period of time. As described herein, the compound nafamostat refers to 6-carbamimidoylnaphthalen-2-yl 4-(diaminomethyleneamino) benzoate:

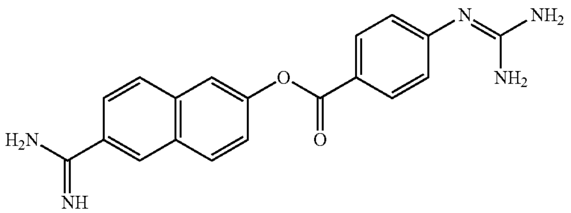

Nafamostat (6-carbamimidoylnaphthalen-2-yl 4-(diaminomethyleneamino)benzoate)

In some embodiments, compositions include nafamostat free base. In other embodiments, compositions include a pharmaceutically acceptable salt of nafamostat. In embodiments, "salts" of nafamostat may include, but are not limited to: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the compound is replaced by a metal ion, e.g., an alkali metal ion, an alkaline earth ion, or an aluminum ion; or coordinates with an organic base such as ethanolamine, diethanolamine, triethanolamine, N-methylglucamine and the like. In certain embodiments, the salt of nafamostat is nafamostat mesylate.

In embodiments, oral compositions of nafamostat or a pharmaceutically acceptable salt thereof provide post administration-activated, controlled release of nafamostat or pharmaceutically acceptable salt thereof to a subject for an extended period of time. In some embodiments, the controlled release composition provides for the sustained release of one or more doses of nafamostat or pharmaceutically acceptable salt thereof to the subject. In some instances, the sustained release of nafamostat is a zero-order sustained release. In other instances, the sustained release of nafamostat is a first-order sustained release. For example, controlled release nafamostat compositions may provide for sustained release of 0.000001 μg/min or more of the nafamostat, such as 0.000005 μg/min or more, such as 0.00001 μg/min or more, such as 0.0005 μg/min or more, such as 0.001 μg/min or more, such as 0.005 μg/min or more, such as 0.01 μg/min or more, such as 0.05 μg/min or more, such as 0.1 μg/min or more, such as 0.5 μg/min or more, such as 1 μg/min or more, such as 5 μg/min or more, such as 10 μg/min or more, such as 100 μg/min or more and including sustained release of 250 μg/min or more of nafamostat or pharmaceutically acceptable salt thereof.

In some embodiments, controlled release compositions of nafamostat provide for delayed immediate release of nafamostat or pharmaceutically acceptable salt thereof. The term "delayed immediate release" is used herein to refer to the timing that nafamostat or pharmaceutically acceptable salt thereof is released after administration, where an amount of the nafamostat is released from the composition at a predetermined period of time after administration to the subject. In some instances, delayed immediate release compositions of nafamostat are formulated to release 50% or more of nafamostat or pharmaceutically acceptable salt thereof at the predetermined period of time, such as formulated to release 60% or more, such as 70% or more, such as 80% or more, such as 90% or more, such as 95% or more, such as 97% or more, such as 99% or more and including being formulated to release all of the nafamostat in the composition (100%) at a predetermined period of time after administration of the composition to the subject. The period of time of the delayed release may vary, where in some instances, compositions of interest are formulated to release the nafamostat or pharmaceutically acceptable salt thereof 5 minutes or more after orally administering the composition to the subject, such as 10 minutes or more, such as 15 minutes or more, such as 20 minutes or more, such as 30 minutes or more, such as 45 minutes or more, such as 60 minutes or more, such as 2 hours or more, such as 3 hours or more, such as 4 hours or more, such as 6 hours or more, such as 8 hours or more, such as 10 hours or more, such as 12 hours or more, such as 18 hours or more and including 24 hours or more after orally administering the composition to the subject.

In some embodiments, the controlled release compositions of nafamostat provide for a release profile where 50% or more of the nafamostat or pharmaceutically acceptable salt thereof is released within 6 hours after administration, such as 55% or more, such as 60% or more, such as 65% or more, such as 70% or more, such as 75% or more, such as 80% or more, such as 85% or more, such as 90% or more, such as 95% or more, such as 97% or more such as 99% or more and including being formulated to release all of the nafamostat in the composition (100%) within 6 hours after administration of the composition to the subject.

In certain embodiments, the controlled release compositions provide for release of nafamostat or pharmaceutically acceptable salt thereof at a first rate for a first predetermined period of time followed by releasing the nafamostat or pharmaceutically acceptable salt thereof at a second rate for a second predetermined period of time. In some instances, the controlled release composition is configured to release nafamostat at rate of 0.000001 μg/min or more for a first predetermined period of time, such as 0.000005 μg/min or more, such as 0.00001 μg/min or more, such as 0.0005 μg/min or more, such as 0.001 μg/min or more, such as 0.005 μg/min or more, such as 0.01 μg/min or more, such as 0.05 μg/min or more, such as 0.1 μg/min or more, such as 0.5 μg/min or more, such as 1 μg/min or more, such as 5 μg/min or more, such as 10 μg/min or more, such as 100 μg/min or more and including releasing 250 μg/min or more for a first predetermined period of time. In some instances, the first predetermined period of time is 5 minutes or more, such as 10 minutes or more, such as 15 minutes or more, such as 20 minutes or more, such as 30 minutes or more, such as 45 minutes or more, such as 60 minutes or more, such as 2 hours or more, such as 3 hours or more, such as 4 hours or more, such as 6 hours or more, such as 8 hours or more, such as 10 hours or more, such as 12 hours or more, such as 18 hours or more and including 24 hours or more. In some instances, the first period of time is followed by controlled release of nafamostat at rate of 0.000001 μg/min or more for a second predetermined period of time, such as 0.000005 μg/min or more, such as 0.00001 μg/min or more, such as 0.0005 μg/min or more, such as 0.001 μg/min or more, such as 0.005 μg/min or more, such as 0.01 μg/min or more, such as 0.05 μg/min or more, such as 0.1 μg/min or more, such as 0.5 μg/min or more, such as 1 μg/min or more, such as 5 μg/min or more, such as 10 μg/min or more, such as 100 μg/min or more and including 250 μg/min or more for a second predetermined period of time. In some instances, the second predetermined period of time is 30 minutes or more, such as 60 minutes or more, such as 2 hours or more, such as 3 hours or more, such as 4 hours or more, such as 6 hours or more, such as 8 hours or more, such as 12 hours or more, such as 24 hours or more, such as 48 hours or more and including 72 hours or more.

In certain embodiments, oral compositions of nafamostat or a pharmaceutically acceptable salt thereof are formulated as a plurality of controlled release beads where each bead includes a core, an active agent layer having nafamostat or a pharmaceutically acceptable salt thereof and a controlled release layer having one or more polymers formulated in an amount sufficient to provide for controlled release of the nafamostat or pharmaceutically acceptable salt thereof. In some embodiments, the size of the beads ranges from 0.001 mm to 5 mm in diameter, such as from 0.005 mm to 4.5 mm, such as from 0.01 mm to 4 mm, such as from 0.05 mm to 3.5 mm, such as from 0.1 mm to 3 mm, such as from 0.5 mm to 2.5 mm, such as from 1 mm to 3 mm and including from 0.2 mm and 3 mm in diameter.

In some instances, the core is formed from an inert substance. Such substances include a cellulose polymer, silicon dioxide, a sugar, starch, or a combination thereof. The sugar can be glucose, sucrose, lactose, mannitol, xylitol, sorbitol, or a combination thereof. In some embodiments, the core may be formed from microcrystalline cellulose, Cellets® cores, such as Cellets® 100, Cellets® 200, Cellets® 350, Cellets® 500, Cellets® 700, or Cellets® 1000 (Glatt Air Techniques Inc., Ramsey N.J.). In other embodiments, the core is prepared de novo, for example by preparing a polymer mixture, extruding the mixture, and spheronizing the extruded mixture to form spherical or semi-spherical beads. In some embodiments, the beads are swellable such that their exposure to aqueous media causes them to swell and release the active ingredient rapidly and efficiently. In some embodiments, the core comprises between about 10% to about 50% of the total weight of the finally-formulated bead. In some embodiments, the core comprises between about 15% to about 40% of the total weight of the finally-formulated bead. In some embodiments, the core comprises between about 20% to about 30% of the total weight of the finally-formulated bead. In some embodiments, the core comprises about 20% of the total weight of the finally-formulated bead. In some embodiments, the core comprises about 25% of the total weight of the finally-formulated bead. In certain embodiments, the core is a microcrystalline cellulose (MCC) bead, such as a Cellets microcrystalline cellulose bead.

In some embodiments, an active agent layer having nafamostat or a pharmaceutically acceptable salt thereof (e.g., nafamostat or nafamostat mesylate) is formed on the core. In some embodiments, the active agent layer comprises between about 1% to about 50% of the total weight of the bead. In some embodiments, the active agent layer comprises between about 2% to about 40% of the total weight of the bead. In some embodiments, the active agent layer comprises between about 5% to about 30% of the total weight of the bead. In some embodiments, the active agent layer comprises between about 7% to about 25% of the total weight of the bead. In some embodiments, the active agent layer comprises between about 8% to about 15% of the total weight of the bead. In some embodiments, the active agent layer comprises about 8% of the total weight of the bead. In some embodiments, the active agent layer comprises about 10% of the total weight of the bead. In some embodiments, the active agent layer comprises about 12% of the total weight of the bead. In some embodiments, the active agent layer comprises about 15% of the total weight of the bead.

In some embodiments, the application of the active agent layer causes a weight gain of between about 1% to about 50% of the weight prior to the application of the active agent layer. Thus, for example, if the weight of the core prior to the application of the active agent layer is X, then after the application of the active agent layer, the weight of each bead is 1.01X, if the weight gain is 1%, or the weight of each bead is 1.5X, if the weight gain is 50%. In some embodiments, the weight gain is between about 5% to about 45%. In some embodiments, the weight gain is between about 5% to about 40%. In some embodiments, the weight gain is between about 5% to about 35%. In some embodiments, the weight gain is between about 5% to about 30%. In some embodiments, the weight gain is between about 10% to about 25%.

Nafamostat or a pharmaceutically acceptable salt thereof may be present in the active agent layer of each bead in an amount of 0.000001 mg or more, such as 0.00001 mg or more, such as 0.0001 mg or more, such as 0.001 mg or more, such as 0.01 mg or more, such as 0.1 mg or more, such as 0.5 mg or more, such as 1 mg or more and including 2 mg or more. In some embodiments, the drug loading of nafamostat or pharmaceutically acceptable salt thereof of each bead is from 1% w/w to 25% w/w, such as from 2% w/w to 24% w/w, such as from 3% w/w to 23% w/w, such as from 4% w/w to 22% w/w, such as from 5% w/w to 21% w/w, such as from 6% w/w to 20% w/w, such as from 7% w/w to 19% w/w, such as from 8% w/w to 18% w/w, such as from 9% w/w to 15% w/w and including from 11% w/w to 13% w/w. As described in greater detail below, oral compositions of nafamostat according to embodiments of the present disclosure may include 10 mg or more of nafamostat or a pharmaceutically acceptable salt thereof, such as 15 mg or more, such as 20 mg or more, such as 25 mg or more, such as 30 mg or more, such as 35 mg or more, such as 40 mg or more, such as 45 mg or more, such as 50 mg or more, such as 60 mg or more, such as 70 mg or more, such as 80 mg or more, such as 90 mg or more, such as 100 mg or more, such as 150 mg or more and including 200 mg or more.

In addition to nafamostat or a pharmaceutically acceptable salt thereof, the active agent layer can further contain a binder. The binder can be a pharmaceutically acceptable polymer, such as a hydroxyalkyl cellulose, maltodextrin, cellulose acetate phthalate, sucrose, modified starch, a salt of alginic acid, soluble gums, carrageenan, an alkyl cellulose, corn starch, polyethylene glycol, polyethylene oxide, hydroxypropylmethylcellulose phthalate, insoluble gums, polymethacrylate, polyvinylpyrrolidone (PVP) or polyvinylpolypyrrolidone (PVPP), polyvinyl alcohol, shellac, and polyvinyl acetate phthalate or any combination thereof. A hydroxyalkyl cellulose can be hydroxypropyl cellulose, hydroxyethyl cellulose, hydroxypropylmethyl cellulose, or any combination thereof. An alkyl cellulose can be cellulose, ethyl cellulose, ethylmethyl cellulose, or any combination thereof. In certain embodiments, the binder comprises hydroxypropyl methylcellulose.

In some embodiments, the active agent layer containing nafamostat or a pharmaceutically acceptable salt thereof may further include a de-tackifier or glidant, such as talc, an amorphous silica such as syloid (e.g., syloid 244FP), a monoglyceride, a diglyceride, glyceryl monostearate, calcium stearate, and magnesium stearate.

In other embodiments, the active agent layer containing the nafamostat or a pharmaceutically acceptable salt thereof includes a lipid excipient, such as glyceryl behenate, glycerol esters of fatty acids, glyceryl dibehenate, behenoyl macrogoglycerides, glyceryl distearate, glycerol distearate, glyceryl palmitostearate, lauroyl macrogoglycerides, stearoyl macrogoglycerides, abitec products, glyceryl monooleate, medium chain mono- & diglycerides, glyceryl monocaprylate, glyceryl tricaprylate/caprate/stearate, hydrogenated vegetable oil, hydrogenated cottonseed oil, hydrogenated soybean oil, hydrogenated soybean oil and castor wax, polyoxyethylene 8 caprylic/capric glycerides, polyoxyethylene 6 caprylic/capric glycerides, polyoxyethylene 32 lauric glycerides, polyoxyethylene 6 prop. Glycol esters, polyoxyethylene 7 coconut glycerides, polyoxyethylene 30 coconut glycerides, polyoxyethylene 80 coconut glycerides, polyoxypropylene 15 stearyl ether, polyoxyethylene 26 glyceryl ether, polyoxyethylene 35 soybean glycerides, polyoxyethylene 20 sorbitol, polyoxypropylene myristyl ether, polyoxypropylene 10 cetostearyl ether, palm kernelamide diethanolamide, triglycerol mono-oleate, sasol products, hydrogenated coco-glycerides, cetyl palmitate, trimyristin, tripalmitin, tristearin, hydrogenated palm oil, glyceryl monostearate, glyceryl stearate, cetearyl alcohol, cetyl alcohol, capric triglyceride, acetylated glycerides, glyceryl cocoate, and polyethylene glycol or combinations thereof.

In certain embodiments, the active agent layer containing nafamostat or a pharmaceutically acceptable salt thereof includes nafamostat or a pharmaceutically acceptable salt thereof and hydroxypropyl methylcellulose.

In some embodiments, the controlled release beads include a controlled release layer having one or more polymers formulated to provide for controlled release of the nafamostat or pharmaceutically acceptable salt thereof. The polymers are pharmaceutically acceptable and suitable for providing controlled release of nafamostat over an extended period of time as described above. In some instances, polymers of the controlled release layer include but are not limited to cellulose ethers such as Ethocel™, acrylate polymers, methacrylate polymers, neutral (meth)acrylate-based polymers such as Eudragit™ NE 30D, ionic (meth)acrylate-based polymers such as Eudragit™ RS or RL, polyvinyl acetate, or combinations thereof. In certain embodiments, polymers of the controlled release layer are stabilized with polyvinylpyrrolidone (PVP), such as Kollicoat™ SR.

In some embodiments, the controlled release layer includes an acrylate copolymer. Acrylate copolymers can include copolymers of various monomers, such as "soft" monomers, "hard" monomers or "functional" monomers. The acrylate copolymers can be composed of a copolymer including a bipolymer (i.e., made with two monomers), a terpolymer (i.e., made with three monomers), or a tetrapolymer (i.e., made with four monomers), or copolymers having greater numbers of monomers. The acrylate copolymers may be crosslinked or non-crosslinked. The polymers can be cross-linked by known methods to provide the desired polymers. The monomers from of the acrylate copolymers may include two or more components selected from the group including acrylic acids, alkyl acrylates, methacrylates, copolymerizable secondary monomers or monomers with functional groups. Monomers ("soft" and "hard" monomers) may be methoxyethyl acrylate, ethyl acrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, acrylonitrile, methoxyethyl acrylate, methoxyethyl methacrylate, and the like. In certain embodiments, the controlled release layer includes a methacrylate acrylate copolymer or a mixture of two or more methacrylate acrylate copolymers. In some instances, methacrylate acrylate copolymers of interest are substantially the same as Eudragit™ acrylate copolymers, as described below. In certain instances, the controlled release layer includes an acrylate copolymer that is substantially the same as Eudragit RS. In certain instances, the controlled release layer includes an acrylate copolymer that is substantially the same as Eudragit RL. In certain instances, the controlled release layer includes a first acrylate copolymer that is substantially the same as Eudragit RS and a second acrylate copolymer that is substantially the same as Eudragit RL.

In some embodiments, the controlled release layer includes two different polymers (e.g., two different acrylate copolymers). In some instances, the first polymer is present in the controlled release layer in an amount that ranges from 0.01% to 99.99% by weight, such as from 0.1% to 99.9% by weight, such as from 0.5% to 99.5% by weight, such as from 1% to 99% by weight, such as from 2% to 98% by weight, such as from 3% to 97% by weight, such as from 4% to 96% by weight, such as from 5% to 95% by weight, such as from 6% to 94% by weight, such as from 7% to 93% by weight, such as from 8% to 92% by weight, such as from 9% to 91% by weight, such as from 10% to 90% by weight, such as from 15% to 85% by weight, such as from 20% to 80% by weight, such as from 25% to 75% by weight, such as from 30% to 70% by weight, such as from 35% to 65% by weight, such as from 40% to 60% by weight and including from 45% to 55% by weight. In some instances, the second polymer is present in the controlled release layer in an amount that ranges from 0.01% to 99.99% by weight, such as from 0.1% to 99.9% by weight, such as from 0.5% to 99.5% by weight, such as from 1% to 99% by weight, such as from 2% to 98% by weight, such as from 3% to 97% by weight, such as from 4% to 96% by weight, such as from 5% to 95% by weight, such as from 6% to 94% by weight, such as from 7% to 93% by weight, such as from 8% to 92% by weight, such as from 9% to 91% by weight, such as from 10% to 90% by weight, such as from 15% to 85% by weight, such as from 20% to 80% by weight, such as from 25% to 75% by weight, such as from 30% to 70% by weight, such as from 35% to 65% by weight, such as from 40% to 60% by weight and including from 45% to 55% by weight.

The ratio by weight of the first polymer (e.g., first acrylate copolymer) to the second polymer (e.g., second acrylate copolymer) in the controlled release layer to may vary, such as from 1:99 to 99:1, such as from 5:95 to 95:5, such as from 10:90 to 90:10, such as from 20:80 to 80:20, such as from 30:70 to 70:30, such as from 40:60 to 60:40 and including where the ratio by weight of the first polymer to the second polymer in the controlled release layer is 50:50. In certain embodiments, the ratio by weight of the first polymer to the second polymer in the controlled release layer may be 80:20, such as the first polymer to the second polymer of 87:13, such as a ratio of the first polymer to the second polymer of 90:10, such as a ratio of the first polymer to the second polymer of 92:8 and including a ratio of the first polymer to the second polymer of 95:5

In some instances, the controlled release layer includes a copolymer of ethylacrylate, methyl methacrylate and chlorotrimethyl-ammonioethyl methacrylate. In certain instances, the polymer is poly(ethylacrylate, methyl-methacrylate and chlorotrimethyl-ammonioethyl methacrylate) containing quaternary ammonium groups. For example, the acrylate copolymer may be a combination of: 1) poly (ethylacrylate, methyl-methacrylate and chlorotrimethyl-ammonioethyl methacrylate) containing about 50 mEq of quaternary ammonium groups per 100 g of polymer (hereinafter, "acrylate copolymer A"; where in some instances, acrylate copolymer A is substantially the same as Eudragit™ RL) and 2) poly(ethylacrylate, methyl-methacrylate and chlorotrimethyl-ammonioethyl methacrylate) containing about 25 mEq of quaternary ammonium groups per 100 g of polymer (hereinafter, "acrylate copolymer B"; where in some instances, acrylate copolymer B is substantially the same as Eudragit™ RS). In some instances, the acrylate copolymer A is present in the polymer of the controlled release layer in an amount that ranges from 0.01% to 99.99% by weight, such as from 0.1% to 99.9% by weight, such as from 0.5% to 99.5% by weight, such as from 1% to 99% by weight, such as from 2% to 98% by weight, such as from 3% to 97% by weight, such as from 4% to 96% by weight, such as from 5% to 95% by weight, such as from 6% to 94% by weight, such as from 7% to 93% by weight, such as from 8% to 92% by weight, such as from 9% to 91% by weight, such as from 10% to 90% by weight, such as from 15% to 85% by weight, such as from 20% to 80% by weight, such as from 25% to 75% by weight, such as from 30% to 70% by weight, such as from 35% to 65% by weight, such as from 40% to 60% by weight and including from 45% to 55% by weight. In some instances, acrylate copolymer B is present in the polymer of the controlled release layer in an amount that ranges from 0.01% to 99.99% by weight, such as from 0.1% to 99.9% by weight, such as from 0.5% to 99.5% by weight, such as from 1% to 99% by weight, such as from 2% to 98% by weight, such as from 3% to 97% by weight, such as from 4% to 96% by weight, such as from 5% to 95% by weight, such as from 6% to 94% by weight, such as from 7% to 93% by weight, such as from 8% to 92% by weight, such as from 9% to 91% by weight, such as from 10% to 90% by weight, such as from 15% to 85% by weight, such as from 20% to 80% by weight, such as from 25% to 75% by weight, such as from 30% to 70% by weight, such as from 35% to 65% by weight, such as from 40% to 60% by weight and including from 45% to 55% by weight.

The ratio by weight of acrylate copolymer A to acrylate copolymer B in the controlled release layer to may vary, such as from 1:99 to 99:1, such as from 5:95 to 95:5, such as from 10:90 to 90:10, such as from 20:80 to 80:20, such as from 30:70 to 70:30, such as from 40:60 to 60:40 and including where the ratio by weight of the acrylate copolymer A to acrylate copolymer B in the controlled release layer is 50:50. In certain embodiments, the controlled release layer includes a ratio of acrylate copolymer B to acrylate copolymer A of 80:20, such as a ratio of acrylate copolymer B to acrylate copolymer A of 87:13, such as a ratio of acrylate copolymer B to acrylate copolymer A of 90:10, such as a ratio of acrylate copolymer B to acrylate copolymer A of 92:8 and including a ratio of acrylate copolymer B to acrylate copolymer A of 95:5.

In certain cases, the polymer of the controlled release layer comprises 20% by weight acrylate copolymer B and 80% by weight acrylate copolymer A.

In certain cases, the polymer of the controlled release layer comprises 50% by weight acrylate copolymer B and 50% by weight acrylate copolymer A.

In certain cases, the polymer of the controlled release layer comprises 80% by weight acrylate copolymer B and 20% by weight acrylate copolymer A.

In certain cases, the polymer of the controlled release layer comprises 100% by weight acrylate copolymer B.

In certain cases, the polymer of the controlled release layer comprises 100% by weight acrylate copolymer A.

In certain cases, the polymer of the controlled release layer comprises 95% by weight acrylate copolymer B and 5% by weight acrylate copolymer A.

In certain cases, the polymer of the controlled release layer comprises 93% by weight acrylate copolymer B and 7% by weight acrylate copolymer A.

In certain cases, the polymer of the controlled release layer comprises 92% by weight acrylate copolymer B and 8% by weight acrylate copolymer A.

In certain cases, the polymer of the controlled release layer comprises 90% by weight acrylate copolymer B and 10% by weight acrylate copolymer A.

In certain cases, the polymer of the controlled release layer comprises 87% by weight acrylate copolymer B and 13% by weight acrylate copolymer A.

In some embodiments, the controlled release layer comprises between about 1% to about 50% of the total weight of the bead. In some embodiments, the controlled release layer comprises between about 2% to about 40% of the total weight of the bead. In some embodiments, the controlled release layer comprises between about 5% to about 30% of the total weight of the bead. In some embodiments, the controlled release layer comprises between about 7% to about 25% of the total weight of the bead. In some embodiments, the controlled release layer comprises between about 8% to about 15% of the total weight of the bead. In some embodiments, the controlled release layer comprises about 8% of the total weight of the bead. In some embodiments, the controlled release layer comprises about 10% of the total weight of the bead. In some embodiments, the controlled release layer comprises about 12% of the total weight of the bead. In some embodiments, the controlled release layer comprises about 15% of the total weight of the bead.

In some embodiments, the application of the controlled release layer causes a weight gain of between about 1% to about 50% of the weight prior to the application of the controlled release layer. Thus, for example, if the weight of the core and active agent layer prior to the application of the controlled release layer is X, then after the application of the controlled release layer, the weight of each bead is 1.01X, if the weight gain is 1%, or the weight of each bead is 1.5X, if the weight gain is 50%. In some embodiments, the weight gain is between about 5% to about 45%. In some embodiments, the weight gain is between about 5% to about 40%. In some embodiments, the weight gain is between about 5% to about 35%. In some embodiments, the weight gain is between about 5% to about 30%. In some embodiments, the weight gain is between about 10% to about 25%, such as 15%.

Certain non-limiting examples of compositions of nafamostat mesylate are provided in Tables 1 and 2 below:

TABLE 1

Composition of Drug Product, Formulations I to IV

| Component | Amount Dose Unit (mg) Formulation I (95:5 RS:RL) | Formulation II (80:20 RS:RL) | Formulation III (80:20 RS:RL) | Formulation IV (95:5 RS:RL) |
|---|---|---|---|---|
| Nafamostat mesylate | 100 | 100 | 1 | 1 |
| Hypromellose capsule | one unit | one unit | one unit | one unit |
| Microcrystalline cellulose spheres | 526.4 | 526.4 | 5.264 | 5.264 |
| Hypromellose | 100 | 100 | 1 | 1 |
| Ammonio methacrylate copolymers type A (Eudragit RL) | 4.5 | 18.1 | 0.181 | 0.045 |
| Ammonio methacrylate copolymers type B (Eudragit RS) | 86.2 | 72.6 | 0.726 | 0.862 |
| Triethyl citrate | 9.1 | 9.1 | 0.091 | 0.091 |
| Talc | 45.4 | 45.4 | 0.454 | 0.454 |
| TOTAL | 871.6 | 871.6 | 8.72 | 8.72 |

Formulation I = High Dose, Slow Release Rate
Formulation II = High Dose, Fast Release Rate
Formulation III = Low Dose, Fast Release Rate
Formulation IV = Low Dose, Slow Release Rate

TABLE 2

| Nafamostat Controlled Release Bead Formulations | | | | |
|---|---|---|---|---|
| | Formulation V (100:0 RS:RL) | Formulation VI (87:13 RS:RL) | Formulation VII (100:0 RS:RL) | Formulaion VIII (93:7 RS:RL) |
| Core | Microcrystalline Cellulose Spheres 63.01% w/w | Microcrystalline Cellulose Spheres 60.3865% w/w | Microcrystalline Cellulose Spheres 60.39% w/w | Microcrystalline Cellulose Spheres 60.3865% w/w |
| Active Agent Layer | Nafamostat 11.97% w/w Hydroxypropyl methylcellulose 11.97% w/w | Nafamostat 11.4734% w/w Hydroxypropyl methylcellulose 11.4734% w/w | Nafamostat 11.47% w/w Hydroxypropyl methylcellulose 11.47% w/w | Nafamostat 11.4734% w/w Hydroxypropyl methylcellulose 11.4734% w/w |
| Controlled Release Layer | Ammonio methacrylate copolymers type B (Eudragit RSPO) 8.15% w/w Ammonio methacrylate copolymers type A (Eudragit RLPO) 0.0% w/w Triethyl Citrate 0.82% w/w Talc 4.08% w/w | Ammonio methacrylate copolymers type B (Eudragit RSPO) 9.0625% w/w Ammonio methacrylate copolymers type A (Eudragit RLPO) 1.3542% w/w Triethyl Citrate 1.0417% w/w Talc 5.2083% w/w | Ammonio methacrylate copolymers type B (Eudragit RSPO) 10.42% w/w Ammonio methacrylate copolymers type A (Eudragit RLPO) 0.0% w/w Triethyl Citrate 1.04% w/w Talc 5.21% w/w | Ammonio methacrylate copolymers type B (Eudragit RSPO) 9.6875% w/w Ammonio methacrylate copolymers type A (Eudragit RLPO) 0.7292% w/w Triethyl Citrate 10.417% w/w Talc 5.2083% w/w |

In some embodiments, the controlled release layer further includes mold release agents, such as glycerol monostearate. In some embodiments, the controlled release layer also contains one or more plasticizers. In some embodiments, the plasticizer is selected from the group consisting of a phthalate-based plasticizer, a trimellitate, an adipate-based plasticizer, a sebacate-based plasticizer, an organophosphate, a maleate, a sulfonamide, a glycols or polyether, an acetylated monoglyceride, and an alkyl citrate. In certain embodiments, the sebacate-based plasticiser is dibutyl sebacate (DBS). In certain embodiments, the plasticizer is triethyl citrate. In some embodiments, the plasticizer is present in between about 1% to about 20% of the weight of the controlled release layer, or between about 5% to about 15% by weight, or between about 7% to about 10% by weight. In certain embodiments, the controlled release layer can further contain a flavouring agent. In certain cases, the active agent layer and/or the controlled release layer comprise magnesium silicate.

In certain embodiments, the plurality of controlled release beads includes an immediate release layer of nafamostat or pharmaceutically acceptable salt thereof that is coated on top of the controlled release layer. In some instances, the immediate release layer of nafamostat or pharmaceutically acceptable salt thereof is formulated to release 50% or more of the nafamostat or pharmaceutically acceptable salt thereof within 10 minutes or less of administration of the composition to the subject, such as 60% or more, such as 75% or more, such as 90% or more, such as 95% or more and including 99% or more within 10 minutes or less of administration of the composition to the subject. In certain instances, the immediate release layer of nafamostat or pharmaceutically acceptable salt thereof is formulated to release all (i.e., 100%) of the nafamostat or pharmaceutically acceptable salt thereof within 10 minutes or less of administration of the composition to the subject. In certain instances, the immediate release layer of nafamostat or pharmaceutically acceptable salt thereof is formulated to release 50% or more of nafamostat or a pharmaceutically acceptable salt thereof immediately after administration of the composition to the subject, such as 60% or more, such as 75% or more, such as 90% or more, such as 95% or more and including 99% or more immediately after administration of the composition to the subject.

The amount of nafamostat or a pharmaceutically acceptable salt thereof present in the immediate release layer of each bead may be 0.000001 mg or more, such as 0.00001 mg or more, such as 0.0001 mg or more, such as 0.001 mg or more, such as 0.01 mg or more, such as 0.1 mg or more, such as 0.5 mg or more, such as 1 mg or more and including 2 mg or more. In some embodiments, the drug loading of nafamostat or pharmaceutically acceptable salt thereof in the immediate release layer of each bead is from 1% w/w to 25% w/w, such as from 2% w/w to 24% w/w, such as from 3% w/w to 23% w/w, such as from 4% w/w to 22% w/w, such as from 5% w/w to 21% w/w, such as from 6% w/w to 20% w/w, such as from 7% w/w to 19% w/w, such as from 8% w/w to 18% w/w, such as from 9% w/w to 15% w/w and including from 11% w/w to 13% w/w.

The oral composition of controlled release nafamostat or pharmaceutically acceptable salt thereof may be formulated in any convenient form suitable for oral (including buccal and sublingual) administration for example as a tablet, capsule, powder, suspension, dispersion or emulsion. The composition can contain components conventional in pharmaceutical preparations, e.g., one or more carriers, binders, lubricants, excipients (e.g., to impart controlled release characteristics), pH modifiers, sweeteners, bulking agents, coloring agents or further active agents as described above. The pharmaceutical composition according to the embodiments can further comprise a pharmaceutically acceptable carrier.

The amount of nafamostat or a pharmaceutically acceptable salt thereof in a unit composition, for example, a capsule of the controlled release nafamostat or pharmaceutically acceptable salt thereof, may include from 1 mg and 500 mg of nafamostat or pharmaceutically acceptable salt thereof, for example, between: 1 and 10 mg, 10 and 20 mg, 20 and 30 mg, 30 and 40 mg, 40 and 50 mg, 50 and 60 mg, 60 and 70 mg, 70 and 80 mg, 80 and 90 mg, 90 and 100 mg, 100 and 110 mg, 110 and 120 mg, 120 and 130 mg, 130 and 140 mg, 140 and 150 mg, 150 and 160 mg, 160 and 170 mg, 170 and 180 mg, 180 and 190 mg, 190 and 200 mg, 200 and 210 mg, 210 and 220 mg, 220 and 230 mg, 230 and 240 mg, 240 and 250 mg, 250 and 260 mg, 260 and 270 mg, 270 and 280 mg, 280 and 290 mg, 290 and 300 mg, 300 and 310 mg, 310 and 320 mg, 320 and 330 mg, 330 and 340 mg, 340 and 350 mg, 350 and 360 mg, 360 and 370 mg, 370 and 380 mg, 380 and 390 mg, 390 and 400 mg, 400 and 410 mg, 410 and 420 mg, 420 and 430 mg, 430 and 440 mg, 440 and 450 mg, 450 and 460 mg, 460 and 470 mg, 470 and 480 mg, 480 and 490 mg and between 490 and 500 mg.

In certain embodiments, the controlled release oral compositions further includes an amount of immediate release nafamostat or pharmaceutically acceptable salt thereof, such as included within a capsule of the controlled release beads. In some instances, the immediate release nafamostat or pharmaceutically acceptable salt thereof is present in the composition (e.g., within the capsule) in form of a powder. In other instances, the immediate release nafamostat or pharmaceutically acceptable salt thereof is present in the composition (e.g., within the capsule) in form of a granulate. The amount of immediate release nafamostat or pharmaceutically acceptable salt thereof present in the oral composition may range from 1 mg to 200 mg, such as from 2 mg to 190 mg, such as from 3 mg to 180 mg, such as from 4 mg to 170 mg, such as from 5 mg to 160 mg, such as from 6 mg to 150 mg, such as from 7 mg to 140 mg, such as from 8 mg to 130 mg, such as from 9 mg to 120 mg and including from 10 mg to 100 mg.

Methods for Administering an Active Agent Prodrug and an Orally Administered Controlled-Release Composition of Nafamostat or Pharmaceutically Acceptable Salt Thereof Aspects of the present disclosure also include methods for administering to a subject an active agent prodrug and a controlled-release composition of nafamostat or a pharmaceutically acceptable salt thereof. In practicing the subject methods according to certain embodiments, one or more doses of the active agent prodrug described herein are orally (including buccally or sublingually) administered with a controlled release nafamostat composition to the subject. The desired protocol used to administer the active agent prodrug and the controlled-release nafamostat composition and the appropriate dosage as described herein may, in certain embodiments, be determined by a qualified healthcare professional (e.g., a physician).

Methods and compositions of the present disclosure can be used in the treatment or prevention of pain including, but not limited to include, acute pain, chronic pain, neuropathic pain, acute traumatic pain, arthritic pain, osteoarthritic pain, rheumatoid arthritic pain, muscular skeletal pain, post-dental surgical pain, dental pain, myofascial pain, cancer pain, visceral pain, diabetic pain, muscular pain, post-herpetic neuralgic pain, chronic pelvic pain, endometriosis pain, pelvic inflammatory pain and child birth related pain. Acute pain includes, but is not limited to, acute traumatic pain or post-surgical pain. Chronic pain includes, but is not limited to, neuropathic pain, arthritic pain, osteoarthritic pain, rheumatoid arthritic pain, muscular skeletal pain, dental pain, myofascial pain, cancer pain, diabetic pain, visceral pain, muscular pain, post-herpetic neuralgic pain, chronic pelvic pain, endometriosis pain, pelvic inflammatory pain and back pain. In certain embodiments, methods and compositions can be used in the treatment of conditions such as, but not limited to, Attention Deficit Hyperactivity Disorder (ADHD), Chronic Fatigue Syndrome (CFS), brain injuries, narcolepsy and obesity.

In some instances, the active agent prodrug is administered simultaneously with the controlled release nafamostat composition. Where the active agent prodrug is administered simultaneously with the controlled release nafamostat composition, the active agent prodrug may be administered as a separate composition (e.g., as a pharmaceutical composition that contains the active agent prodrug and one or more pharmaceutically acceptable excipients) or may be co-formulated with the controlled release nafamostat composition. Where the active agent prodrug is co-formulated with the controlled release nafamostat composition, the two components may be combined in a capsule. In some instances, the two components (i.e., active agent prodrug and nafamostat composition) are co-mixed within the capsule. In other instances, the two components are separated within the capsule, such as with a barrier (e.g., a water soluble membrane).

In some cases, the active agent prodrug and the controlled release nafamostat composition are administered sequentially. In some cases, the controlled release nafamostat composition is orally administered to the subject a predetermined period of time before administering the active agent prodrug. For example, the controlled release nafamostat composition may be orally administered to the subject 1 minute or more before administering the active agent prodrug, such as 2 minutes or more, such as 3 minutes or more, such as 4 minutes or more, such as 5 minutes or more, such as 10 minutes or more, such as 15 minutes or more, such as 30 minutes or more, such as 45 minutes or more, such as 60 minutes or more, such as 2 hours or more, such as 3 hours or more, such as 4 hours or more, such as 6 hours or more, such as 8 hours or more, such as 12 hours or more, such as 16 hours or more, such as 20 hours or more and including administering the controlled release nafamostat composition may be orally administered to the subject 24 hours or more before administering the active agent prodrug.

In some cases, the controlled release nafamostat composition is orally administered to the subject a predetermined period of time after administering the active agent prodrug. For example, the controlled release nafamostat composition may be orally administered to the subject 1 minute or more after administering the active agent prodrug, such as 2 minutes or more, such as 3 minutes or more, such as 4 minutes or more, such as 5 minutes or more, such as 10 minutes or more, such as 15 minutes or more, such as 30 minutes or more, such as 45 minutes or more, such as 60 minutes or more, such as 2 hours or more, such as 3 hours or more, such as 4 hours or more, such as 6 hours or more, such as 8 hours or more, such as 12 hours or more, such as 16 hours or more, such as 20 hours or more and including administering the controlled release nafamostat composition may be orally administered to the subject 24 hours or more after administering the active agent prodrug.

The dosage amount of the active agent prodrug administered to the subject may vary, ranging from about 0.1 mg/kg to 200 mg/kg per day, such as from 0.5 mg/kg to 100 mg/kg per day, such as 1.0 mg/kg to 50 mg/kg per day, such as 2 mg/kg to 40 mg/kg per day, such as 5 mg/kg to 30 mg/kg per day, and including 10 mg/kg to 20 mg/kg per day. In embodiments, the active agent prodrug may be administered to the subject once per day, twice per day, three times per day, four times per day, five times per day or at some other interval. In one embodiment the active agent prodrug is administered at a dose such that the level of the active agent achieved in the blood is in the range of from 0.001 ng/ml to 500 ng/ml, such as from 0.005 ng/ml to 450 ng/ml, such as from 0.01 ng/ml to 400 ng/ml, such as from 0.05 ng/ml to 350 ng/ml, such as from 0.1 ng/ml to 300 ng/ml, such as from 0.5 ng/ml to 250 ng/ml, such as from 1 ng/ml to 200 ng/ml, such as from 1.5 ng/ml to 100 ng/ml, such as from 2 ng/ml to 50 ng/ml and including from 3 ng/ml to 25 ng/ml.

Each treatment interval with the active agent prodrug may be 1 day or longer, such as 2 days or longer, such as 3 days or longer, such as 4 days or longer, such as 5 days or longer, such as 6 days or longer, such as 7 days or longer, such as 2 weeks or longer, such as 3 weeks or longer, such as 4 weeks or longer, such as 8 weeks or longer, such as 12 weeks or longer, such as 16 weeks or longer, such as 20 weeks or longer, such as 24 weeks or longer, such as 28 weeks or longer, such as 32 weeks or longer, such as 36 weeks or longer, such as 40 weeks or longer, such as 44 weeks or longer, such as 48 weeks or longer and including 52 weeks or longer. In certain embodiments, protocols may include multiple dosage intervals. In practicing methods of the present disclosure, treatment regimens may include two or more dosage intervals, such as three or more dosage intervals, such as four or more dosage intervals, such as five or more dosage intervals, including ten or more dosage intervals.

In some instances, the active agent prodrug is administered to the subject once or more per day in a cycle for a duration of 30 days, 29 days, 28 days, 27 days, 26 days, 25 days, 24 days, 23 days, 22 days, 21 days, 20 days, 19 days, 18 days, 17 days, 16 days, 15 days, 14 days, 13 days, 12 days, 11 days, 10 days, 9 days, 8 days, 7 days, 6 days, 5 days, 4 days, 3 days or 2 days or 1 day. In some instances, the active agent prodrug is administered to the subject once per day for a duration of from about 1 day to about 30 days, such as once per day for a duration of from about 1 day to about 28 days, from 1 day to 21 days, from 7 days to 14 days. In certain instances, the active agent prodrug is administered to the subject once per day for a duration of 14 days. In other instances, the active agent prodrug is administered to the subject twice per day for a duration of from about 1 day to about 30 days, such as once per day for a duration of from about 1 day to about 28 days, from 1 day to 21 days, from 7 days to 14 days. In certain instances, the active agent prodrug is administered to the subject twice per day for a duration of 14 days.

The dosage amount of the controlled release nafamostat composition administered to the subject may vary, ranging from about 0.01 mg/kg to 20 mg/kg per day, such as from 0.05 mg/kg to 19 mg/kg per day, such as 0.1 mg/kg to 18 mg/kg per day, such as 0.5 mg/kg to 17 mg/kg per day, such as 1 mg/kg to 16 mg/kg per day, and including 1 mg/kg to 15 mg/kg per day. In embodiments, the controlled release nafamostat composition may be administered to the subject once per day, twice per day, three times per day, four times per day, five times per day or at some other interval.

Each treatment interval with the controlled release nafamostat composition may be 1 day or longer, such as 2 days or longer, such as 3 days or longer, such as 4 days or longer, such as 5 days or longer, such as 6 days or longer, such as 7 days or longer, such as 2 weeks or longer, such as 3 weeks or longer, such as 4 weeks or longer, such as 8 weeks or longer, such as 12 weeks or longer, such as 16 weeks or longer, such as 20 weeks or longer, such as 24 weeks or longer, such as 28 weeks or longer, such as 32 weeks or longer, such as 36 weeks or longer, such as 40 weeks or longer, such as 44 weeks or longer, such as 48 weeks or longer and including 52 weeks or longer. In certain embodiments, protocols may include multiple dosage intervals. In practicing methods of the present disclosure, treatment regimens may include two or more dosage intervals, such as three or more dosage intervals, such as four or more dosage intervals, such as five or more dosage intervals, including ten or more dosage intervals.

In some instances, the controlled release nafamostat composition is administered to the subject once or more per day in a cycle for a duration of 30 days, 29 days, 28 days, 27 days, 26 days, 25 days, 24 days, 23 days, 22 days, 21 days, 20 days, 19 days, 18 days, 17 days, 16 days, 15 days, 14 days, 13 days, 12 days, 11 days, 10 days, 9 days, 8 days, 7 days, 6 days, 5 days, 4 days, 3 days or 2 days or 1 day. In some instances, the controlled release nafamostat composition is administered to the subject once per day for a duration of from about 1 day to about 30 days, such as once per day for a duration of from about 1 day to about 28 days, from 1 day to 21 days, from 7 days to 14 days. In certain instances, the controlled release nafamostat composition is administered to the subject once per day for a duration of 14 days. In other instances, the controlled release nafamostat composition is administered to the subject twice per day for a duration of from about 1 day to about 30 days, such as once per day for a duration of from about 1 day to about 28 days, from 1 day to 21 days, from 7 days to 14 days. In certain instances, the controlled release nafamostat composition is administered to the subject twice per day for a duration of 14 days.

The duration between dosage intervals in a multiple dosage interval treatment protocol may vary, depending on the physiology of the subject or by the treatment protocol as determined by a health care professional. For example, the duration between dosage intervals in a multiple dosage treatment protocol may be predetermined and follow at regular intervals. As such, the time between dosage intervals may vary and may be 1 day or longer, such as 2 days or longer, such as 4 days or longer, such as 6 days or longer, such as 8 days or longer, such as 12 days or longer, such as 16 days or longer and including 24 days or longer. In certain embodiments, multiple dosage interval protocols provide for a time between dosage intervals of 1 week or longer, such as 2 weeks or longer, such as 3 weeks or longer, such as 4 weeks or longer, such as 5 weeks or longer, including 6 weeks or longer.

In some embodiments, dosing is administered in cycles of administration of an active agent prodrug and the controlled release nafamostat composition. In some embodiments, the cycle is 21 days or more, in some instances the cycle is 28 days or more. The cycles of drug administration may be repeated for 1, 2, 3, 4, 5, 6, 7, 8 or more than 8 dosage cycles, for a total period of 6 months or 1 year or 2 years or 3 years or 4 years or more. This administration cycle may be repeated, such as 2 or more times, such as 3 or more times, such as 4 or more times, such as 5 or more times, such as 6 or more time, such as 7 or more times, such as 8 or more times, such as 9 or more times and including 10 or more times.

Aspects, including embodiments, of the subject matter described herein may be beneficial alone or in combination, with one or more other aspects or embodiments. Without limiting the description, certain non-limiting aspects of the disclosure numbered 1-34 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A composition comprising:

an active agent prodrug comprising an active agent covalently bound to a promoiety comprising a GI enzyme-cleavable moiety, wherein cleavage of the GI enzyme-cleavable moiety by GI enzyme mediates release of the active agent; and an oral composition comprising nafamostat or a pharmaceutically acceptable salt thereof, wherein the composition provides for controlled release of the nafamostat or pharmaceutically acceptable salt thereof to a subject for an extended period of time.

2. The composition of 1, wherein the nafamostat composition comprises a plurality of controlled release beads, each bead comprising:

a core;

an active agent layer comprising nafamostat or a pharmaceutically acceptable salt thereof; and a controlled release layer comprising one or more polymers formulated in an amount sufficient to provide for controlled release of the nafamostat or pharmaceutically acceptable salt thereof.

3. The composition of 2, wherein the core comprises a cellulose polymer, or silicon dioxide, or a sugar selected from the group consisting of glucose, sucrose, lactose, mannitol, xylitol, and sorbitol.

4. The composition of 3, wherein the core comprises microcrystalline cellulose (MCC).

5. The composition of any one of 1-4, wherein the active agent layer further comprises a binder.

6. The composition of any one of 1-4, wherein the binder comprises hydroxypropyl methylcellulose.

7. The composition of any one of 1-6, wherein the controlled release layer comprises an acrylate copolymer.

8. The composition of 7, wherein the acrylate copolymer comprises poly(ethylacrylate, methyl-methacrylate and chlorotrimethyl-ammonioethyl methacrylate).

9. The composition of 8, wherein the acrylate copolymer comprises poly(ethylacrylate, methyl-methacrylate and chlorotrimethyl-ammonioethyl methacrylate) containing quaternary ammonium groups.

10. The composition of 9, wherein the acrylate copolymer comprises a combination of:

acrylate copolymer A comprising poly(ethylacrylate, methyl-methacrylate and chlorotrimethyl-ammonioethyl methacrylate) comprising about 50 mEq of quaternary ammonium groups per 100 g of polymer; and acrylate copolymer B comprising poly(ethylacrylate, methyl-methacrylate and chlorotrimethyl-ammonioethyl methacrylate) comprising about 25 mEq of quaternary ammonium groups per 100 g of polymer.

11. The composition of 10, wherein the acrylate copolymer comprises 20% by weight acrylate copolymer B and 80% by weight acrylate copolymer A.

12. The composition of 10, wherein the acrylate copolymer comprises 50% by weight acrylate copolymer B and 50% by weight acrylate copolymer A.

13. The composition of 10, wherein the acrylate copolymer comprises 80% by weight acrylate copolymer B and 20% by weight acrylate copolymer A.

14. The composition of 10, wherein the acrylate copolymer comprises 100% by weight acrylate copolymer A.

15. The composition of 10, wherein the acrylate copolymer comprises 100% by weight acrylate copolymer B.

16. The composition of 10, wherein the acrylate copolymer comprises 95% by weight acrylate copolymer B and 5% by weight acrylate copolymer A.

17. The composition of 10, wherein the acrylate copolymer comprises 93% by weight acrylate copolymer B and 7% by weight acrylate copolymer A.

18. The composition of 10, wherein the acrylate copolymer comprises 92% by weight acrylate copolymer B and 8% by weight acrylate copolymer A.

19. The composition of 10, wherein the acrylate copolymer comprises 90% by weight acrylate copolymer B and 10% by weight acrylate copolymer A.

20. The composition of 10, wherein the acrylate copolymer comprises 87% by weight acrylate copolymer B and 13% by weight acrylate copolymer A.

21. The composition of any of 7 to 20, wherein the acrylate copolymer comprises from 5% and 30% by weight of each of the plurality of beads.

22. The composition of any of 2 to 21, wherein one or more of the active agent layer and the controlled release layer further comprise magnesium silicate.

23. The composition of any of 2 to 22, wherein one or more of the active agent layer and the controlled release layer further comprise a plasticizer.

24. The composition of 23, wherein the plasticizer is triethyl citrate.

25. The composition of any of 2 to 24, wherein each of the plurality of beads comprises from 5% and 20% by weight of the nafamostat or a pharmaceutically acceptable salt thereof.

26. The composition of 25, wherein each of the plurality of beads comprises from 10% to 15% by weight of the nafamostat or a pharmaceutically acceptable salt thereof.

27. The composition of 25, wherein each of the plurality of beads comprises from 11% to 12% by weight of the nafamostat or a pharmaceutically acceptable salt thereof.

28. The composition according to any one of 1-27, wherein the plurality of beads are configured to release 50% or more of the nafamostat or pharmaceutically acceptable salt thereof within 6 hours after administration.

29. The composition according to any one of 1-27, wherein the plurality of beads are configured to release 75% or more of the nafamostat or pharmaceutically acceptable salt thereof within 6 hours after administration.

30. The composition according to any one of 1-27, wherein the plurality of beads are configured to release 90% or more of the nafamostat or pharmaceutically acceptable salt thereof within 6 hours after administration.

31. The composition according to any one of 1-27, wherein the plurality of beads are configured to provide for release of nafamostat or pharmaceutically acceptable salt thereof at a first rate for a first predetermined period of time followed by release of the nafamostat or pharmaceutically acceptable salt thereof at a second rate for a second predetermined period of time.

32. The composition of any of 1 to 31, further comprising nafamostat or a pharmaceutically acceptable salt thereof in an immediate release form that provides for an immediate release of nafamostat or pharmaceutically acceptable salt thereof to the subject.

33. The composition of 32, wherein the nafamostat or a pharmaceutically acceptable salt thereof in the immediate release form comprises nafamostat or a pharmaceutically acceptable salt thereof in a powder form.

34. The composition of 32, wherein nafamostat or a pharmaceutically acceptable salt thereof in the immediate release form comprises a layer of nafamostat or a pharmaceutically acceptable salt thereof positioned over the controlled release layer of the plurality of the controlled release beads.

35. The composition of 32, wherein nafamostat or a pharmaceutically acceptable salt thereof in the immediate release form comprises a plurality of immediate release beads.

36. The composition of any one of 1-35, wherein the active agent prodrug is a compound of formula KC-(IIIa):

(KC-(IIIa))

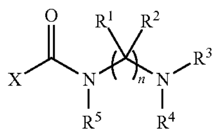

wherein:

X represents a residue of a ketone-containing opioid, wherein the hydrogen atom of the corresponding enolic group of the ketone is replaced by a covalent bond to $—C(O)—NR^5—(C(R^1)(R^2))_n—NR^3R^4$;

$R^5$ is selected from alkyl, substituted alkyl, arylalkyl, substituted arylalkyl, aryl and substituted aryl;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl, substituted cycloalkyl, aryl, or substituted aryl group, or two $R^2$ or $R^3$ groups on adjacent carbon atoms, together with the carbon atoms to which they are attached, form a cycloalkyl, substituted cycloalkyl, aryl, or substituted aryl group;

n is an integer from 2 to 4;

$R^3$ is hydrogen or (1-4C) alkyl;

$R^4$ is

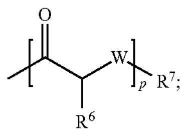

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;

each W is independently $—NR^8—$, —O— or —S—;

each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

p is an integer from one to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate. Thereof

37. The composition of 36, wherein the ketone-containing opioid is selected from acetylmorphine, hydrocodone, hydromorphone, ketobemidone, methadone, naloxone, N-methylnaloxone, naltrexone, N-methylnaltrexone, oxycodone, oxymorphone, and pentamorphine.

38. The composition of 37, wherein the ketone-containing opioid is selected from oxycodone, hydrocodone and methadone.

39. The composition of any one of 36-38, wherein $R^5$ is methyl or ethyl.

40. The composition of any one of 36-39, wherein $R^5$ is methyl.

41. The composition of any one of 36-40, wherein $R^1$ and $R^2$ are hydrogen.

42. The composition of any one of 36-41, wherein $R^1$ and $R^2$ which are on the same carbon are alkyl.

43. The composition of 42, wherein $R^1$ and $R^2$ which are on the same carbon are methyl.

44. The composition of any one of 36-42, wherein $R^1$ and $R^1$ which are vicinal are both alkyl and $R^2$ and $R^2$ which are vicinal are both hydrogen.

45. The composition of 44, wherein $R^1$ and $R^1$ which are vicinal are both methyl and $R^2$ and $R^2$ which are vicinal are both hydrogen.

46. The composition of any one of 37-45, wherein n is 2 or 3.

47. The composition of any one of 37-46, wherein $R^4$ is a residue of an L-amino acid selected from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine, or a residue of an N-acyl derivative of any of said amino acids; or a residue of a peptide composed of at least two L-amino acid residues selected independently from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine or a residue of an N-acyl derivative thereof.

48. The composition of 47, wherein the N-acyl derivative is an acetyl, benzoyl, malonyl, piperonyl or succinyl derivative.

49. The composition of 48, wherein $R^4$ is a residue of L-arginine or L-lysine, or a residue of an N-acyl derivative of L-arginine or L-lysine.

50. The composition of 36, wherein the opioid prodrug is N-1-[3-(Oxycodone-6-enol-carbonyl-methyl-amino)-2,2-dimethyl-propylamine]-arginine-glycine-malonic acid, Compound KC-8, shown below:

(KC-8)

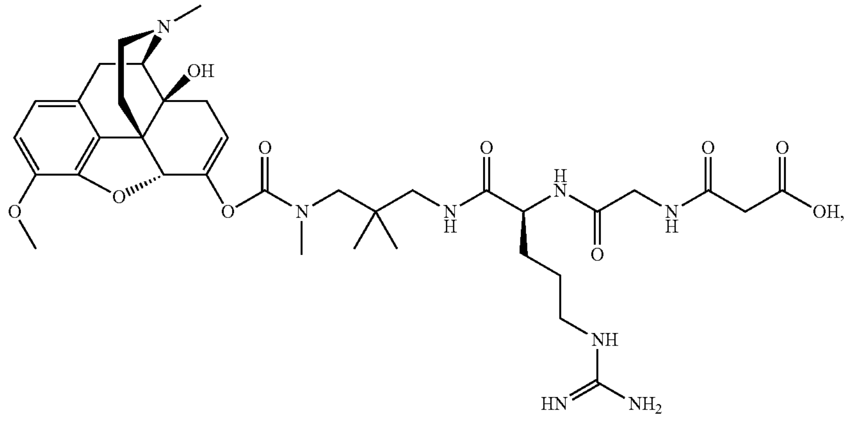

or acceptable salt, solvate, or hydrate thereof.

51. The composition of any one of 1-35, wherein the active agent prodrug is a compound of formula PC-(I)

$$X—C(O)—NR^1—(C(R^2)(R^3))_n—NH—C(O)—CH(R^4)—NH(R^5) \quad (PC-(I))$$

or a pharmaceutically acceptable salt thereof, wherein:

X represents a residue of a phenolic opioid, wherein the hydrogen atom of the phenolic hydroxyl group is replaced by a covalent bond to —C(O)—$NR^1$—(C($R^2$)($R^3$))$_n$—NH—C(O)—CH($R^4$)—NH($R^5$);

$R^1$ represents a (1-4C)alkyl group;

$R^2$ and $R^3$ each independently represents a hydrogen atom or a (1-4C)alkyl group; n represents 2 or 3;

$R^4$ represents $—CH_2CH_2CH_2NH(C{=}NH)NH_2$ or $—CH_2CH_2CH_2CH_2NH_2$, the configuration of the carbon atom to which $R^4$ is attached corresponding with that in an L-amino acid; and $R^5$ represents a hydrogen atom, an N-acyl group, or a residue of an amino acid, a dipeptide, or an N-acyl derivative of an amino acid or dipeptide.

52. The composition of 51, wherein X is oxymorphone, hydromorphone or morphine.

53. The composition of any one of 51-52, wherein $R^5$ is methyl or ethyl.

54. The composition of any one of 51-53, wherein $R^3$ is hydrogen or methyl.

55. The composition of any one of 51-54, in which $R^4$ is a residue of arginine or N-acetylarginine, 56. The composition of any one of 51-54, in which $R^4$ is a residue of lysine or N-acetyllysine.

57. The composition of 51, wherein the active agent prodrug comprises hydromorphone 3-(N-methyl-N-(2-N'-acetylarginylamino))ethylcarbamate, or a pharmaceutically acceptable salt thereof.

58. The composition of 51, wherein the active agent prodrug comprises oxymorphone 3-(N-methyl-N-(2-N'-acetylarginylamino))ethylcarbamate, or a pharmaceutically acceptable salt thereof.

59. The composition of 51, wherein the active agent prodrug comprises morphine 3-(N-methyl-N-(2-N'-acetylarginylamino))ethylcarbamate, or a pharmaceutically acceptable salt thereof.

60. The composition of any one of 1-35, wherein the active agent prodrug is a compound of formula AM-(I):

AM-(I)

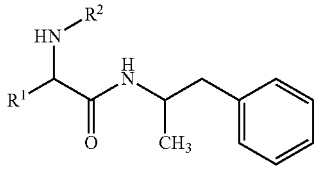

wherein $R^1$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl; and $R^2$ is an acyl, substituted acyl, or an N-acyl derivative of a peptide;

or a salt, hydrate or solvate thereof.

61. The composition of 60, wherein $R^1$ is $—CH_2CH_2CH_2NH(C{=}NH)NH_2$ or $—CH_2CH_2CH_2CH_2NH_2$, the configuration of the carbon atom to which $R^1$ is attached corresponding with that in an L-amino acid.

62. The composition of any one of 60-61, wherein $R^2$ is acetyl, benzoyl, malonyl, piperonyl or succinyl.

63. The composition of 62, wherein $R^2$ is acetyl or malonyl.

64. The composition of any one of 60-63, wherein $R^2$ is a peptide of the formula $(R^4)_p$, wherein p is an integer from 1 to 100 and each $R^4$ is an independently selected amino acid, wherein the $R^4$ at the terminal end of the peptide is N-acylated.

65. The composition of 64, wherein $R^2$ is acylated with a group selected from acetyl, benzoyl, malonyl, piperonyl and succinyl.

66. The composition of 60, wherein the active agent prodrug comprises a compound selected from Compound AM-1, Compound AM-2 and Compound AM-5:

Compound AM-1

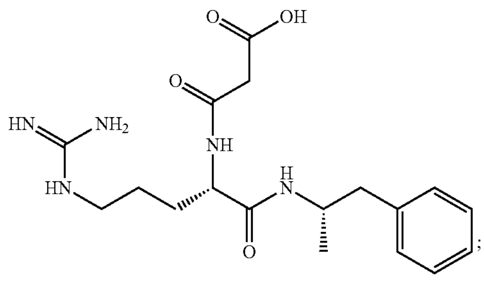

;

Compound AM-2

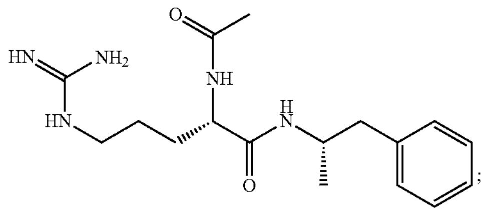

; and

Compound AM-5

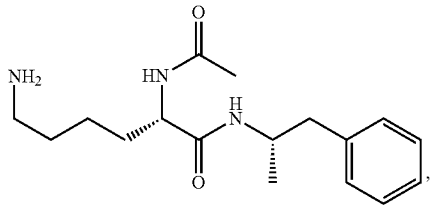

, or a salt, hydrate or solvate thereof.

67. The composition of 60, wherein the active agent prodrug comprises Compound AM-9:

(AM-9)

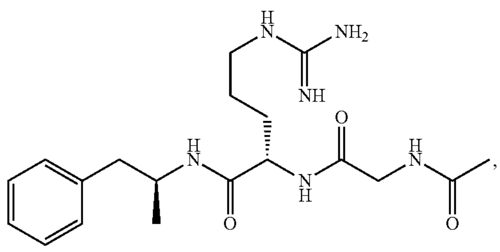

, or a salt, hydrate or solvate thereof.

68. The composition of 60, wherein the active agent prodrug comprises Compound AM-10.

(AM-10)

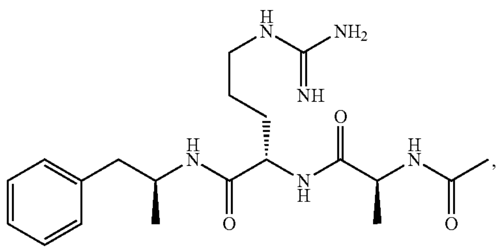

, or a salt, hydrate or solvate thereof.

69. The composition of any one of 1-68, wherein the active agent prodrug and controlled release nafamostat composition are co-formulated.

70. The composition of 69, wherein the active agent prodrug and the controlled release nafamostat composition are present together in a capsule.

71. The composition of 70, wherein the active agent prodrug and the controlled release nafamostat composition are mixed together in the capsule.

72. A method comprising administering to a subject in need thereof a composition of any one of 1-71.

73. The method of 72, wherein the active agent prodrug and the nafamostat composition are administered simultaneously.

74. The method of 72, wherein the active agent prodrug and the nafamostat composition are administered sequentially.

75. The method of 74, wherein the active agent prodrug is administered to the subject at a predetermined period of time before the nafamostat composition is administered.

76. The method of 75, wherein the active agent prodrug is administered to the subject 0.5 hour or more before the nafamostat composition is administered.

77. The method of 75, wherein the active agent prodrug is administered to the subject 1 hour or more before the nafamostat composition is administered.

78. The method of 74, wherein the active agent prodrug is administered to the subject at a predetermined period of time after the nafamostat composition is administered.

79. The method of 78, wherein the active agent prodrug is administered to the subject 1 hour or more after the nafamostat composition is administered.

80. The method of 78, wherein the active agent prodrug is administered to the subject 2 hours or more after the nafamostat composition is administered.

81. The method of any one of 72-80, wherein the active agent prodrug is administered to the subject in an amount of from 0.1 mg/kg per day to 100 mg/kg per day.

82. The method of any one of 72-81, wherein the active agent prodrug is administered to the subject for 7 days or longer.

83. The method of any one of 72-82, wherein the dosage amount of nafamostat administered to the subject is from 0.01 mg/kg per day to 20 mg/kg per day.

84. The method of any one of 72-83, wherein the nafamostat composition is administered to the subject for 7 days or longer.

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used.

The oxycodone-derivative used in the present experiments is KC-8 (N-1-[3-(oxycodone-6-enol-carbonyl-methyl-amino)-2,2-dimethyl-propylamine]-arginine-glycine-malonic acid), as described above. The left side of the molecule is the oxycodone group. Moving to the right is a linker with structure $—C(O)N(CH_3)CH_2C(CH_3)_2CH_2—$ followed by a peptide of the formula Arg-Gly-Mal.

concentration of about 1.3 or 1.4 ng/ml. In contrast, additional nafamostat reduced the maximum oxycodone concentration to a peak of about 0.75 ng/ml at about 5 hours. The error bars represent one standard deviation.

Figure 2:
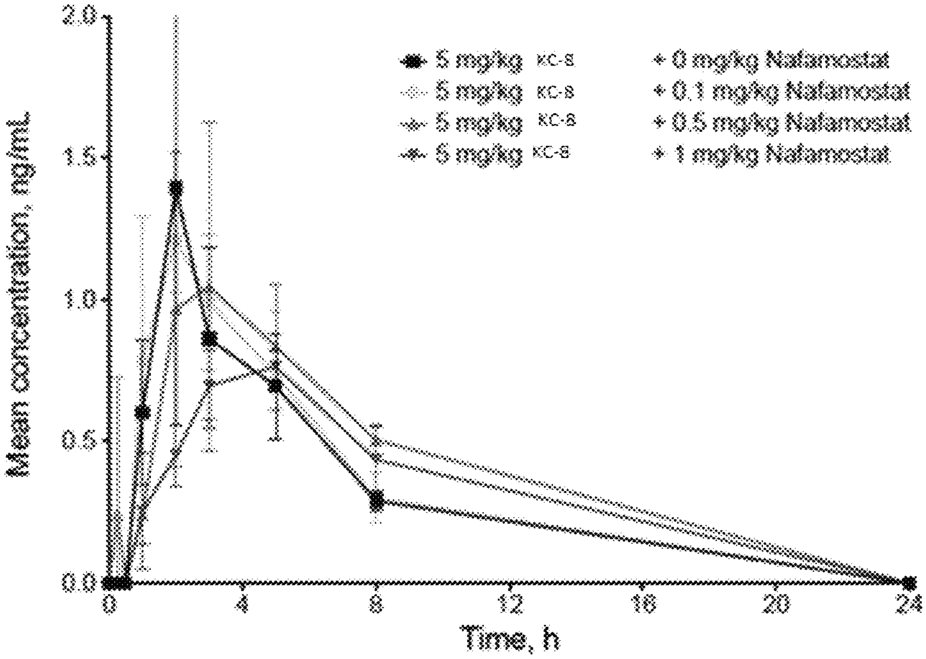
FIG. 2 shows the mean blood concentration of oxycodone in rats that were orally administered 5 mg/kg of the oxycodone derivative KC-8 with either 0, 0.1, 0.5, or 1 mg/kg of nafamostat over time.
Figure 3:
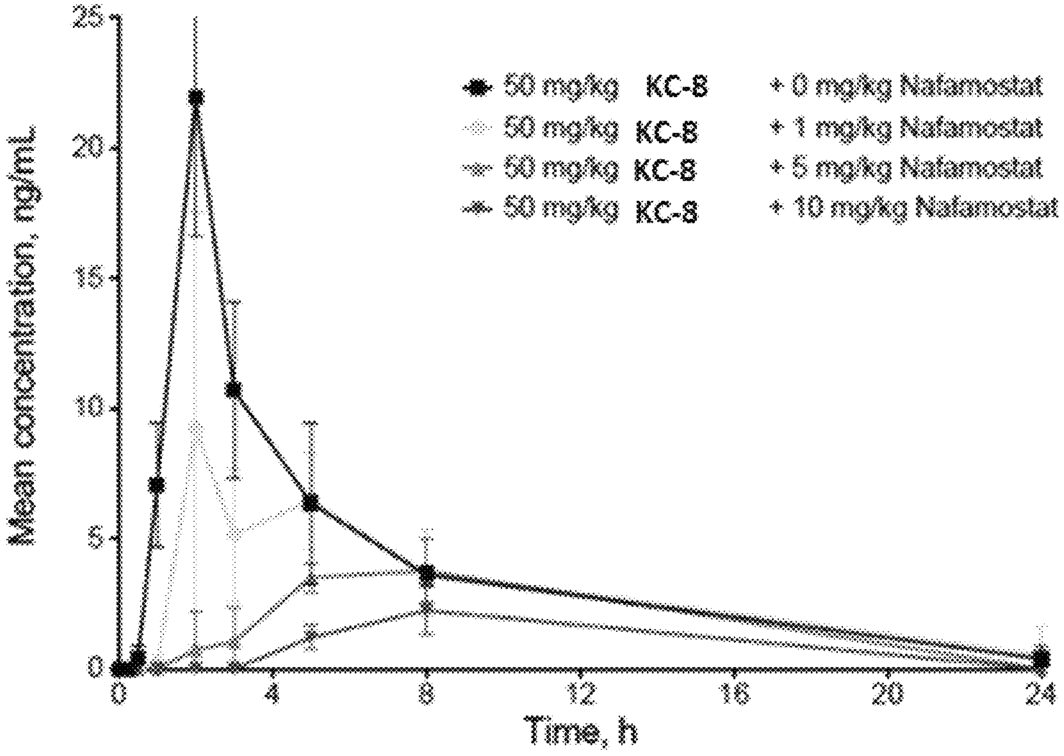
FIG. 3 shows the mean blood concentration of oxycodone in rats that were orally administered 50 mg/kg of the oxycodone derivative KC-8 with either 0, 1, 5, or 10 mg/kg of nafamostat over time.

As shown in FIG. 3, rats were administered higher concentrations of both KC-8 and nafamostat that are approximately equal to the dose a human would receive if ingesting 10 pills of KC-8. In particular, the rats received 50 mg/kg of KC-8 and 0, 1, 5, or 10 mg/kg of nafamostat. With zero nafamostat, blood plasma concentration experienced a maximum of about 22 ng/ml at about 2 hours, wherein the concentration rapidly descended thereafter. In alignment with the data of FIG. 2, higher concentrations of nafamostat reduced the peak concentration to about 3 ng/ml at about 8 hours.

The rat experiments were repeated with a derivative of hydromorphone (referred to herein as PF329), which is (KC-8)

Figure 4:
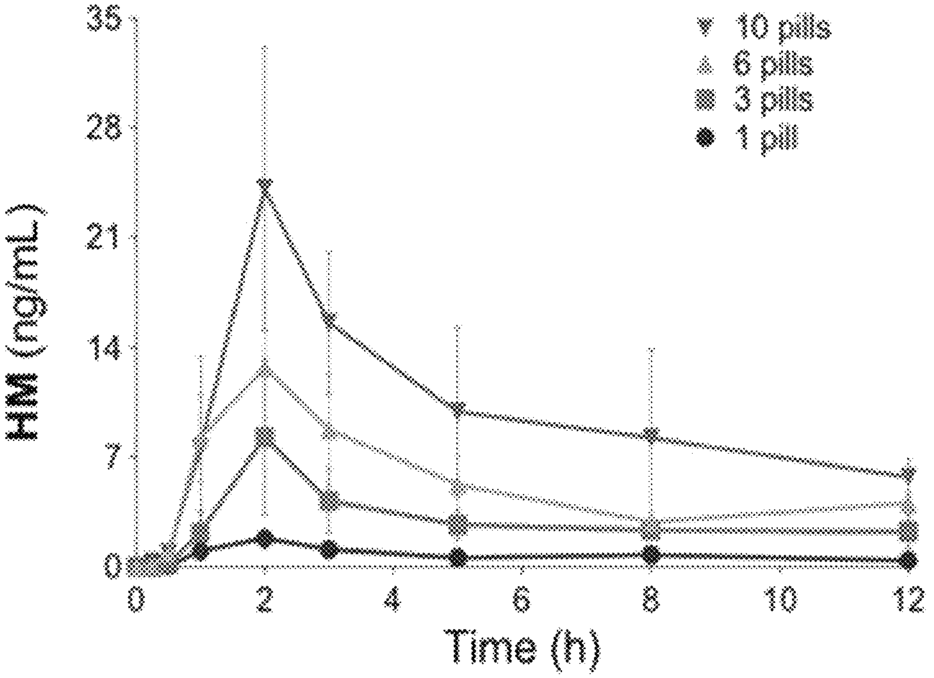
FIG. 4 shows the mean blood concentration of hydromorphone in rats that were orally administered 1, 3, 6, or 10 pills of a hydromorphone derivative but no nafamostat.
Figure 5:
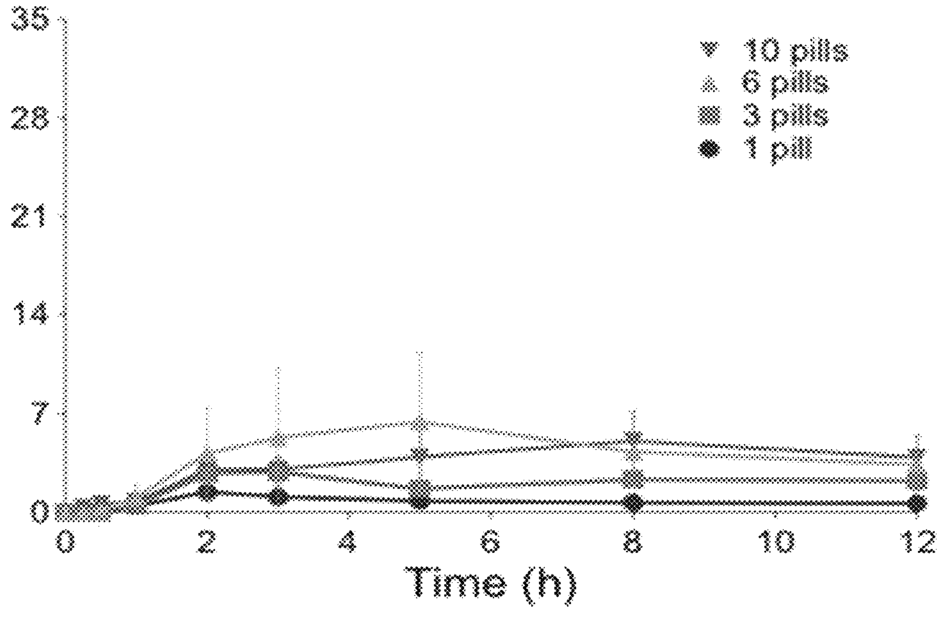
FIG. 5 shows the mean blood concentration of hydromorphone in rats that were orally administered 1, 3, 6, or 10 pills of a hydromorphone derivative that also contained nafamostat.

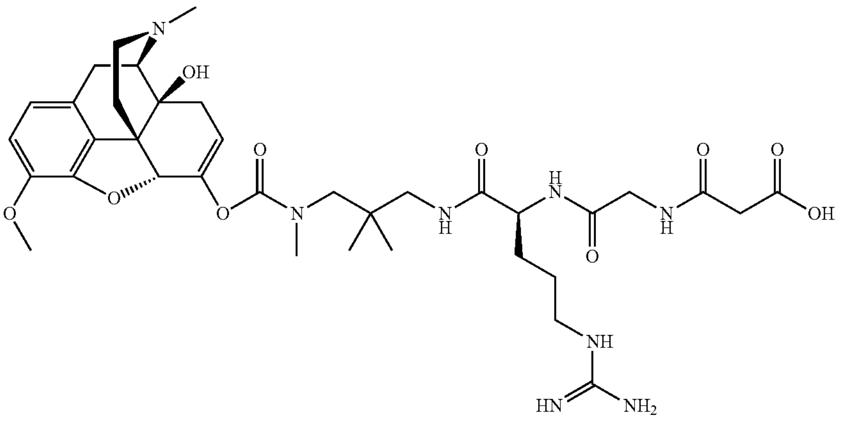

another known pain medication. FIGS. 4 and 5 show the blood concentration of active hydromorphone (HM) after the administration of 1, 3, 6, or 10 pills, either without or with nafamostat. In other words, the FIG. 5 pills contained nafamostat whereas the FIG. 4 pills did not. The figures show that administering more pills in FIG. 4 resulted in a significant increase in hydromorphone concentration, but in FIG. 5 there was little increase due to the moderating effects of nafamostat.

FIG. 1 shows how KC-8 can be activated by the digestive system. First, the N—C bond between the linker and the peptide group is cleaved or bioactivated by the digestive enzyme trypsin. As such, KC-8 can be referred to as trypsin activated. Next, after the terminal amine group of the linker has been separated from the peptide protecting group, the linker undergoes an intramolecular cyclization, thereby releasing a cyclic urea byproduct. As a result, the oxycodone molecule is formed, which can then cause pharmacological effects such as pain inhibition. As such, generation of the active oxycodone drug can be caused by cleavage of the N—C bond by trypsin, which is an enzyme located in the digestive tract.

Example 1: Effect of Nafamostat on Pharmacokinetics of KC-8 in Rats

The drug nafamostat mesylate was added to the formulations containing the KC-8 oxycodone-derivative. In the examples described herein, the terms “nafamostat mesylate” and “nafamostat” are used interchangeably.

Formulations containing both KC-8 and optionally nafamostat were administered orally to rats. The KC-8 dose was 5 mg/kg and the nafamostat concentration was 0, 0.1, 0.5, or 1 mg/kg. Plasma concentrations of active oxycodone were measured at various time intervals over 24 hours after administration.

As shown in FIG. 2, with 0 or 0.1 mg/kg of nafamostat the oxycodone concentration spiked at about 2 hours with a Thus, Experiment 1 showed that co-administering nafamostat with an oxycodone or hydromorphone derivative significantly reduced the maximum concentration of active drug in blood plasma and also resulted in a more stable concentration of the active drug over time.

Example 2: Effect of Nafamostat on Pharmacokinetics of KC-8 in Humans

Figure 6:
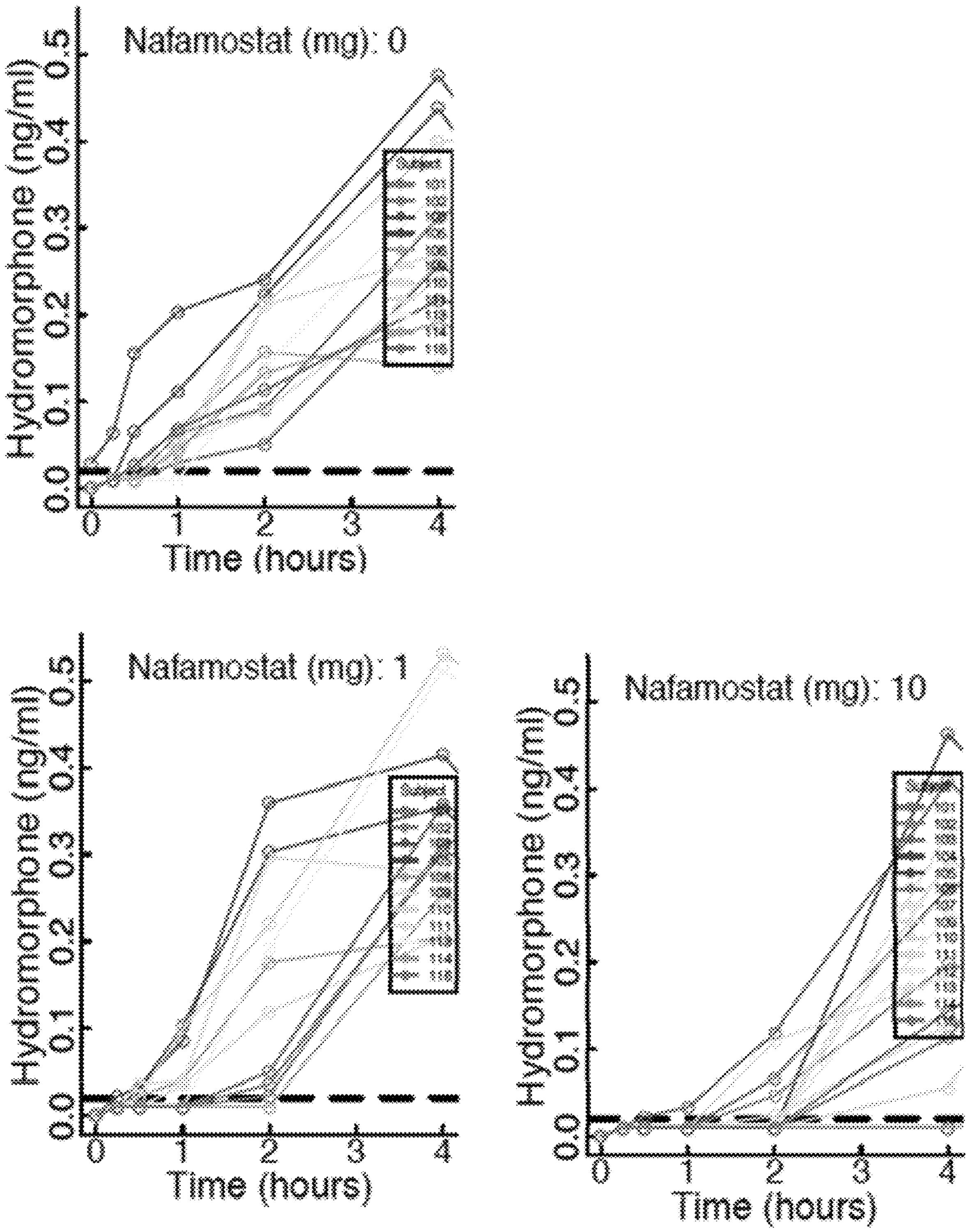
FIG. 6 shows the blood concentration of multiple human patients of hydromorphone after being administered a hydromorphone derivative and 0, 1, or 10 mg of nafamostat.

Whereas the Example 1 experiments tested the effect of nafamostat in rats, Experiment 2 measured the effect when administered to humans. The pharmacokinetics in humans appeared to be different than in rats. As shown in FIG. 6, the hydromorphone derivative of PF329 was administered with 0, 1, or 10 mg of nafamostat. With 0 mg of nafamostat, the blood concentration of hydromorphone increased starting at 0 hours and reaching about 0.4 ng/ml. With 1 or 10 mg of nafamostat, the increase was delayed until 1 or 2 hours, but the peak concentration appeared to also reach about 0.4 ng/ml. Thus, it appeared that the effect of nafamostat in humans was different than in rats.

Example 3: Preparation of Immediate Release Nafamostat Composition

Nafamostat compositions containing immediate release beads were prepared. Each immediate release bead includes a microcrystalline cellulose core and an active agent layer of nafamostat mesylate.

A coating solution of nafamostat mesylate was prepared by adding methocel to water and leaving to stir at 250 rpm for 25 minutes. 29 g of nafamostat mesylate was slowly added and stirred for a further 5 minutes until fully dissolved. This produced a 5 wt % nafamostat mesylate solution. The remaining nafamostat mesylate was then added over another 10 minutes and mixed for another 10 minutes to yield a white uniform suspension. The suspension was left stirring overnight. The coating solution was placed onto a top pan balance and an overhead stirrer was set up to ensure the solution remained fully dispersed throughout the coating process. The components of the immediate release Nafamostat coating composition is summarized in Table 3.

TABLE 3

Immediate release Nafamostat mesylate coating solution

| Component | % w/w | Quantity per 1000 g batch (g) |
|---|---|---|
| Nafamostat mesylate | 13.64 (8.80)[1] | 150.00 (96.80)[1] |
| Methocel E5 | 0.45 | 5.00 |
| Water for irrigation* | 85.91 | 945.00[2] |
| Total solution | 100.0000 | 1100.00 |

*Removed during the process
[1]Amount of free drug based on salt correction of 1.55
[2]incorrect amount of water used, 14.09% solids content instead of 15.5%

700 g of MCC CP-305 spheres were weighed out and loaded into the vessel and coating commenced. The pump speed was gradually increased from 1 g/min every 10-20 minutes until a maximum spray rate was achieved. A blow back cycle was not required. Coating was carried out for a total of 4.75 hours without any significant twinning or clumping being observed. The beads were cured for 30 minutes prior to collection. The processing parameters are presented in Table 4. The beads were collected passed through a 600 μm sieve, 698 g acceptable individual beads were collected, while 72 g twinned beads were collected.

TABLE 4

Coating parameters for Immediate release Nafamostat mesylate coating solutions

| | Set point | |
|---|---|---|
| Parameter | Batch 1 | Batch 2 |
| Drying air speed ($m^3$ $min^{-1}$) | 0.20-0.45 | 0.20-0.35 |
| Air inlet temperature (° C.) | 71.9 (61.8-84.6) | 72.3 (63.0-78.0) |
| Product temperature (° C.) | 48.9 (47.5-51.4) | 47.5 (45.7-49.0) |
| Nozzle pressure (bar) | 0.75 (0.42-1.24) | 0.94 (0.47-1.00) |
| Nozzle flow rate (L $min^{-1}$) | 4.9 (2.9-5.5) | 5.3 (3.4-5.5) |
| Pump flow rate (g $min^{-1}$) | 0.44-2.96 | 086-2.67 |

The beads were collected and passed through a 600 μm sieve, 698 g individual beads were collected, while 72 g were twinned. In total 702 g coating solution was sprayed, a theoretical free drug loading of 7.99% w/w was achieved. Beads were tested for LOD, Assay, related substance and water content. The beads showed good uniformity indicating that an even coating had been achieved.

Example 4: Preparation of Active Agent Layer of Controlled Release Nafamostat Compositions The active agent layer of the Nafamostat controlled release beads were prepared. Each bead was prepared from a microcrystalline cellulose core and a coating layer of nafamostat mesylate. The composition of the coating solution is shown in Table 5.

TABLE 5

Active agent layer of Nafamostat controlled release beads coating solution

| Component | % w/w | Quantity per 1000 g batch (g) |
|---|---|---|
| Nafamostat mesylate | 13.64 (8.80)[1] | 150.00 (96.80)[1] |
| Methocel E5 | 0.45 | 5.00 |
| Water for irrigation* | 85.91 | 945.00[2] |
| Total solution | 100.0000 | 1100.00 |

*Removed during the process
[1]Amount of free drug based on salt correction of 1.55
[2]incorrect amount of water used, 14.09% solids content instead of 15.5%

The coating solution of nafamostat mesylate was prepared as described above for the immediate release nafamostat bead compositions and was left stirring overnight. 650 grams of microcrystalline cellulose CP-305 spheres were weighed out and loaded into the vessel and coating commenced. The pump speed was maintained at 1 g/min for 15 minutes before it was increased to 1.5 g/min. The pump speed was gradually increased to 3.0 g/min over the next hour based on observations made. During this time the nozzle pressure was gradually increased in line with the pump speed to maintain a good spray pattern. In total the process ran for 4.5 hours without any blockages or the need for the blowback feature. The beads were cured in the fluid bed vessel at 40° C. for 30 minutes, coating parameters are as presented in Table 4.

The beads were collected and passed through a 600 μm sieve, 532 g individual beads were collected, while 194 g were twinned. In total 655 g coating solution was sprayed, a theoretical free drug loading of 8.40% w/w was achieved. Beads were tested for LOD, Assay, related substance and water content.

Example 6: Preparation of Controlled Release Nafamostat Compositions

Nafamostat compositions containing controlled release beads were prepared. Each controlled release bead includes a microcrystalline cellulose core and an active agent layer of nafamostat mesylate and a controlled release polymeric coating layer. The active agent layer of nafamostat mesylate was prepared as set forth in Example 4. A polymeric controlled release coating solution with an 87:13 ratio of Eudragit RS:Eudragit RL was prepared as summarized in Table 6. In another embodiment, the proportion of talc in the solution was halved relative to the other components as shown in Table 7.

TABLE 6

Controlled release polymer layer of Nafamostat controlled release beads coating solution (87:13 Eudragit RS:Eudragit RL)

| Component | % w/w | Quantity per 300 g batch (g)[1] |
|---|---|---|
| Eudragit RS PO | 3.2625 | 27.1875 |
| Eudragit RL PO | 0.4875 | 4.0625 |
| Triethyl Citrate | 0.3750 | 3.1250 |
| Micronized Talc | 1.8750 | 15.6250 |
| Acetone*,[2] | 35.8140 | 298.4500 |
| Isopropanol, Anhydrous*,[2] | 53.7022 | 447.5183 |
| Water for irrigation*,[2] | 4.4838 | 37.3650 |
| Total solution | 100.0000 | 833.3330 |
| Nafamostat Intermediate IR Beads | | 250.0000 |

*Removed during the process
[1]drug layering solution 6% solids
[2]Acetone/Isopropanol/water = 38.10:57.13:4.77 ratio

TABLE 7

Controlled release polymer layer of Nafamostat controlled release beads coating solution (87:13 Eudragit RS:Eudragit RL)

| Component | % w/w | Quantity per batch (g)[1] |
|---|---|---|
| Eudragit RS PO | 6.266 | 54.37 |
| Eudragit RL PO | 0.937 | 8.13 |
| Triethyl Citrate | 0.72 | 6.25 |
| Micronized Talc | 1.8 | 15.62 |
| Acetone*,[2] | 34.395 | 298.45 |
| Isopropanol, Anhydrous*,[2] | 51.575 | 447.52 |
| Water for irrigation*,[2] | 4.307 | 37.37 |
| Total solution | 100.000 | 867.71 |

*Removed during the process
[1]ER coating suspension 9.72% solids
[2]Acetone/Isopropanol/water = 38.10:57.13:4.77 ratio A Procept Fluid Bed was set up, using the 1 L vessel, 0.4 mm nozzle and no wurster column. 250 g of active agent layer containing beads (microcrystalline cellulose coated with nafamostat mesylate prepared as described above) were weighed out and loaded into the vessel. The coating solution was prepared producing a white opaque solution that was uniformly dispersed. The coating solution was placed onto a top pan balance and an overhead stirrer was set up at 250 rpm to ensure the solution remained fully dispersed throughout the coating process. The coating solution was primed into the line and gun to check for leaks/air bubbles.

Coating was started at an initial spray rate of 0.5 g/min, this was gradually increased throughout the duration of the coating process until a maximum of 2.5 g/min was achieved. Significant static issues were observed, with lots of beads sticking to the inside of the vessel and onto the filters. A static gun had to be used almost constantly to ensure the beads did not build up and stop flowing. After 2.5 hours the process was stopped as clumps of beads had started to form. It was noted that the talc had sedimented in the line, possibly contributing to the clumping of the beads. Approximately 207 g coating solution was sprayed resulting in a coating weight gain of 4.73%. Using a 600 um sieve, the ER coated beads were screened for twins.

Figure 12:
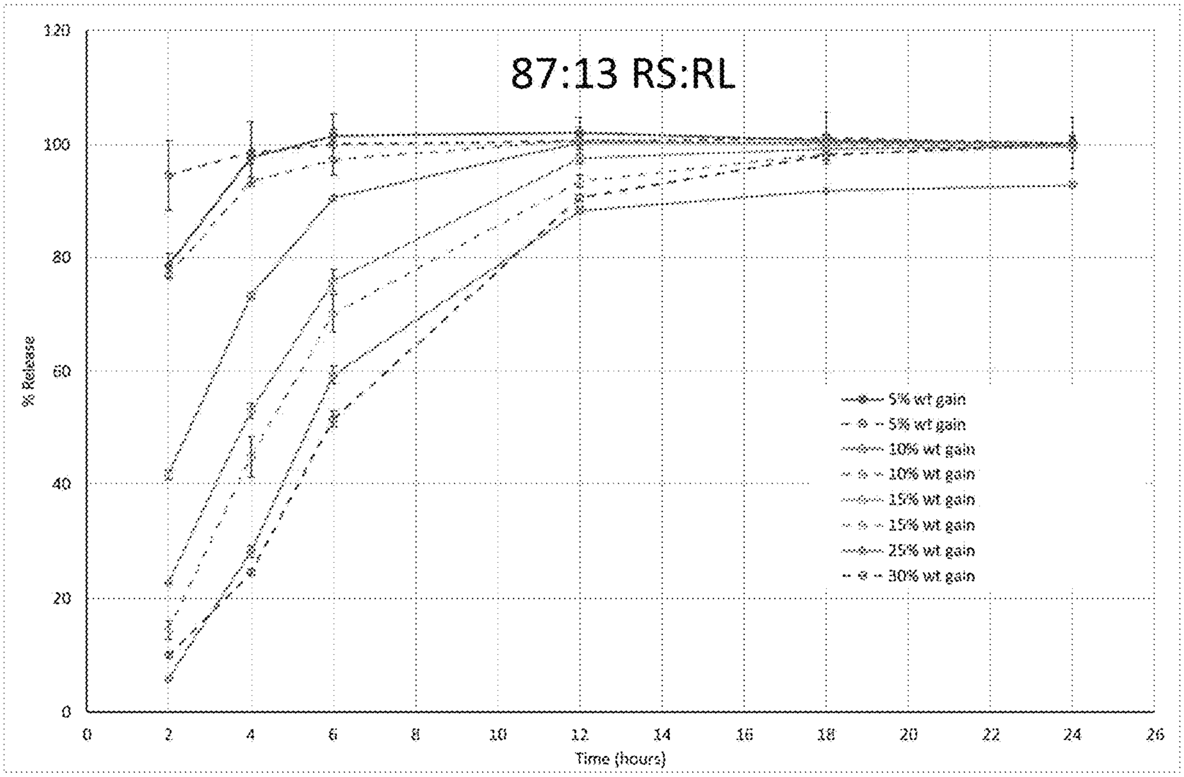
FIG. 12 shows a comparison of release profiles of nafamostat from the controlled release beads having an 87:13 (Eudragit RS:Eudragit RL) ratio with increasing weight gain.

FIG. 12 depicts a comparison of release profiles of nafamostat from the controlled release beads having an 87:13 (Eudragit RS:Eudragit RL) ratio with increasing weight gain.

Example 7: Preparation of Controlled Release Nafamostat Compositions

Nafamostat compositions containing controlled release beads were prepared. Each controlled release bead includes a microcrystalline cellulose core and an active agent layer of nafamostat mesylate and a controlled release polymeric coating layer. The active agent layer of nafamostat mesylate was prepared as set forth in Example 4. A polymeric controlled release coating solution with a 90:10 ratio of Eudragit RS:Eudragit RL was prepared as summarized in Table 8.

TABLE 8

Controlled release polymer layer of Nafamostat controlled release beads coating solution (90:10 Eudragit RS:Eudragit RL)

| Component | % w/w | Quantity (g)[1] |
|---|---|---|
| Eudragit RS PO | 6.483 | 64.83 |
| Eudragit RL PO | 0.720 | 7.20 |
| Triethyl Citrate | 0.720 | 7.20 |
| Micronized Talc | 1.800 | 18.00 |
| Acetone*,[2] | 34.396 | 343.95 |
| Isopropanol, Anhydrous*,[2] | 51.576 | 515.75 |
| Water for irrigation*,[2] | 4.306 | 43.06 |
| Total solution | 100.0000 | 999.99 |

*Removed during the process
[1]ER coating solution 9.72% solids
[2]Acetone/Isopropanol/water = 38.10:57.13:4.77 ratio In order to produce controlled release beads with slower release rates, the ratio of Eudragit RS:Eudragit RL was changed to 90:10. The Procept Fluid Bed was set up as previously described and 250 g of nafamostat active agent layer containing beads (as described above) were weighed out and loaded into the vessel. The coating solution was prepared producing a white opaque solution that was uniformly dispersed.

Coating was started and remained at 2.0 g/min for the duration of the coating process. Static issues were observed, with lots of beads sticking to the inside of the vessel and onto the filters. The filter pressure rapidly increased in this coating run, reaching 50 mbar in only 30 minutes. The blowback feature on the fluid bed was tested, but it didn't make any significant difference to the filter pressure. The air speed, nozzle flow and nozzle pressure were therefore reduced and tightly controlled to enable the process to continue for longer.

The process ran for approximately 4 hours and 30 minutes, achieving a theoretical 20% weight gain. Samples of the beads were taken at 5%, 10% and 20%. The bulk beads were cured in the vessel for 30 minutes at 40° C. and the samples placed in the oven at 40° C. for overnight curing.

Figure 13:
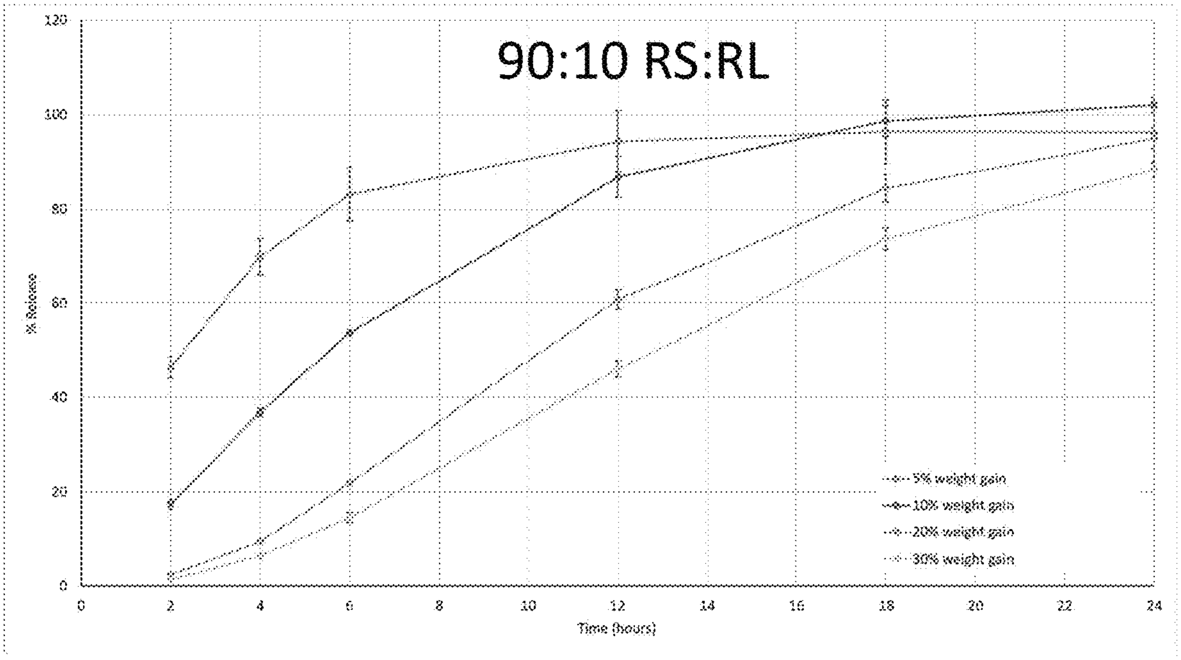
FIG. 13 shows a comparison of release profiles of nafamostat from the controlled release beads having a 90:10 (Eudragit RS:Eudragit RL) ratio with increasing weight gain.

The next morning the process was restarted, with the same bulk beads in the vessel and same coating solution. The filters were changed as they had exceeded 75 mbar. The aim of this additional coating was to try and achieve a 30% weight gain (an additional 10% on top of the 20% previously achieved). The process ran for a further 2 hours, a sample of the beads was taken at 30% weight gain and placed in the oven. Approximately 772 g coating solution was sprayed resulting in a theoretical coating weight gain of 30%. Using a 600 μm sieve, the ER coated beads were screened for twins. All weight gain samples were taken and analysed for dissolution and LOD. FIG. 13 shows a comparison of release profiles of nafamostat from the controlled release beads having a 90:10 (Eudragit RS:Eudragit RL) ratio with increasing weight gain.

Example 8: Preparation of Controlled Release Nafamostat Compositions

Nafamostat compositions containing controlled release beads were prepared. Each controlled release bead includes a microcrystalline cellulose core and an active agent layer of nafamostat mesylate and a controlled release polymeric coating layer. The active agent layer of nafamostat mesylate was prepared as set forth in Example 4. A polymeric controlled release coating solution with a 80:20 ratio of Eudragit RS:Eudragit RL was prepared as summarized in Table 9.

TABLE 9

Controlled release polymer layer of Nafamostat controlled release beads coating solution (80:20 Eudragit RS:Eudragit RL)

| Component | % w/w | Quantity (g)[1] |
|---|---|---|
| Eudragit RS PO | 5.762 | 28.81 |
| Eudragit RL PO | 1.440 | 7.20 |
| Triethyl Citrate | 0.720 | 3.60 |
| Micronized Talc | 1.800 | 9.00 |
| Acetone*,[2] | 34.396 | 171.98 |
| Isopropanol, Anhydrous*,[2] | 51.576 | 257.88 |
| Water for irrigation*,[2] | 4.306 | 21.53 |
| Total solution | 100.000 | 500.00 |

*Removed during the process
[1]ER coating solution 9.72% solids
[2]Acetone/Isopropanol/water = 38.10:57.13:4.77 ratio In order to produce controlled release beads with faster release rates, the ratio of Eudragit RS:Eudragit RL was changed to 80:20. The Procept Fluid Bed was set up as previously described and 250 g of nafamostat active agent layer containing beads (as described a above) were weighed out and loaded into the vessel. The coating solution was prepared producing a white opaque solution that was uniformly dispersed. Static in this trial was noticeable but could be controlled with the use of static guns. Stalactites formed on the bottom of the filters, but would disperse themselves. Avoiding touching the glass vessel helped to reduce the build-up of beads on the glass.

The process ran for approximately 3 hours, achieving a 15% weight gain. Samples of the beads were taken at 5% and 10%. The bulk beads were cured in the vessel and then transferred into a metal tray and placed into the oven overnight, along with the sample beads, at 40° C. By controlling the nozzle pressure and flow carefully, the filters didn't exceed 40 mbar allowing the process to continue running smoothly. Approximately 369 g coating solution was sprayed resulting in a theoretical coating weight gain of 15%. Using a 600 um sieve, the ER coated beads were screened for twins.

Figure 14A:
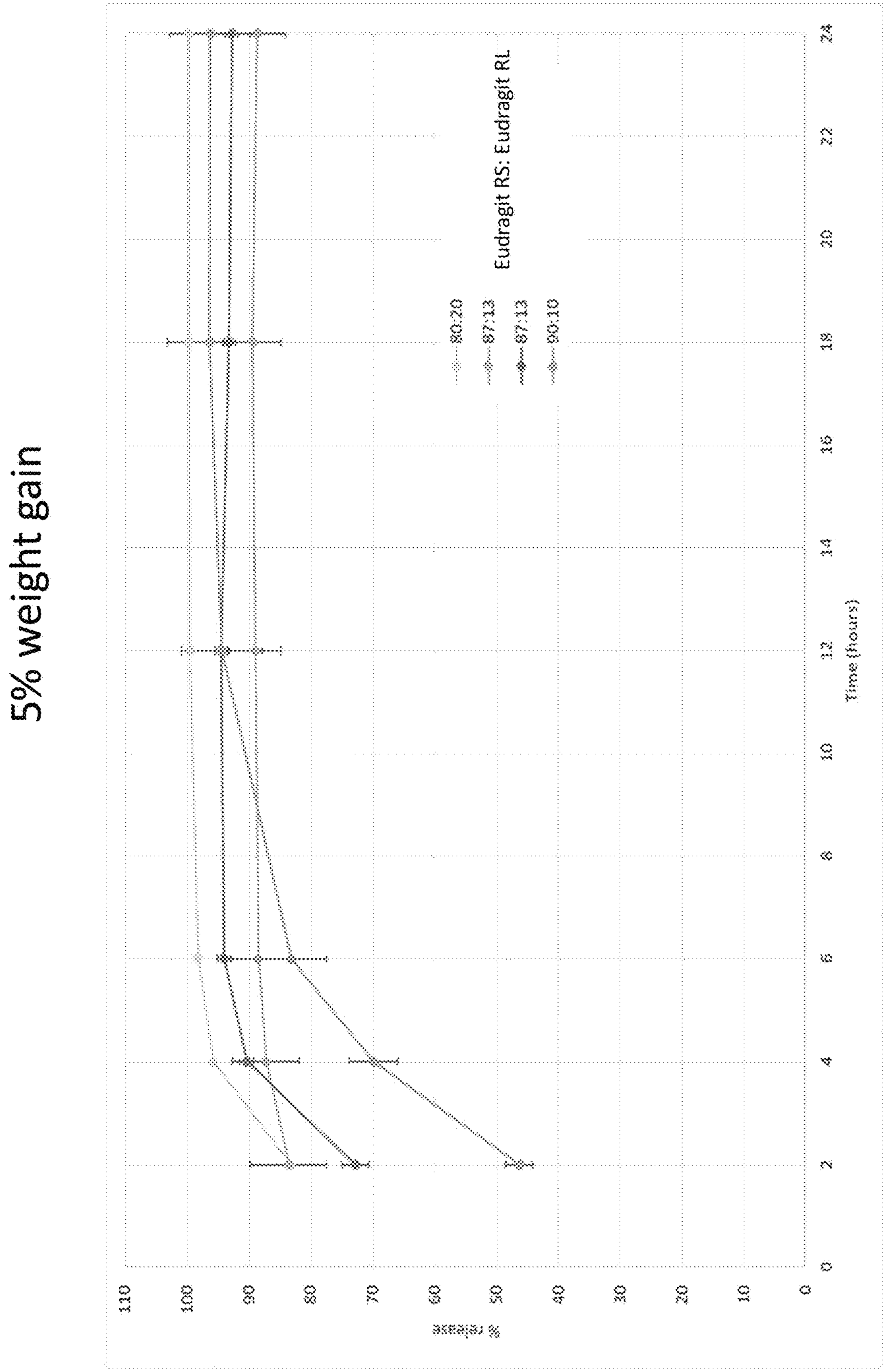
FIG. 14A shows a comparison of mean release profiles of nafamostat from the controlled release beads at 5% weight gain with different ratios of Eudragit RS:Eudragit RL in the controlled release polymeric layer.
Figure 14B:
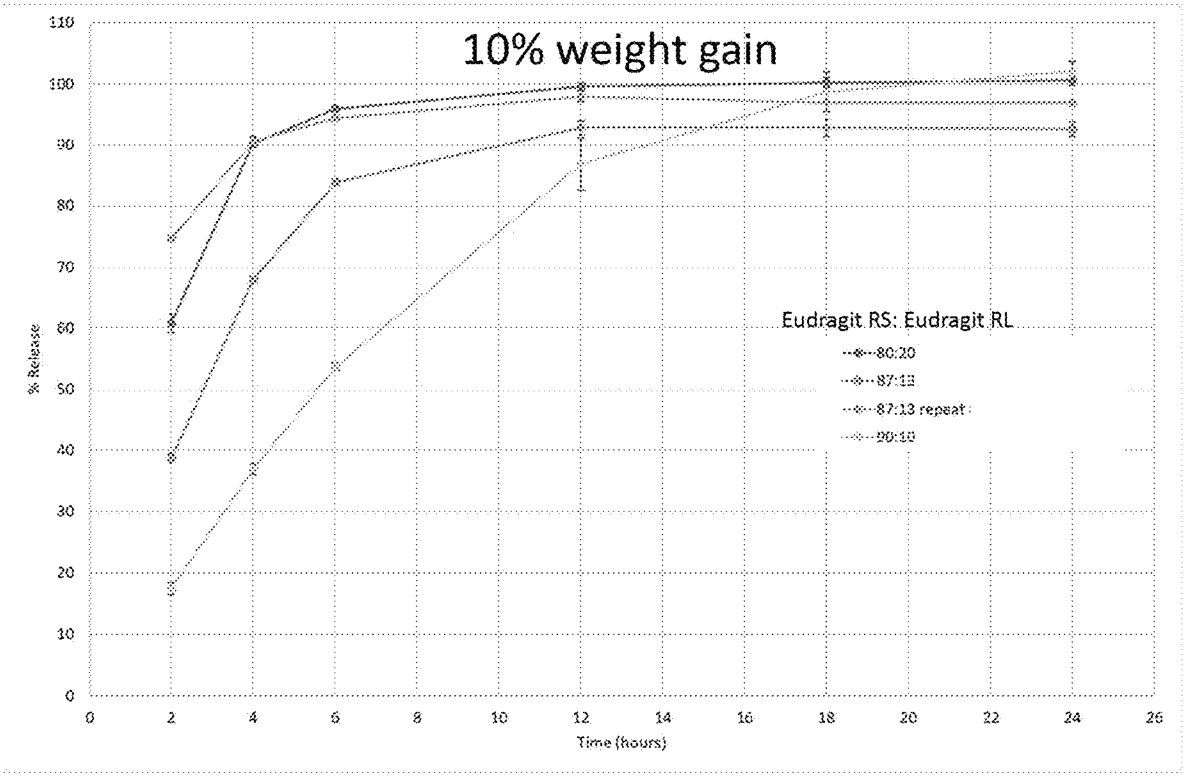
FIG. 14B shows a comparison of mean release profiles of nafamostat from the controlled release beads at 10% weight gain with different ratios of Eudragit RS:Eudragit RL in the controlled release polymeric layer.

A comparison of the mean release profiles of nafamostat for coated beads at 5% weight gain with different ratios of Eudragit RS:Eudragit RL is shown in FIG. 14A. A comparison of the mean release profiles of nafamostat for coated beads at 10% weight gain with different ratios of Eudragit RS:Eudragit RL is shown in FIG. 14B.

Example 9: Preparation of Controlled Release Nafamostat Compositions

Nafamostat compositions containing controlled release beads were prepared. Each controlled release bead includes a microcrystalline cellulose core and an active agent layer of nafamostat mesylate and a controlled release polymeric coating layer. The active agent layer of nafamostat mesylate was prepared as set forth in Example 4. A polymeric controlled release coating solution with a 92:8 ratio of Eudragit RS:Eudragit RL was prepared as summarized in Table 10. Syloid 244FP was used in place of micronized talc due to nozzle blockage and increased twinning of the generated beads.

TABLE 10

Controlled release polymer layer of Nafamostat controlled release beads coating solution (80:20 Eudragit RS:Eudragit RL)

| Component | % w/w | Quantity (g)[1] |
|---|---|---|
| Eudragit RS PO | 6.626 | 33.13 |
| Eudragit RL PO | 0.576 | 2.88 |
| Triethyl Citrate | 0.720 | 3.60 |
| Syloid 244FP | 1.800 | 9.00 |
| Acetone*,[2] | 34.396 | 171.98 |
| Isopropanol, Anhydrous*,[2] | 51.576 | 257.88 |
| Water for irrigation*,[2] | 4.306 | 21.53 |
| Total solution | 100.000 | 500.00 |

Figure 15:
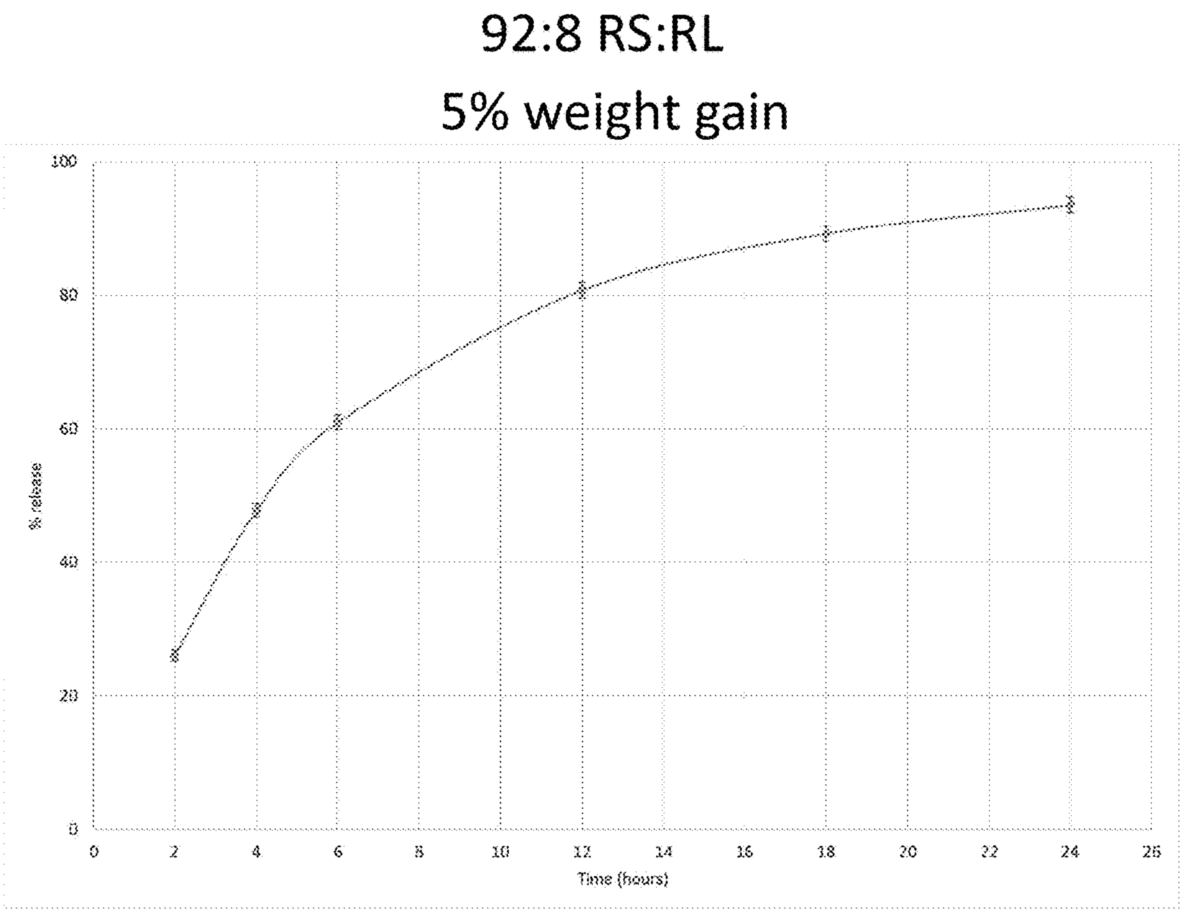
FIG. 15 shows a comparison of release profiles of nafamostat from the controlled release beads having a 92:8 (Eudragit RS:Eudragit RL) ratio at 5% weight gain.

*Removed during the process
[1]ER coating suspension 9.72% solids
[2]Acetone/Isopropanol/water = 38.10:57.13:4.77 ratio The Procept Fluid Bed was set up as previously described and 250 g of nafamostat active agent layer containing beads (as described above) were weighed out and loaded into the vessel. The process ran for approximately 3 hours, achieving a theoretical 15% weight gain. The bulk beads were cured in the vessel at 40° C. for 15 minutes and then transferred into a metal tray and placed into the oven overnight, at 40° C. LOD was taken following overnight curing and found to be comparable to previous batches (0.85%). By controlling the nozzle pressure and flow carefully, the filters didn't exceed 40 mbar allowing the process to continue running smoothly. Approximately 385 g coating solution was sprayed resulting in a coating weight gain of 15%. Using a 600 μm sieve, the ER coated beads were screened for twins. FIG. 15 shows a comparison of release profiles of nafamostat from the controlled release beads having a 92:8 (Eudragit RS:Eudragit RL) ratio at 5% weight gain.

Example 10: Preparation of Controlled Release Nafamostat Compositions

Nafamostat compositions containing controlled release beads were prepared. Each controlled release bead includes a microcrystalline cellulose core and an active agent layer of nafamostat mesylate and a controlled release polymeric coating layer. The active agent layer of nafamostat mesylate was prepared as set forth in Example 4. A polymeric controlled release coating solution with a 92:8 ratio of Eudragit RS:Eudragit RL was prepared as summarized in Table 11. Syloid 244FP was used in place of micronized talc due to nozzle blockage and increased twinning of the generated beads.

TABLE 11

| Controlled release polymer layer of Nafamostat controlled release beads coating solution (80:20 Eudragit RS:Eudragit RL) | | |
|---|---|---|
| Component | % w/w | Quantity (g)[1] |
| Eudragit RS PO | 5.306 | 26.53 |
| Eudragit RL PO | 1.768 | 8.84 |
| Triethyl Citrate | 0.708 | 3.54 |
| Syloid 244FP | 3.538 | 17.69 |
| Acetone*,[2] | 33.787 | 168.94 |
| Isopropanol, Anhydrous*,[2] | 50.663 | 253.32 |
| Water for irrigation*,[2] | 4.230 | 21.15 |
| Total solution | 100.000 | 500.00 |

Figure 16:
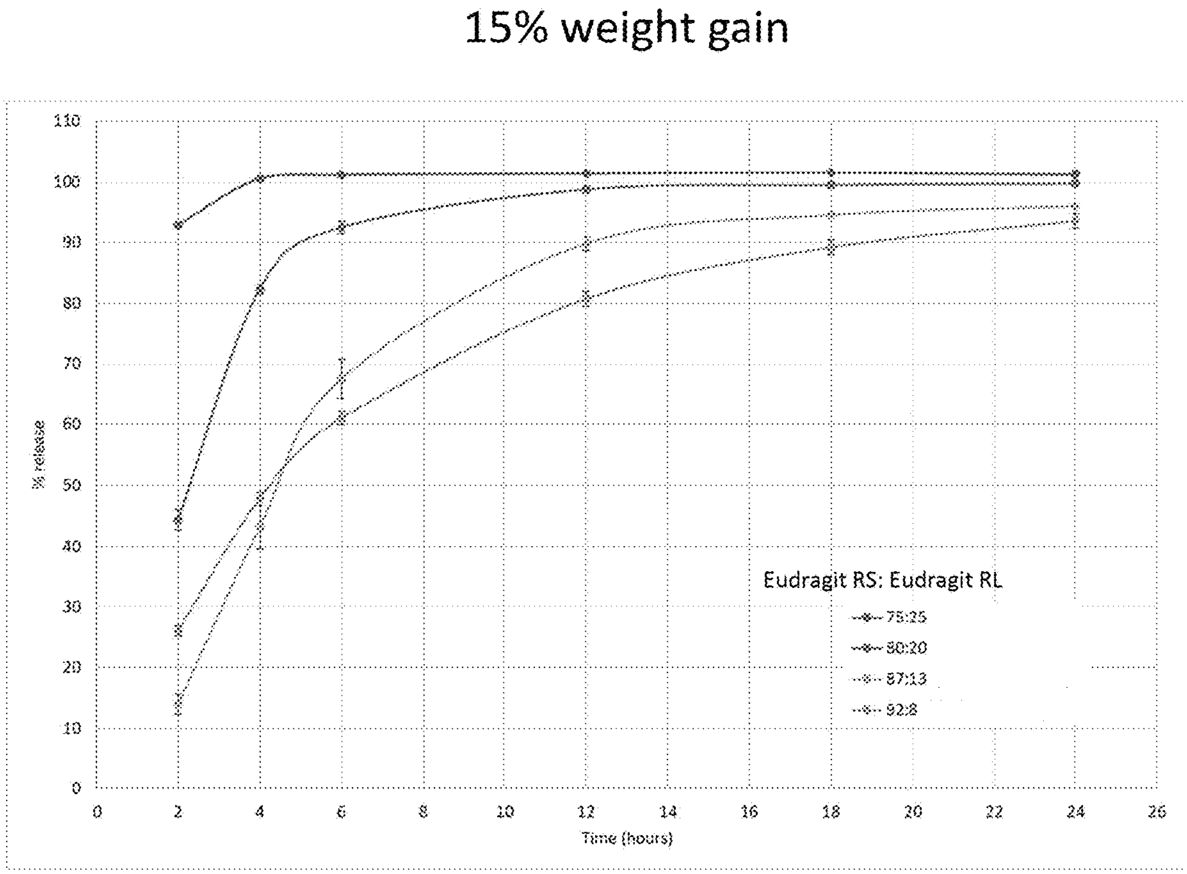
FIG. 16 shows a comparison of mean release profiles of nafamostat from the controlled release beads at 15% weight gain with different ratios of Eudragit RS:Eudragit RL in the controlled release polymeric layer having syloid 244FP in place of micronized talc.

*Removed during the process
[1]ER coating suspension 9.72% solidsμ
[2]Acetone/Isopropanol/water = 38.10:57.13:4.77 ratio The Procept Fluid Bed was set up as previously described and 250 g of nafamostat active agent layer containing beads (as described above) were weighed out and loaded into the vessel. The process ran for approximately 3 hours, achieving a 14.7% weight gain. The bulk beads were cured in the vessel at 40° C. for 10 minutes and then transferred into a metal tray and placed into the oven overnight, at 40° C. LOD was taken following overnight curing and found to be comparable to previous batches (0.68%). By controlling the nozzle pressure and flow carefully, the filters didn't exceed 40 mbar allowing the process to continue running smoothly. Approximately 324 g coating solution was sprayed resulting in a theoretical coating weight gain of 14.7%. Using a 600 μm sieve, the ER coated beads were screened for twins. FIG. 16 shows a comparison of mean release profiles of nafamostat from the controlled release beads at 15% weight gain with different ratios of Eudragit RS:Eudragit RL in the controlled release polymeric layer having syloid 244FP in place of micronized talc.

Example 11: Extended Release and Immediate Release Nafamostat in Minipigs

Drug formulations containing nafamostat using extended release beads were synthesized. In other words, present Example 3 studied the effect of substituting nafamostat in the drug formulations of Examples 1 and 2 (herein referred to as immediate release) with nafamostat in an extended release bead. The effect of the nafamostat formulation was measured by blood concentrations of oxycodone, which is released from KC-8 that was also administered.

The extended release drug formulation was a capsule containing multiple beads, wherein each bead had a spherical core of microcrystalline cellulose that was coated with an active agent layer, which was then coated with a controlled release layer (i.e. extended release layer or modified release layer). The active agent layer included a mixture of nafamostat and hypromellose, which is also known as hydroxylpropyl methylcellulose (HPMC). The controlled release layer included various ratios of Polymer A and Polymer B, along with triethyl citrate and talc. Polymer A was poly (ethylacrylate, methyl-methacrylate and chlorotrimethylammonioethyl methacrylate) containing about 50 mEq of quaternary ammonium groups per 100 g of polymer. Polymer A was purchased as Eudragit RL. Polymer B poly (ethylacrylate, methyl-methacrylate and chlorotrimethylammonioethyl methacrylate) containing about 25 mEq of quaternary ammonium groups per 100 g of polymer. Polymer B was purchased as Eudragit RS.

As shown in the table below, five different types of controlled release beads were synthesized based on different ratios of Polymer A to Polymer B.

| Controlled Release Bead | Polymer A : Polymer B Ratio |
|---|---|
| Bead B | 50:50 |
| Bead C | 20:80 |
| Bead D | 80:20 |
| Bead E | 100:0 |
| Bead F | 87:13 |

Six different studies were conducted, as described in the table below. In each study KC-8 was administered along with nafamostat. Whereas Studies 1-5 contained either immediate release or extended release nafamostat, Study 6 included equal amounts of both immediate release and extended release nafamostat.

| Study Number | Immediate Release Nafamostat | Extended Release Nafamostat Beads | Notes |
|---|---|---|---|
| 1 | No | Bead B, C, or D | |
| 2 | No | Yes; Bead D; either 0, 10, 50, or 100 mg | FIG. 7 |
| 3 | No | Yes; Bead E; either 0, 1, 5, or 10 mg/kg | FIG. 8 |
| 4 | Yes; either 0, 50, or 100 mg | No | FIG. 9 |
| 5 | No | Yes; Bead F; either 0, 50, or 100 mg | FIG. 10 |
| 6 | Yes; either 0, 25, or 100 mg | Yes; Bead F; either 0, 25, or 100 mg | FIG. 11 |

Study 1 involved administering KC-8 and either Beads B, C, or D. It was found that Beads B and C corresponded to high maximum concentrations of oxycodone, whereas Beads D caused lower maximum concentrations of oxycodone.

Figure 7:
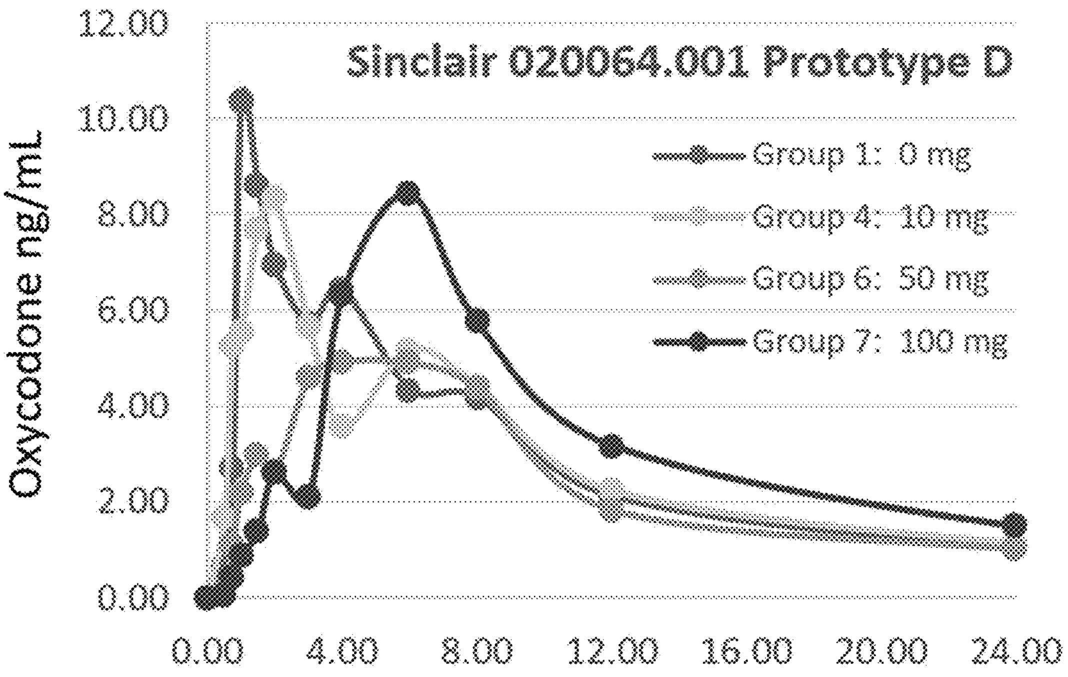
FIG. 7 shows the oxycodone concentration of minipigs administered KC-8 along with various amounts of nafamostat in Beads D.

Study 2 involved administered KC-8 to minipigs with either no nafamostat (control) or 10, 50, or 100 mg of nafamostat in Beads D. The results are shown in FIG. 7. It was found that increasing the nafamostat concentration from 0 to 10 and then 50 mg resulted in delaying Tmax from 2 to 4 hr and produced a decrease in the maximum oxycodone concentration from 10 ng/ml to about 5 ng/ml. It was found that 100 mg nafamostat Bead D resulted in delaying Tmax to 6 hr.

Figure 8:
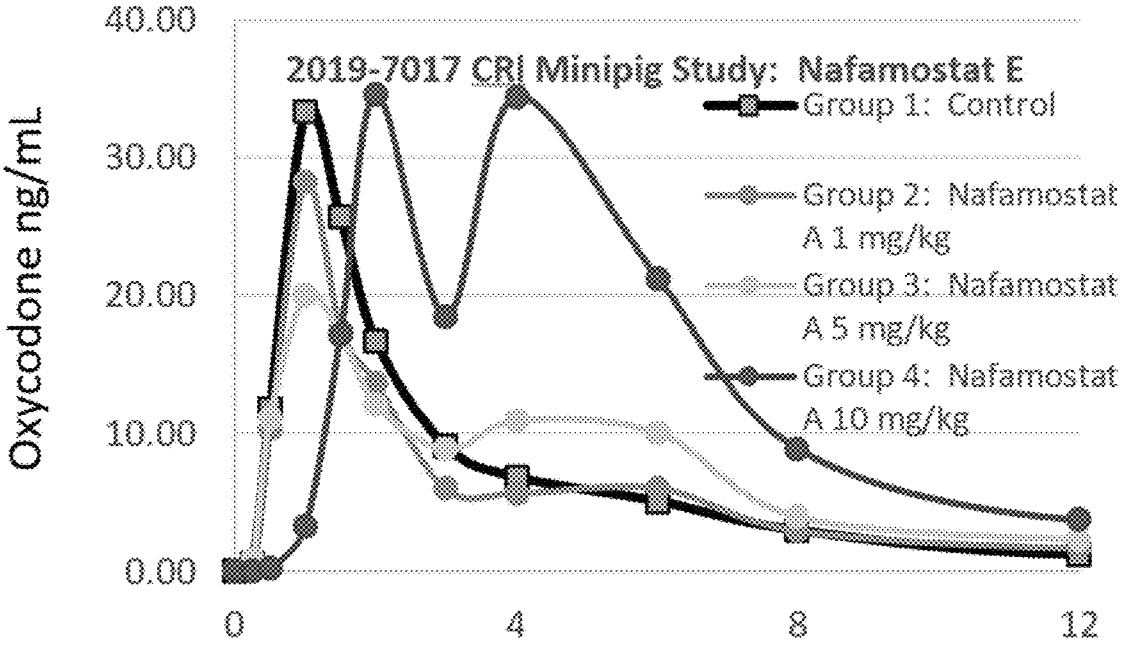
FIG. 8 shows oxycodone concentration in minipigs administered KC-8 along with nafamostat in Beads E.

Study 3 involved administering Beads E, which had a 100:0 ratio of Polymer A to Polymer B. When increasing the nafamostat concentration from 0 to 1 to 5 mg/kg the maximum oxycodone concentration decreased from about 34 ng/ml to about 20 ng/ml with a Tmax of 1 hour, as shown in FIG. 8. The 10 mg/kg nafamostat delayed the time to reach maximum oxycodone concentration (Tmax) to 2 hr.

Figure 9:
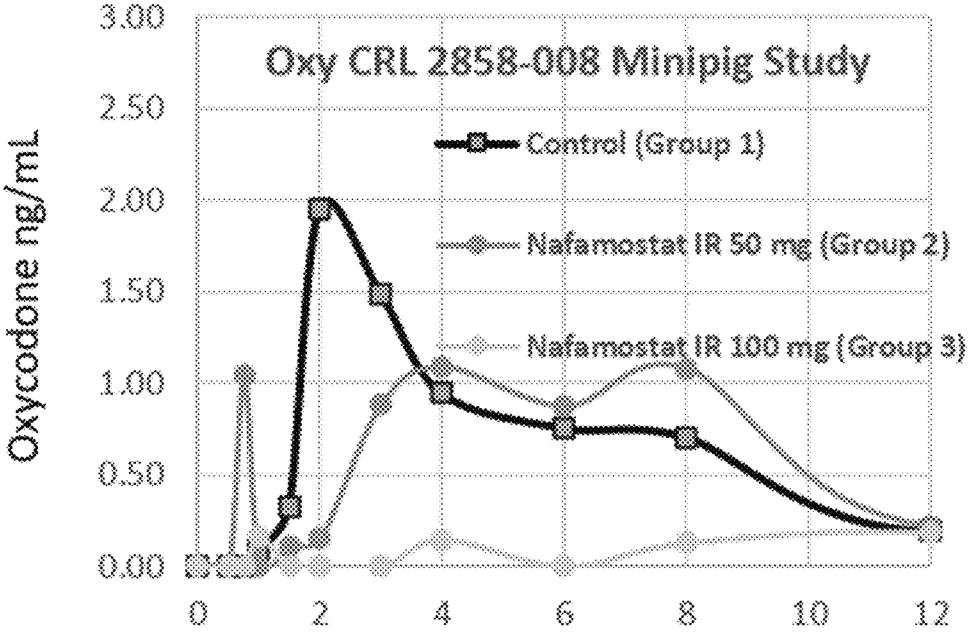
FIG. 9 shows oxycodone concentration in minipigs administered KC-8 with immediate release nafamostat.

Study 4 involved administering immediate release nafamostat that was not part of an extended release bead, as shown in FIG. 9. Increasing the amount of immediate release nafamostat from 0 to 50 mg resulted in a decrease of maximum oxycodone from 2 to 1 ng/ml. Further increasing immediate release nafamostat to 100 mg further decreased the maximum oxycodone to about 0.2 ng/ml.

Figure 10:
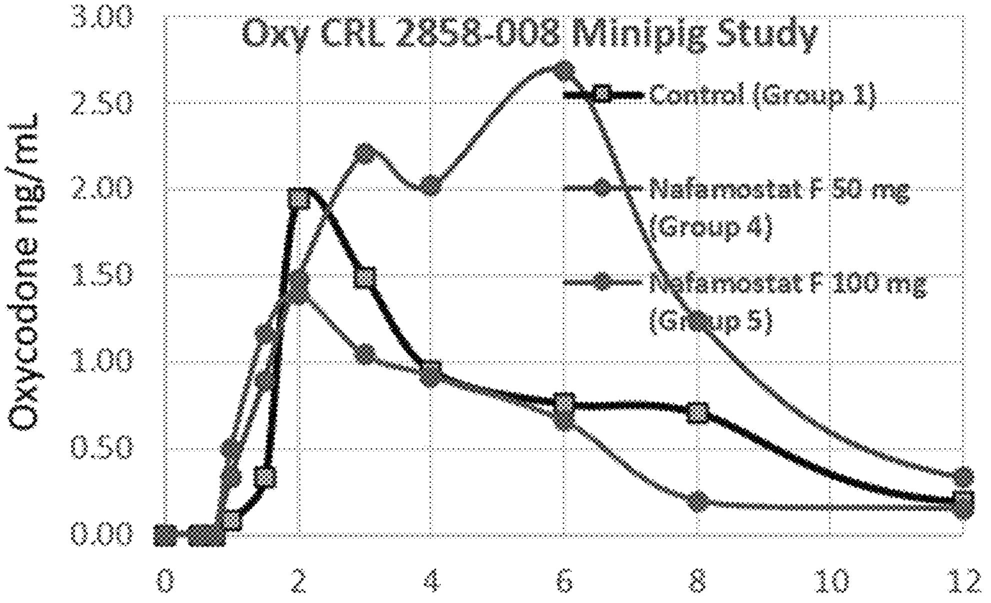
FIG. 10 shows oxycodone concentration in minipigs administered nafamostat in Beads F.

Study 5 involved administering nafamostat in Beads F. As shown in FIG. 10, the maximum oxycodone was 2 ng/ml with no nafamostat but only about 1.5 ng/ml with 100 mg of nafamostat in Beads F with a Tmax of 2 hr. Increasing the nafamostat dose to 100 mg resulted in a Tmax of oxycodone blood levels of 6 hr.

Figure 11:
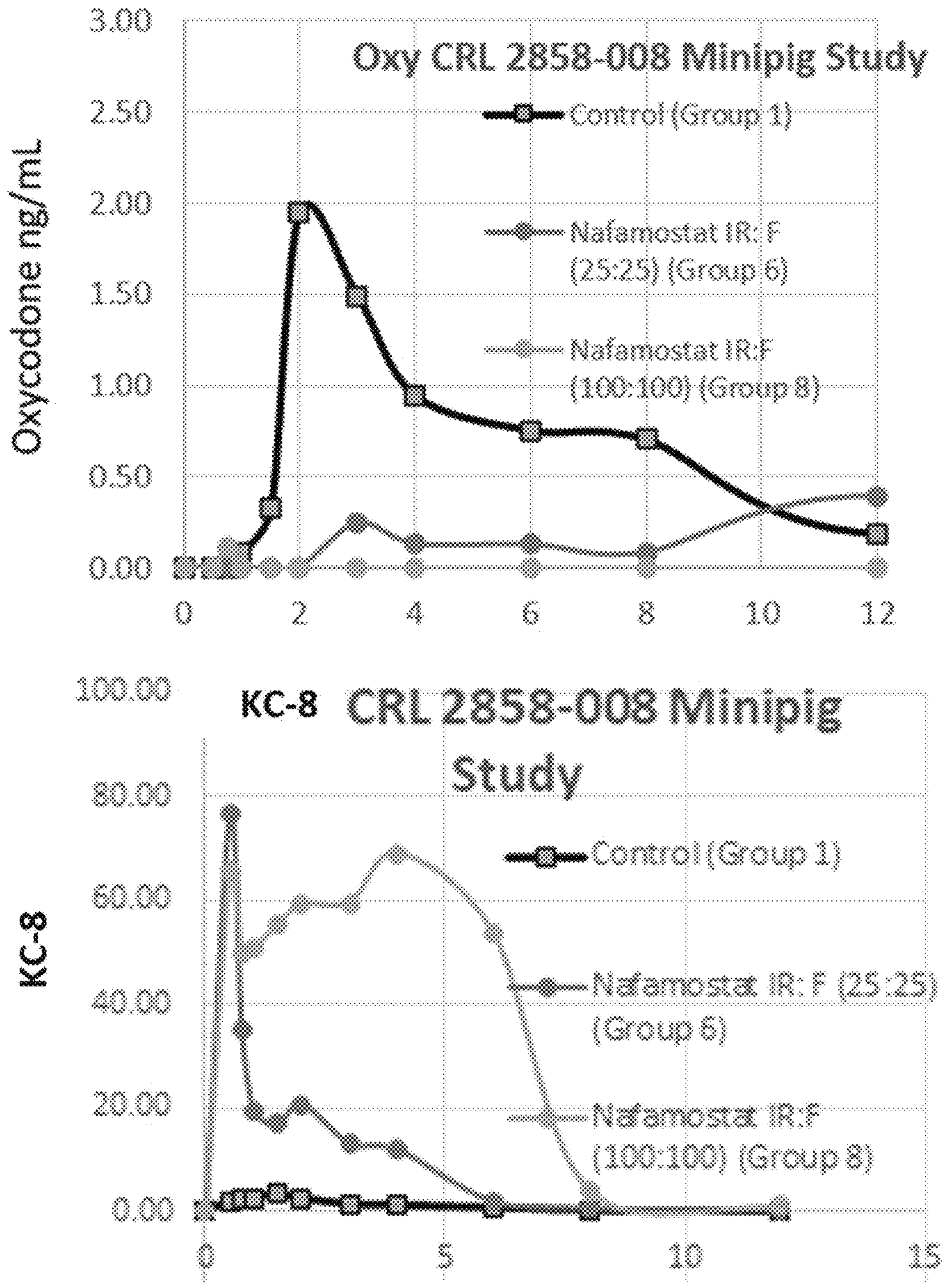
FIG. 11 shows oxycodone and KC-8 concentration in minipigs administered a combination of immediate release nafamostat and nafamostat in Beads F.

Study 6 involved administering an equal amount of both immediate release nafamostat and Beads F nafamostat. In particular, the minipigs received either no nafamostat (control), 25 mg of immediate release and 25 mg of Bead F nafamostat, or 100 mg of immediate release and 100 mg of Bead F nafamostat. FIG. 11 shows not only the concentration of oxycodone, but also the concentration of the oxycodone derivative of KC-8. Increasing the amount of Bead F nafamostat in combination with immediate release nafamostat decreased the maximum oxycodone concentration from about 2 ng/ml to about 0.3 or 0.1 ng/ml. Concurrently, KC-8 concentrations increased with increasing Bead F nafamostat in combination with immediate release nafamostat.

Example 12: Human Trials with KC-8 and Nafamostat in Immediate and Extended Release Formulations Human trials can be conducted wherein the effect of immediate and extended release nafamostat on KC-8 metabolism can be examined.

The study can involve modifying the dosage of nafamostat and/or the ratio of Polymer A to Polymer B in the extended release nafamostat beads, such as depending on the observations regarding oxycodone concentrations in the blood of the subjects. In other words, the controlled release layer containing Polymers A and B can be modified such that the release kinetics can be modified for optimal concentrations of oxycodone in subject blood. In some cases the formulation can also include nafamostat that is not within the controlled release beads, e.g. so that it can in some cases rapidly be available for pharmaceutical effect.

A Single Dose 2-Part Study to Evaluate the Pharmacokinetics of Oxycodone, KC-8, PFR06082, and Nafamostat, when KC-8 Solution is Co-Administered, as an Immediate Release Solution and/or Extended Release (ER) Capsule Formulations in Healthy Subjects.

The primary objective of Part 1 can be to assess the pharmacokinetics (PK) of oxycodone, when KC-8 solution is administered alone and with nafamostat as an immediate-release (IR) solution and/or extended-release (ER) capsule prototypes. The primary objective of Part 2 can be to determine the effect of the selected combinations of nafamostat IR solution and/or ER prototype capsule(s) on the PK of oxycodone at multiple dose levels of KC-8 solution and the selected nafamostat IR/ER formulation.

Part 1 Methodology

Part 1 of the study has a 6-period, randomized, open-label design. It is planned to enroll 24 healthy subjects, with roughly equal numbers of males and females who will take part in all 6 periods in Part 1. The 24 enrolled subjects will consist of an even number of males and an even number of females (eg, 12 males and 12 females; 14 males and 10 females etc.), with a roughly equal number of males and females if possible. Subjects will then be randomized between 2 groups (Group 1 or Group 2) of 12 subjects each, to achieve approximately 8 evaluable subjects per group.

In both groups, subjects will receive the KC-8 solution alone (reference; Period 1) and concomitantly with nafamostat (as an IR solution and/or ER prototype capsule[s], in Periods 2 to 6). In addition, prior to and following each regimen in all periods, subjects will receive blocking doses of the opiate antagonist naltrexone to reduce the opioid-related side effects.

Both groups are planned to be dosed in parallel (with some flexibility in the dosing day for scheduling purposes); however, after Period 3 (Regimens 1C and 2C) there is the option for the groups to merge. Groups may be merged for subsequent periods (with all subjects receiving the same regimen for any dosing period) to gain increased precision of PK parameters in regimens likely to be progressed in future studies. If this option is progressed, there is also the option for the merged group to be split into Group 1 and Group 2 again for subsequent regimens based on emerging PK and safety data.

Interim reviews of the safety and PK data for oxycodone, KC-8 and PFR06082 to 48 h post-dose will take place after Periods 2, 3, 4 and 5 to decide upon the following:

- Nafamostat formulation(s) to dose (dose of IR solution, and/or release rate and dose of ER prototype capsule[s], as applicable) in the subsequent period;
- After Period 3 only: whether to merge or split the groups;
- After Period 4 only (for each group if Period 5 will be split): The prandial status (fed vs. fasted) for Period 5;
- After Period 5 only (for each group if Period 6 will be split): The dose levels for both the KC-8 solution and nafamostat formulations in Period 6.

Extended-release prototype capsule formulations will be selected from a 2-dimensional design space describing formulation variables for release rate (determined by the Eudragit RS:RL coating ratio 90% release in 2 to 16 h) and dose (1 to 100 mg).

Note that the nafamostat formulation (IR and/or ER) to be dosed in the fed state in Period 5 will be the formulation selected to be dosed in Part 2 of the study.

The regimens presented on the next page (the IMPs KC-8 and nafamostat, and the NIMP naltrexone) will be administered in a sequential manner to each group.

Part 2 Methodology

Part 2 of the study has a 5-period, non-randomized, open-label design. It is planned that the 12 healthy subjects will be enrolled into Part 2 of the study, to achieve a minimum of 8 evaluable subjects.

Subjects will receive the KC-8 solution concomitantly with the selected combination of nafamostat IR solution and/or ER prototype capsule(s) from Part 1 (defined as 1 dose unit; ie, 1 Dose Unit=KC-8 solution [25 mg]+the selected nafamostat formulation [IR and/or ER prototype capsule {ZZ mg}]). In each period the subjects will receive an increased number of dose units. Hence a fixed ratio of KC-8:nafamostat will be administered at increasing dose levels, to simulate overdose. Note, this is a simulation of an overdose; however, the total dose of KC-8 will not exceed 200 mg (equivalent to 80 mg oxycodone) as was delivered in a Phase 1 single ascending dose study, and therefore will remain within safe and well tolerated levels. In addition, the fixed ratio selected for Part 2 will be a higher KC-8/nafamostat dose ratio than Part 1. It is expected that a 10:1 dose ratio of KC-8 vs nafamostat will be used in Part 2. It is planned that Part 1 will use a lower dose, ratio ranging from 1:1 to 2.5:1; however, these ratios may be modified based on emerging PK data from Part 1.

In addition, prior to and following each regimen, subjects will receive doses of the opiate antagonist naltrexone to reduce the opioid-related side effects.

The combination of nafamostat IR solution and/or ER prototype capsule(s) and dose to be administered in Period 1 (Regimen G) will be determined following interim review of the Part 1 safety and PK data out to 48 h post-dose. Interim reviews of the safety and PK data to 48 h post-dose will also take place after Periods 1, 2, 3 and 4 to decide if escalation to the next planned number of dose units may proceed, and the number of dose units to be administered. In addition, it is planned to assess nafamostat PK in Regimen K (Period 5), which is predicted to be the highest dose level administered. However, if this regimen doesn't administer the highest dose level in Part 2, there is an option to analyze previous regimens for nafamostat PK using the PK back-up samples from a previous regimen. This decision will take place during the interim review after Period 4.

There will be a final review after Period 5 in order to look at the interim data prior to data reporting in the Clinical Study Report.

The highest dose level of KC-8 solution to be administered in Part 2 will be 200 mg (8×25 mg), which is equivalent to 80 mg oxycodone. In previous SAD study with KC-8, doses of up to 200 mg (80 mg oxycodone) have been shown to be safe and well tolerated. The highest dose level of nafamostat that may be administered will be 200 mg, which has been shown to be safe and well tolerated from the 200 mg healthy volunteer SAD data.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A composition comprising:

an active agent prodrug selected from the group consisting of:

1) a compound of formula KC-(IIIa):

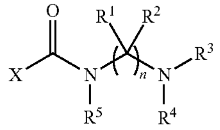

(KC-(IIIa))

wherein:

X represents a residue of a ketone-containing opioid, wherein the hydrogen atom of the corresponding enolic group of the ketone is replaced by a covalent bond to $—C(O)\text{-}NR^5—(C(R^1)(R^2))_n—NR^3R^4$;

$R^5$ is selected from alkyl, substituted alkyl, arylalkyl, substituted arylalkyl, aryl and substituted aryl;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl, substituted cycloalkyl, aryl, or substituted aryl group, or two $R^2$ or $R^3$ groups on adjacent carbon atoms, together with the carbon atoms to which they are attached, form a cycloalkyl, substituted cycloalkyl, aryl, or substituted aryl group;

n is an integer from 2 to 4;

$R^3$ is hydrogen or (1-4C) alkyl;

$R^4$ is

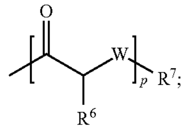

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;

each W is independently $—NR^8—$, —O— or —S—;

each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

p is an integer from one to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate;

2) a compound of formula PC-(I)

$$X—C(O)—NR^1—(C(R^2)(R^3))_n—NH—C(O)—CH(R^4)—NH(R^5) \quad \text{(PC-(I))}$$

or a pharmaceutically acceptable salt thereof, wherein:

X represents a residue of a phenolic opioid, wherein the hydrogen atom of the phenolic hydroxyl group is replaced by a covalent bond to —C(O)—$NR^1$—(C($R^2$)($R^3$))$_n$—NH—C(O)—CH($R^4$)—NH($R^5$);

$R^1$ represents a (1-4C) alkyl group;

$R^2$ and $R^3$ each independently represents a hydrogen atom or a (1-4C) alkyl group; n represents 2 or 3;

$R^4$ represents —$CH_2CH_2CH_2NH$(C═NH)$NH_2$ or —$CH_2CH_2CH_2CH_2NH_2$, the configuration of the carbon atom to which $R^4$ is attached corresponding with that in an L-amino acid; and $R^5$ represents a hydrogen atom, an N-acyl group, or a residue of an amino acid, a dipeptide, or an N-acyl derivative of an amino acid or dipeptide; and 3) a compound of formula AM-(I):

AM-(I)

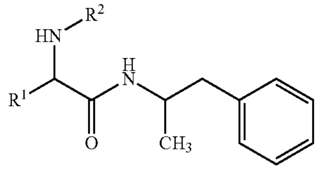

wherein $R^1$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl; and $R^2$ is an acyl, substituted acyl, or an N-acyl derivative of a peptide;

or a salt, hydrate or solvate thereof; and an oral composition comprising nafamostat or a pharmaceutically acceptable salt thereof, wherein the composition comprises:

an immediate release composition comprising nafamostat or a pharmaceutically acceptable salt thereof; and a plurality of controlled release beads, each bead comprising:

a core;

an active agent layer comprising nafamostat or a pharmaceutically acceptable salt thereof; and a controlled release layer comprising one or more polymers.

2. The composition of claim 1, wherein the core comprises a cellulose polymer, or silicon dioxide, or a sugar selected from the group consisting of glucose, sucrose, lactose, mannitol, xylitol, and sorbitol.

3. The composition of claim 1, wherein the active agent layer further comprises a binder.

4. The composition of claim 1, wherein the controlled release layer comprises a combination of:

acrylate copolymer A comprising poly (ethylacrylate, methyl-methacrylate and chlorotrimethyl-ammonioethyl methacrylate) comprising about 50 mEq of quaternary ammonium groups per 100 g of polymer; and acrylate copolymer B comprising poly (ethylacrylate, methyl-methacrylate and chlorotrimethyl-ammonioethyl methacrylate) comprising about 25 mEq of quaternary ammonium groups per 100 g of polymer.

5. The composition of claim 4, wherein the controlled release layer comprises:

acrylate copolymer comprises: 95% by weight acrylate copolymer B and 5% by weight acrylate copolymer A;

acrylate copolymer comprises: 93% by weight acrylate copolymer B and 7% by weight acrylate copolymer A;

acrylate copolymer comprises: 92% by weight acrylate copolymer B and 8% by weight acrylate copolymer A;

acrylate copolymer comprises: 90% by weight acrylate copolymer B and 10% by weight acrylate copolymer A;

acrylate copolymer comprises 87% by weight acrylate copolymer B and 13% by weight acrylate copolymer A;

acrylate copolymer comprises: 80% by weight acrylate copolymer B and 20% by weight acrylate copolymer A; or acrylate copolymer comprises: 70% by weight acrylate copolymer B and 30% by weight acrylate copolymer A.

6. The composition of claim 1, wherein the controlled release layer comprises from 5% and 30% by weight of each of the plurality of beads.

7. The composition of claim 1, wherein the active agent layer or the controlled release layer further comprise a plasticizer.

8. The composition of claim 1, wherein each of the plurality of beads comprises from 5% and 20% by weight of the nafamostat or a pharmaceutically acceptable salt thereof.

9. The composition of claim 1, wherein the composition comprises a plurality of controlled release beads, each bead comprising:

a microcrystalline cellulose core;

an active agent layer comprising nafamostat or a pharmaceutically acceptable salt thereof and a water soluble methylcellulose polymer; and a controlled release layer comprising:

a first polymer comprising poly (ethylacrylate, methylmethacrylate and chlorotrimethyl-ammonioethyl methacrylate) containing about 50 mEq of quaternary ammonium groups per 100 g of polymer;

a second polymer comprising poly (ethylacrylate, methyl-methacrylate and chlorotrimethyl-ammonioethyl methacrylate) containing about 25 mEq of quaternary ammonium groups per 100 g of polymer;

triethyl citrate; and a glidant selected from micronized talc and syloid, wherein the controlled release layer is formulated to provide for controlled release of the nafamostat or pharmaceutically acceptable salt thereof.

10. The composition of claim 9, wherein the controlled release layer is formulated to provide for release of 60% or more of the nafamostat or pharmaceutically acceptable salt thereof within 6 hours after administration.

11. The composition of claim 9, wherein the controlled release layer is formulated to provide for release of nafamostat or pharmaceutically acceptable salt thereof at a first rate for a first predetermined period of time followed by release of the nafamostat or pharmaceutically acceptable salt thereof at a second rate for a second predetermined period of time.

12. A method comprising administering to a subject in need thereof a composition of claim 1.

* * * * *